(12) United States Patent
Carroll et al.

(10) Patent No.: US 9,108,014 B2
(45) Date of Patent: Aug. 18, 2015

(54) FLEXIBLE STRUCTURE FOR MASK, AND METHOD AND APPARATUS FOR EVALUATING PERFORMANCE OF A MASK IN USE

(75) Inventors: Fiona Catherine Carroll, Concord (AU); Joshua Adam Gudiksen, Mortdale (AU); Robin Garth Hitchcock, Normanhurst (AU); Daniel Robert Judson, Lapstone (AU); Philip Rodney Kwok, Chatswood (AU);

(Continued)

(73) Assignee: ResMed Limited, Bella Vista (AU)

( * ) Notice: Subject to any disclaimer, the term of this patent is extended or adjusted under 35 U.S.C. 154(b) by 306 days.

(21) Appl. No.: 12/736,980

(22) PCT Filed: May 29, 2009

(86) PCT No.: PCT/AU2009/000682
§ 371 (c)(1),
(2), (4) Date: Feb. 15, 2011

(87) PCT Pub. No.: WO2009/143586
PCT Pub. Date: Dec. 3, 2009

(65) Prior Publication Data
US 2011/0162654 A1    Jul. 7, 2011

Related U.S. Application Data

(63) Continuation-in-part of application No. PCT/AU2008/001711, filed on Nov. 17, 2008.

(30) Foreign Application Priority Data

May 29, 2008 (AU) .................................. 2008902720
Jun. 27, 2008 (AU) .................................. 2008903294
Jul. 22, 2008 (EP) ...................................... 08160921
Jan. 30, 2009 (AU) .................................. 2009900323
May 14, 2009 (AU) .................................. 2009902153

(51) Int. Cl.
*A62B 18/08* (2006.01)
*A61M 16/06* (2006.01)

(52) U.S. Cl.
CPC ........... *A61M 16/06* (2013.01); *A61M 16/0622* (2014.02); *A61M 16/0633* (2014.02); *A61M 2205/332* (2013.01); *A61M 2209/02* (2013.01)

(58) Field of Classification Search
CPC ............ A61M 16/06; A61M 16/0605; A61M 16/1616; A61M 16/0622; A61M 2016/0661
USPC ............. 128/206.21, 206.23, 206.24, 206.26, 128/206.28, 207.13
See application file for complete search history.

(56) References Cited

U.S. PATENT DOCUMENTS 3,330,273 A   7/1967 Bennett
4,907,584 A   3/1990 McGinnis (Continued)

FOREIGN PATENT DOCUMENTS

CN   1 735 439   2/2006
EP   0 427 474   5/1991

(Continued)

OTHER PUBLICATIONS

Examination Report issued in related New Zealand Appln. No. 589845 (Jan. 4, 2012).

(Continued)

*Primary Examiner* — Kristen Matter
(74) *Attorney, Agent, or Firm* — Nixon & Vanderhye P.C.

(57) ABSTRACT

A respiratory mask includes a frame and a flexible structure provided to the frame and adapted to engage a patient's face. The flexible structure includes a chamber filled with a first gel and a second gel that is relatively harder than the first gel. A ratio of height of the first gel to the second gel in a lip region is in the range of about 0.25 to about 0.6.

21 Claims, 74 Drawing Sheets

(72) Inventors: Damien Julian Mazzone, Concord West (AU); Vishnu Saralertsophon, Bella Vista (AU); Christopher Scott Skipper, North Ryde (AU); Matthew David Spruell, Bella Vista (AU); Enrico Brambilla, Drummoyne (AU); Bernd Lang, Grafelfing (DE); Achim Biener, Aufkirchen (DE); Johannes Nickol, Stanhope (DE); Johann Sebastian Burz, Germaringen (DE)

(56) References Cited

U.S. PATENT DOCUMENTS

| | | | |
|---|---|---|---|
| 4,944,310 | A | 7/1990 | Sullivan |
| 5,560,354 | A * | 10/1996 | Berthon-Jones et al. ... 128/205.25 |
| 5,884,624 | A | 3/1999 | Barnett et al. |
| 6,019,101 | A | 2/2000 | Cotner et al. |
| 6,082,360 | A | 7/2000 | Rudolph et al. |
| 6,196,223 | B1 | 3/2001 | Belfer et al. |
| 6,397,847 | B1 | 6/2002 | Scarberry et al. |
| 6,467,483 | B1 | 10/2002 | Kopacko et al. |
| 6,615,832 | B1 | 9/2003 | Chen |
| 6,631,718 | B1 | 10/2003 | Lovell |
| 6,907,882 | B2 * | 6/2005 | Ging et al. ... 128/207.11 |
| 7,216,647 | B2 | 5/2007 | Lang et al. |
| 2002/0100479 | A1 | 8/2002 | Scarberry et al. |
| 2003/0168063 | A1 | 9/2003 | Gambone et al. |
| 2005/0199239 | A1 * | 9/2005 | Lang et al. ... 128/206.24 |
| 2006/0076018 | A1 | 4/2006 | Barnett et al. |
| 2007/0163594 | A1 | 7/2007 | Ho et al. |
| 2007/0221227 | A1 | 9/2007 | Ho |
| 2008/0149104 | A1 | 6/2008 | Eifler |
| 2008/0289633 | A1 * | 11/2008 | Kwok et al. ... 128/206.24 |
| 2010/0018534 | A1 * | 1/2010 | Veliss et al. ... 128/206.24 |
| 2010/0294281 | A1 * | 11/2010 | Ho ... 128/206.24 |
| 2011/0088698 | A1 * | 4/2011 | Barnett et al. ... 128/206.24 |
| 2011/0088699 | A1 * | 4/2011 | Skipper et al. ... 128/206.26 |

FOREIGN PATENT DOCUMENTS

| | | |
|---|---|---|
| EP | 0 935 971 | 8/1998 |
| EP | 08160921.6 | 7/2008 |
| EP | 2 147 769 | 1/2010 |
| JP | 9207152 | 8/1997 |
| JP | 9216240 | 8/1997 |
| JP | 2002-526180 | 8/2002 |
| JP | 2005-529687 | 10/2005 |
| WO | WO 03/016018 | 2/2003 |
| WO | WO 2004/007010 | 1/2004 |
| WO | WO 2007/009182 | 1/2007 |
| WO | WO 2007/045023 | 4/2007 |
| WO | WO 2007/104042 | 9/2007 |
| WO | WO 2009/062265 | 5/2009 |

OTHER PUBLICATIONS

First Examination Report in New Zealand Appln. No. 701072 dated Oct. 28, 2014.

International Search Report issued in Appln. No. PCT/AU2009/000682 (Sep. 9, 2009).

Office Action issued in corresponding Chinese Appln. No. 200980119658.1 dated Jun. 20, 2014, with English translation thereof.

Office Action issued in a corresponding Chinese Application No. 200980119658.1, dated Nov. 19, 2013 with English language translation thereof.

First Examiner Report issued in a corresponding New Zealand Application No. 610184, dated May 10, 2013.

Office Action issued in related U.S. Appl. No. 12/734,740 dated May 30, 2014.

Decision of Rejection issued in corresponding Chinese Appln. No. 200980119658.1 dated Jan. 12, 2015, with English translation thereof.

Office Action issued in a corresponding Chinese Appl. No. 200980119658.1 (Jan. 4, 2013) with English translation thereof.

Extended European Search Report issued in corresponding European Appln. No. 09 75 3350.9 dated Apr. 24, 2015.

* cited by examiner

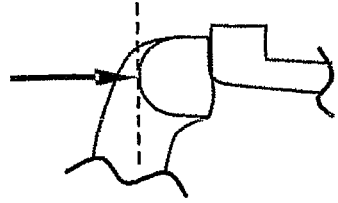
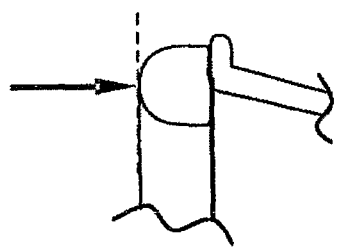
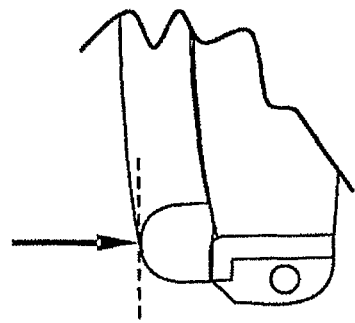
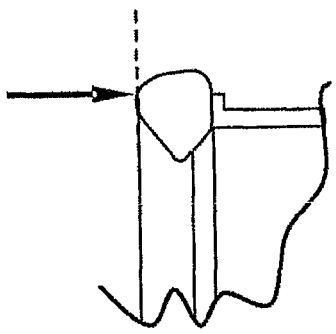
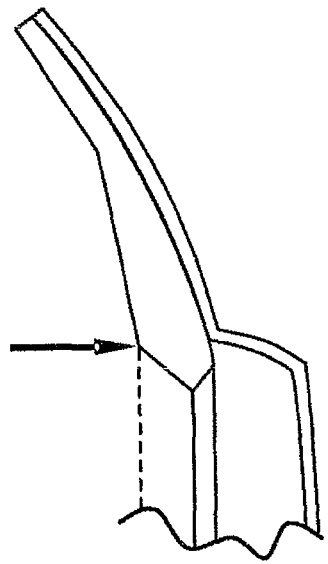
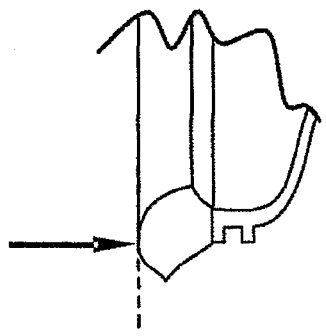
Fig. 66

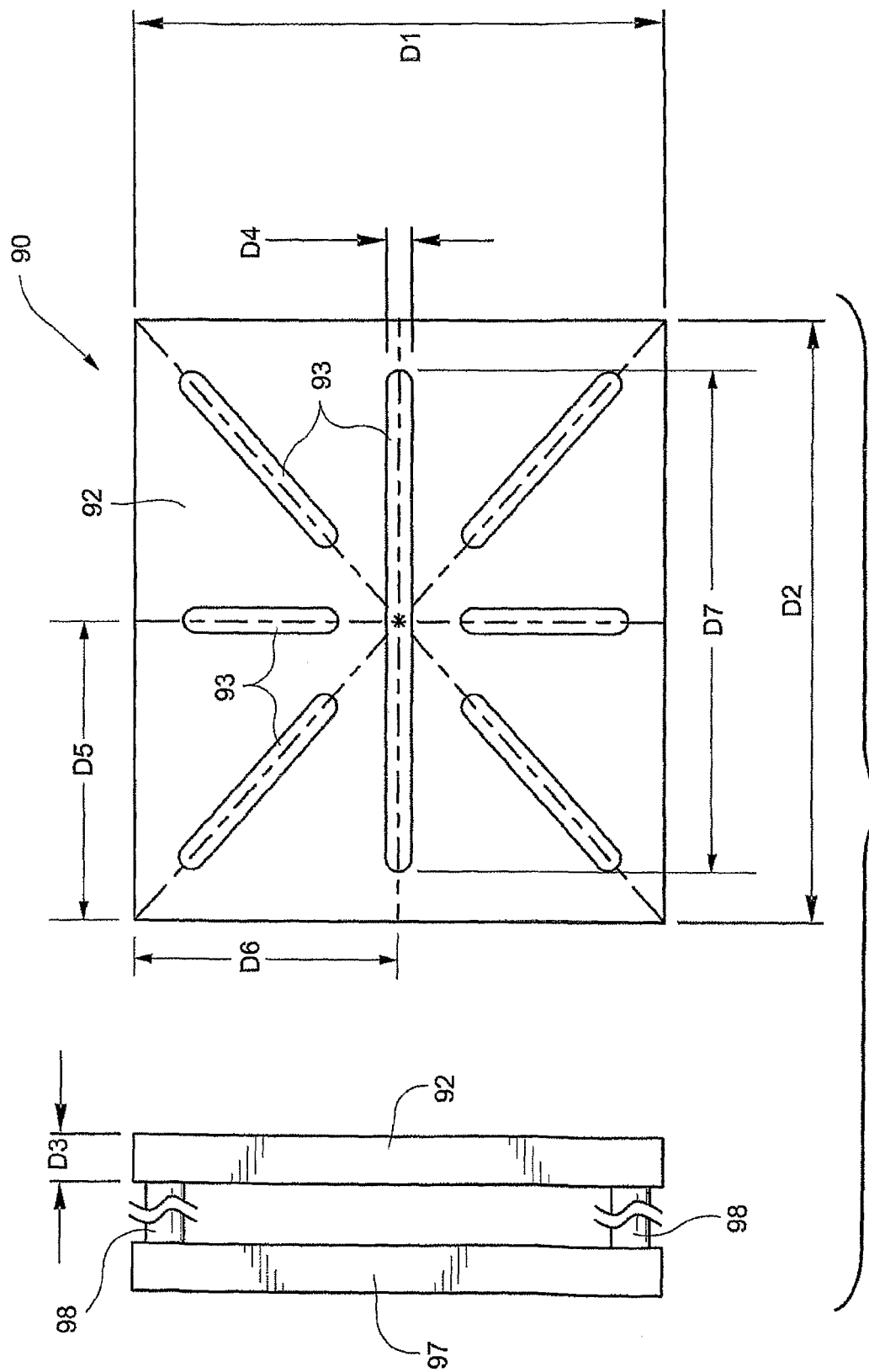

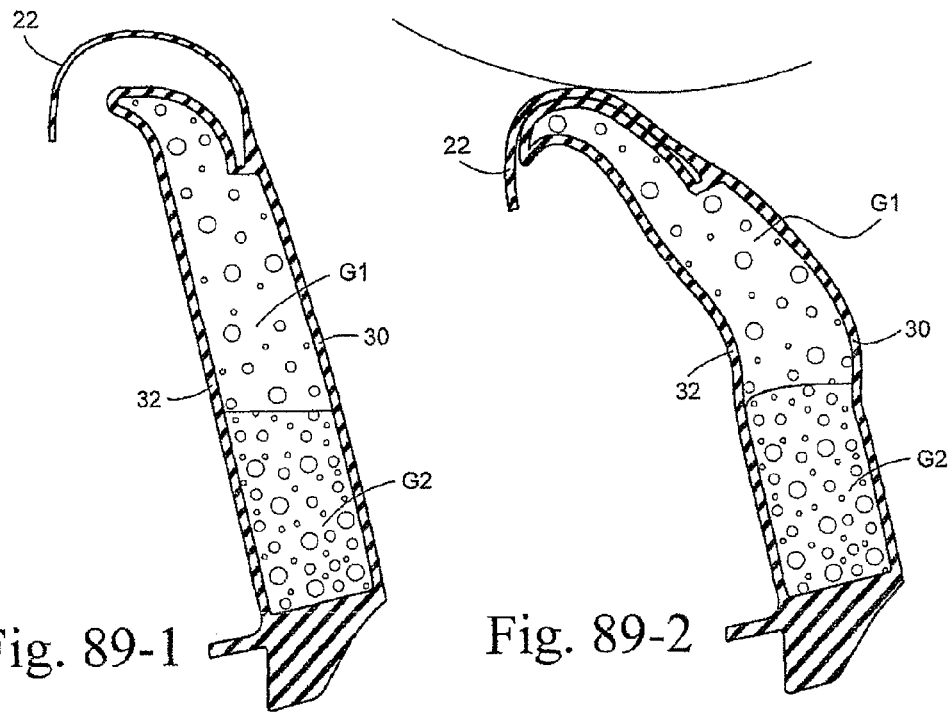
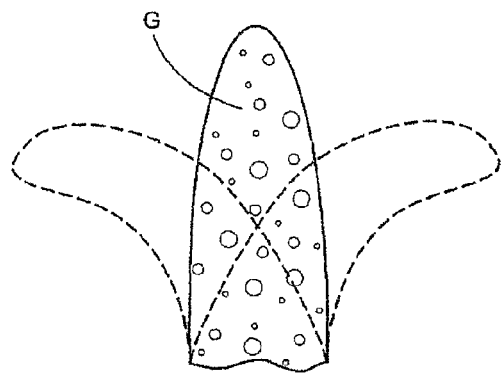
Fig. 90
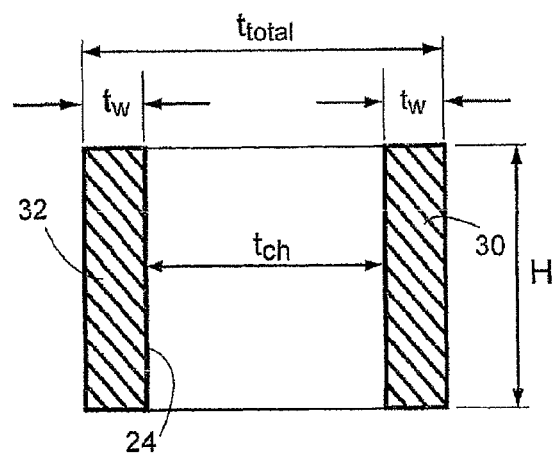
Fig. 91
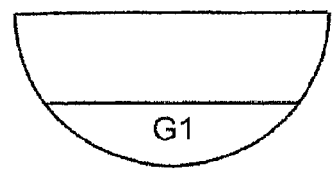
Fig. 92-1
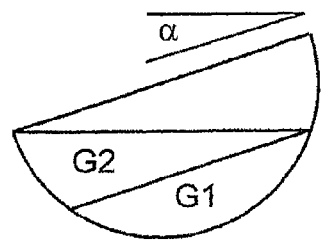
Fig. 92-2

FLEXIBLE STRUCTURE FOR MASK, AND METHOD AND APPARATUS FOR EVALUATING PERFORMANCE OF A MASK IN USE

CROSS-REFERENCE TO APPLICATION

This application is the U.S. national phase of International Application No. PCT/AU2009/000682, filed May 29, 2009, which designated the U.S. and is a Continuation-in-Part of PCT/AU2008/001711, filed Nov. 17, 2008, and claims the benefit of AU 2008902720, filed May 29, 2008, AU 2008903294, filed Jun. 27, 2008, EP 08160921.6, filed Jul. 22, 2008, AU 2009900323, filed Jan. 30, 2009, and AU 2009902153, filed May 14, 2009, each of which is incorporated herein by reference in its entirety.

FIELD OF THE INVENTION

The present technology relates to a respiratory mask for delivery of air or breathable gas at positive pressure. In particular, the present technology relates to a respiratory mask of improved comfort and or fit range compared to prior art masks, as well as methods and apparatus for measuring or evaluating the performance of such masks.

1. BACKGROUND OF THE INVENTION

The use of Nasal Continuous Positive Airway Pressure (nasal CPAP) to treat Sleep Disordered Breathing (SDB) was pioneered by Sullivan, e.g., see U.S. Pat. No. 4,944,310. Apparatus for providing nasal CPAP typically comprises a source of air at positive pressure (for example provided by a blower or flow generator at 3-30 cmH2O), some form of patient interface or respiratory mask system (for example a nasal or full-face mask system), and an air delivery tube.

Respiratory mask systems typically include some form of cushioning element, a sealing element and some form of stabilizing element (for example, a frame and headgear). The cushioning and sealing elements may be formed in one piece and collectively referred to as a "cushion", or more than one piece, or may be separate structures. Cushioning and sealing elements may be formed from different portions of a single structure. Headgear may include an assembly of soft, flexible, elastic straps. Headgear may be constructed from a composite material such as foam and fabric, and may include a stiffening element.

The frame may be a rigid or semi-rigid structure that allows for the connection of the cushion, headgear and air delivery tube. The frame can be made of a hard material such as polycarbonate, a semi-rigid material such as a high durometer silicone (e.g. 80 Type A durometer) or polypropylene, or various other materials alone or in combination, such as a combination of a rigid frame skeleton and a soft chamber defining material.

Much mask design effort is directed towards improving the comfort of masks, which among other benefits, can help lead to better compliance and efficacy of therapy. A range of commercial mask systems are known including the MIRAGE mask, manufactured by ResMed Limited.

Also, the performance or properties of a mask may be measured or evaluated using different tests. However, the accuracy of any test may depend on one or more parameters of the sample and/or equipment. Therefore, tests and testing equipment are desired to reduce or eliminate testing variances.

2. SUMMARY OF THE INVENTION

A first aspect of the present technology is a comfortable cushion for use as part of a respiratory mask assembly, the assembly is useful in treatment of respiratory disorders such as sleep disordered breathing. A second aspect of the present technology is one or more soft materials suitable for use in a cushion for a respiratory mask. A third aspect of the technology is a method of constructing a cushion for a respiratory mask, including methods of manufacturing one or more cushion chambers, and filling the chambers with one or more soft materials. A fourth aspect of the technology is a headgear system incorporating a soft material. A fifth aspect of the technology is a method of comparing different masks that simulates in-use performance of the mask. One or more aspects may be combined.

A comfortable cushion in accordance with the first aspect of the present technology is suitable for wearing for long periods of time with improved comfort for a patient. The cushion performance is a function of the properties of the materials used in its construction and their configuration. The cushion is constructed to have certain performance characteristics that enhance comfort and or simply adjustment while maintaining seal. In one form of cushion in accordance with the technology, the cushion is constructed and arranged to provide improved desensitivity to adjustments in headgear tension so that small changes in headgear tension do not lead to large changes in force on the face over a range of tension forces.

A soft material in accordance with the second aspect of the technology may be a gel, or gel-like material. The material may be characterised by one or more properties including Young's Modulus of Elasticity (e.g., 2–5 kPa, 3–4 kPa), Indentation resistance, Viscoelasticity and Rate of Return (e.g., between 1 and 5 seconds). Where more than one soft material is used, the different soft materials may have different properties, such as different indentation resistances and/or different rates of return.

A method of constructing a cushion in accordance with the third aspect of the present technology includes moulding a cushion, for example in a Liquid Silicone Rubber (LSR) moulding process. The cushion may be moulded to include one or more chambers in different regions of the cushion, such as a nasal bridge region, a cheek region or a lip region. The one or more chambers may be filled with one or more soft materials, such as gel, or gel-like material. In another form of the technology, a chamber may be partly or completely filled with a low durometer silicone, or other rubber material. The one or more chambers may be filled to different levels and/or at different angles in different regions of the cushion. The cushion may be constructed to have different cross-sections in different regions. The cushion may define wall regions. The cushion wall regions may have straight shapes, externally convex shapes, or externally concave shapes. The cushion wall regions may have different heights in different regions. The cushion may be moulded to include a thin flexible facial flap that will readily conform to irregularities in the facial contour, and which readily responds to system pressure acting on its underside to urge it into tight sealing engagement with the face.

A fourth aspect of the present technology is one or more mask components, such as forehead supports and headgear straps incorporating pockets filled with a soft material, such as a gel.

A test method in accordance with a fifth aspect of the present technology simulates cushion performance in use. In accordance with this test method, force-deflection curves may be constructed for different regions of masks, such as nasal bridge region, cheek region and lip or chin regions. The method may include providing a support jig having a plurality of adjustable support bars, adjusting one or more of the support bars to support the respiratory mask such that the flexible structure faces a testing machine that allows measurement of force as a function of indentation, positioning an indenter of the testing machine into engagement with a selected region of the flexible structure, and operating the testing machine to deflect the selected region of the cushion with the indenter.

Another aspect of the invention relates to a respiratory mask including a flexible structure adapted to engage a patient's face. The flexible structure includes a chamber filled with at least a first gel. The flexible structure is adapted to deflect upon engagement with a testing machine having an indenter that allows measurement of applied force as a function of indentation. The flexible structure is associated with a force of less than about 1 N at an indentation of about 5 mm.

Another aspect of the invention relates to a method for testing in-situ properties of a respiratory mask having a flexible structure including at least a first gel. The method includes providing a support jig having a plurality of adjustable support bar, adjusting one or more of the support bars to support the respiratory mask such that the flexible structure faces a testing machine that allows measurement of force as a function of indentation, positioning an indenter of the testing machine into engagement with a selected region of the flexible structure, and operating the testing machine to deflect the selected region of the flexible structure with the indenter.

Another aspect of the invention relates to a respiratory mask including a frame and a flexible structure provided to the frame and adapted to engage a patient's face. The flexible structure includes a chamber filled with a first gel and a second gel that is relatively harder than the first gel. A ratio of height of the first gel to the second gel in a lip region is in the range of about 0.25 to about 0.6.

Another aspect of the invention relates to a flexible structure for a respiratory mask including a chamber filled with at least a first gel. The flexible structure has cone penetration hardness between about 200 and 350 cone penetrations.

Another aspect of the invention relates to a cushion for a respiratory mask assembly. The cushion including a liquid silicone rubber (LSR) moulded structure having at least one chamber therein. At least one gel filling material has an indentation resistance less than can be measured on a Type OOO scale. The gel filling material is located within the at least one chamber.

Another aspect of the invention relates to a mask assembly including a frame and a cushion provided to the frame. The cushion includes an elastic molded structure defining at least one chamber therein. A gel filling material is provided to the chamber. The gel material has a hardness of more than 200 cone penetrations.

Another aspect of the invention relates to a mask assembly including a frame and a cushion provided to the frame. The cushion includes a structure defining at least one chamber therein. A filling material (e.g., gel) is provided to the chamber. The mask may include one or more of the following properties/features: the gel material may have a hardness of more than 200 cone penetrations, the gel material may comprise silicone gel, the gel material may have a visco-elastic rate of return of at least 1 second, the chamber defining structure may comprise an elastic material, e.g., liquid silicone rubber, the chamber defining structure may include a first portion that defines a face contacting surface to contact the patient and inner and outer side walls of the chamber, and a second portion that defines a cap opposite the face contacting surface and joined to the frame, the cushion may include a side wall which having a thickness corresponding to the combined thickness of the chamber and the inner and outer side walls of the chamber, the chamber may include side walls each having a thickness of at least 0.4 to 0.6 mm, the cushion may have side walls that are curved or angled inwardly towards a breathing cavity in communication with an airway of the patient, a sealing flap provided in covering relation to the chamber, a sealing flap having a proximal end extending from an external side wall surface of the cushion, a sealing flap may be formed in one piece with the cushion, a sealing flap may have a shape that generally corresponds to a shape of an exterior surface of the chamber oriented towards the patient's face, a shape of the sealing flap may be generally convex as applied to the patient's face, a length of the sealing flap from its proximal end to its distal end is greater than a width of a side wall of the cushion, the sealing flap may have a thickness of less than about 0.5 mm, e.g., 0.35 mm, the sealing flap may include a frosted surface to contact the patient's face, the sealing flap may include a molded bead provided adjacent the distal end thereof, the cushion may not include any welded seams, the cushion may include at least two regions with different properties, a nasal bridge region of the cushion may have relatively more visco-elastic properties and a cheek region of the cushion may have relatively more elastomeric properties, the nasal bridge region may not include the gel filling material, the nasal bridge region may comprise a relatively stiff silicone material, the gel filling material may include a relatively softer layer positioned relatively closer to the patient's face and a relatively harder layer positioned relatively further away from the patient's face, the relatively harder layer may serve to support the relatively softer layer such that when the cushion is fitted to the patient, a side wall of the cushion is controlled to promote deliberate and generally predictable compression, bending and/or rolling of the side wall of the cushion towards a breathing cavity in communication with an airway of the patient, the chamber may have a thickness of about 6 to 8 mm, and/or a height of the chamber may be greater than 20, e.g., 20-30, in a cheek region and/or greater than 20, e.g., 20-25, in a lip/chin region.

Other aspects, features, and advantages of this invention will become apparent from the following detailed description when taken in conjunction with the accompanying drawings, which are a part of this disclosure and which illustrate, by way of example, principles of this invention.

3. BRIEF DESCRIPTION OF THE DRAWINGS

The accompanying drawings facilitate an understanding of the various embodiments of the invention. In such drawings:

FIG. 12-1 shows test results for load versus indentation in the nasal bridge region using a first test method according to an embodiment of the present invention;

FIG. 13-1 shows test results for load versus indentation in the cheek region using a first test method according to an embodiment of the present invention;

FIG. 14-1 shows test results for load versus indentation in the lip region using a first test method according to an embodiment of the present invention;

FIG. 12-2 shows test results for load versus indentation in the nasal bridge region using a second test method according to an embodiment of the present invention;

FIG. 13-2 shows test results for load versus indentation in the cheek region using a second test method according to an embodiment of the present invention;

FIG. 14-2 shows test results for load versus indentation in the lip region using a second test method according to an embodiment of the present invention;

FIGS. 47-1 to 47-6 are sequential side views showing a flexible structure according to an embodiment of the present invention being compressed in use;

Figure 1:
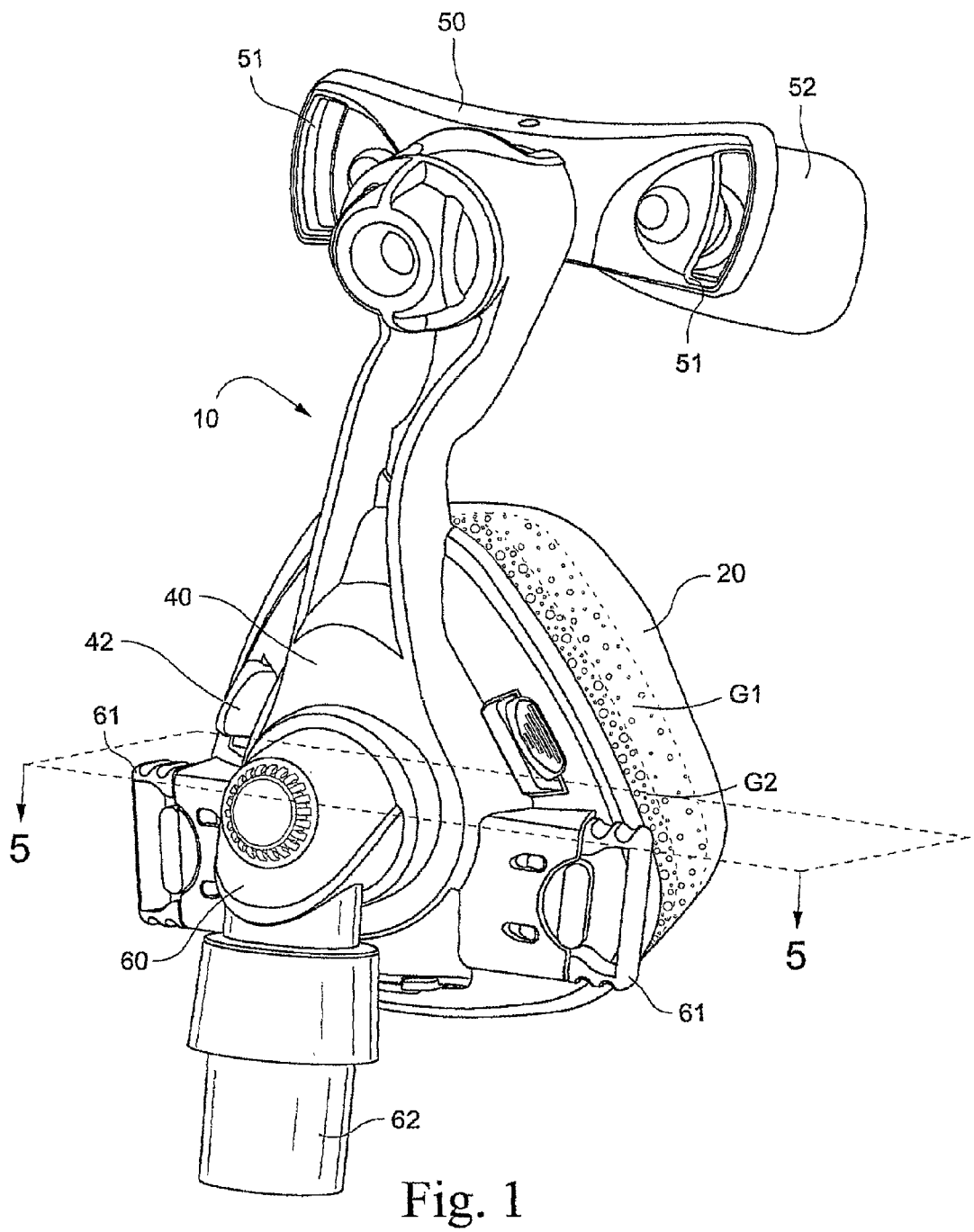
FIG. 1 is a perspective view of a nasal mask assembly including a flexible structure according to an embodiment of the present invention.
Figure 2:
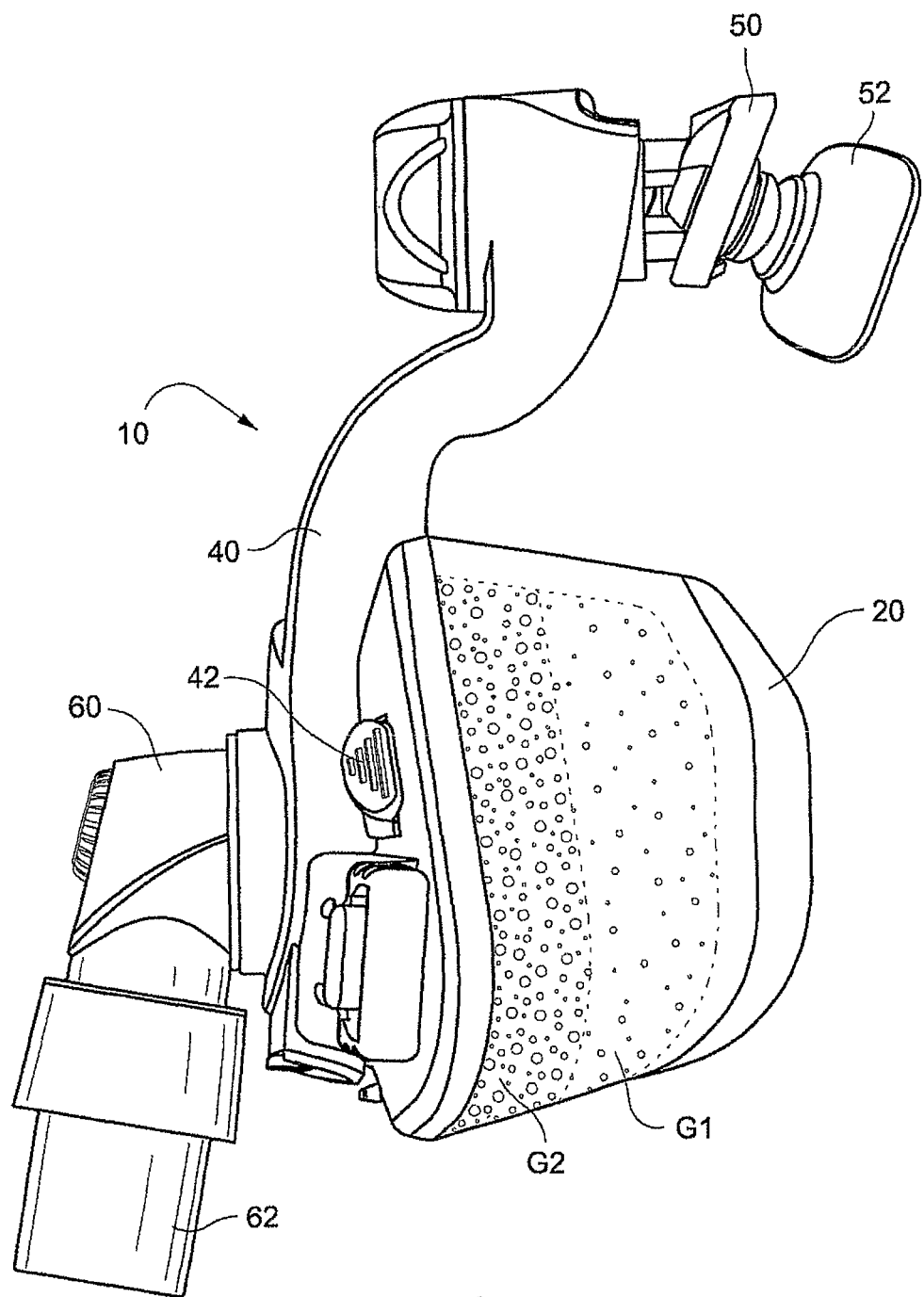
FIG. 2 is a side view of the nasal mask assembly of FIG. 1.
Figure 3:
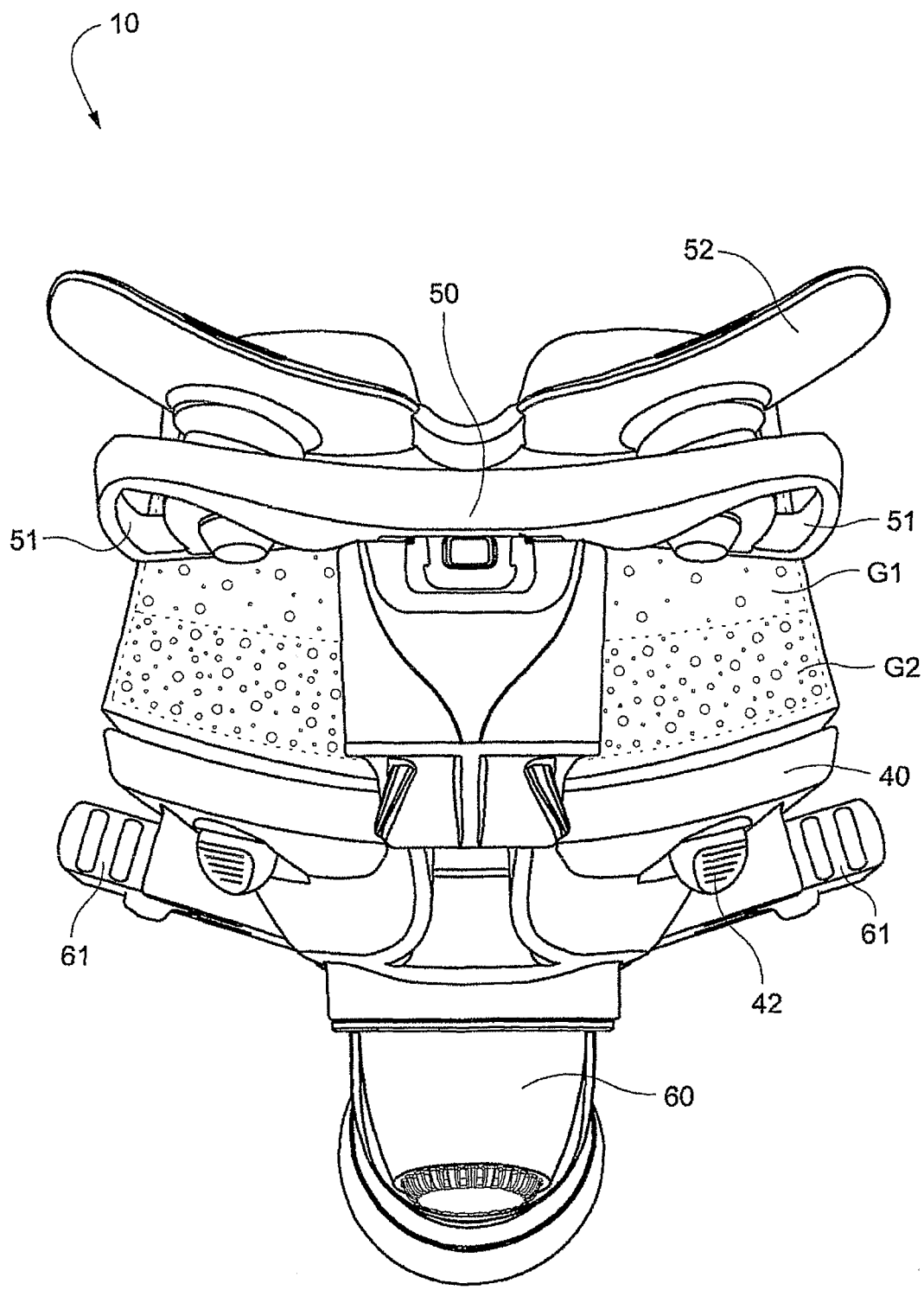
FIG. 3 is a top view of the nasal mask assembly of FIG. 1.
Figure 62:
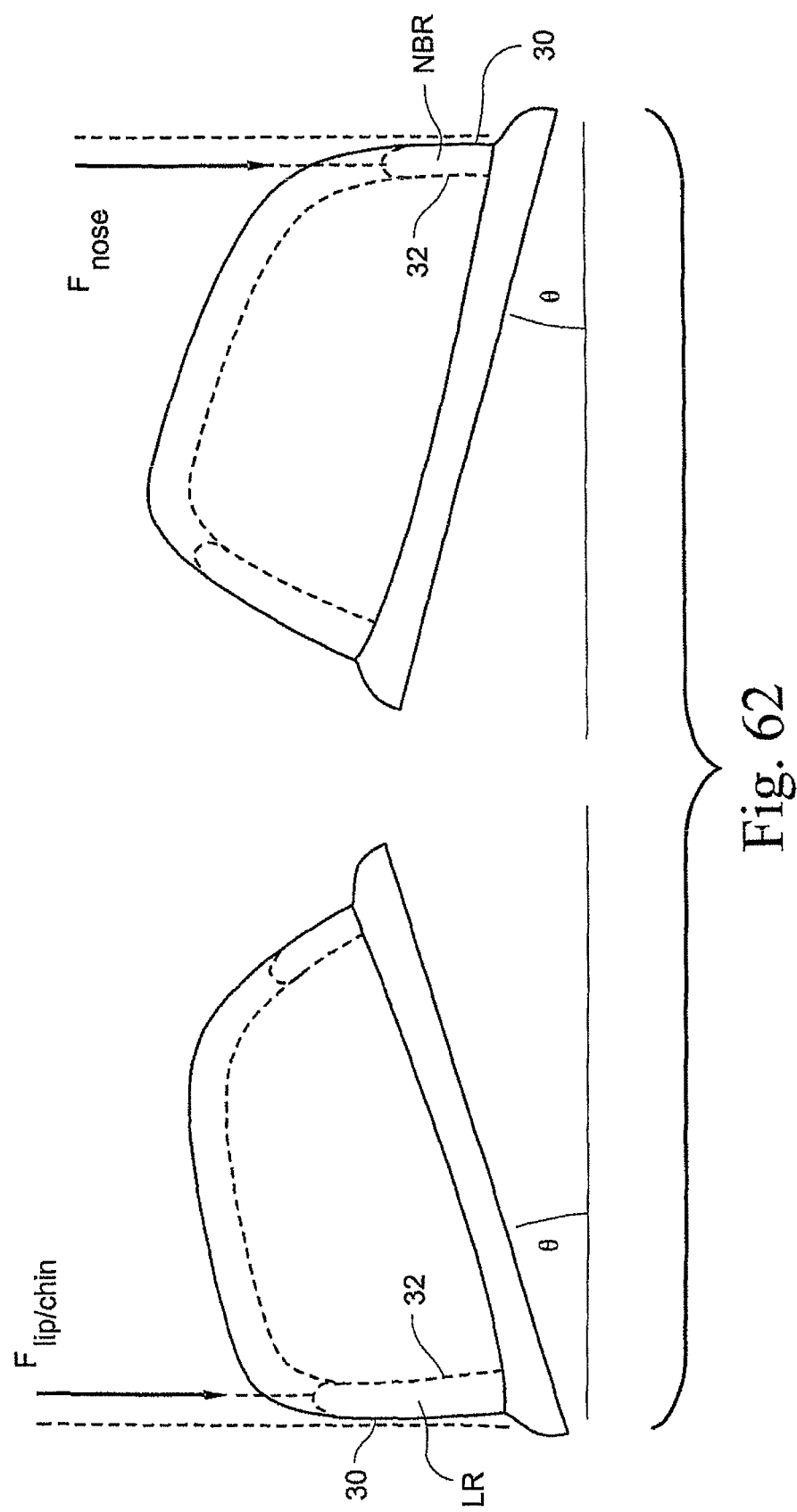
Figure 63:
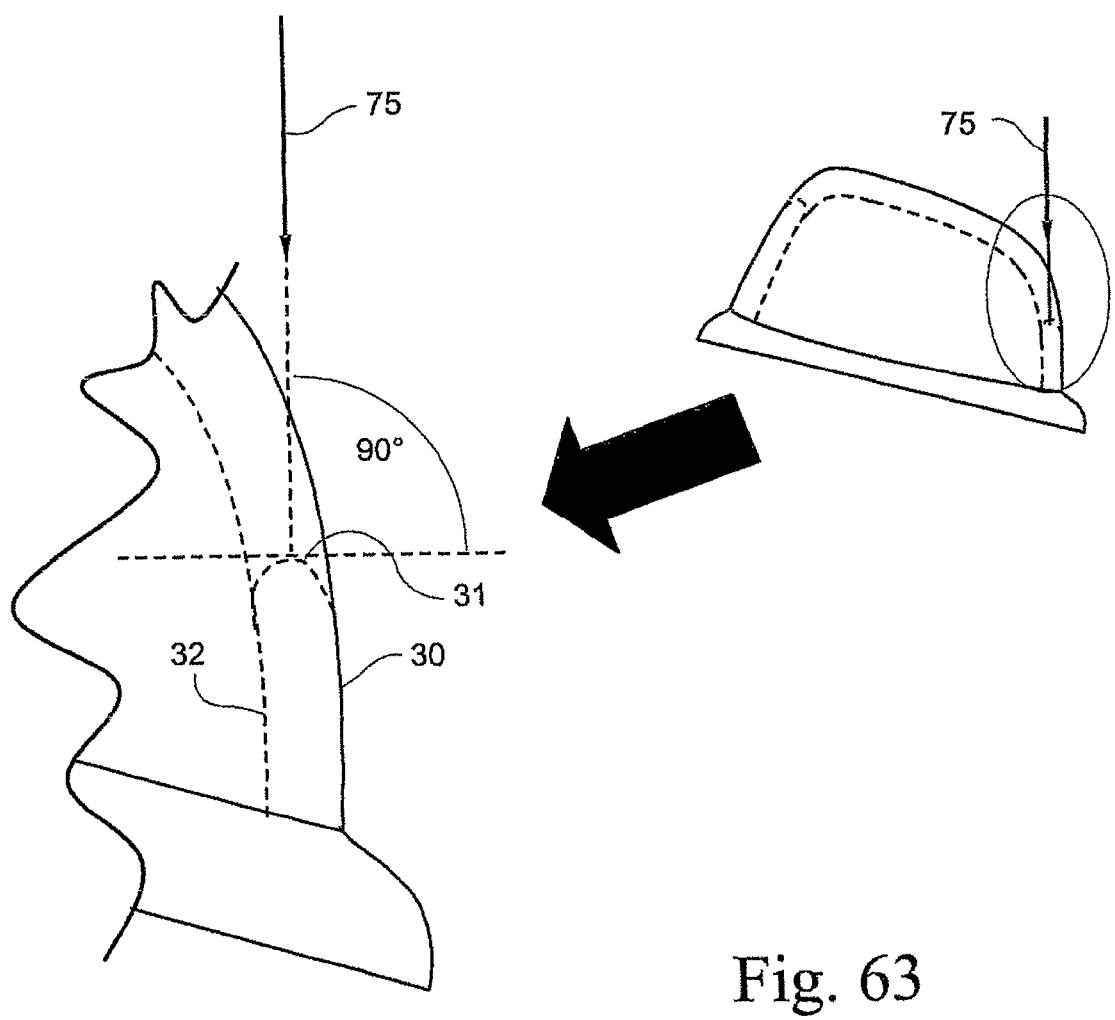
Figure 64:
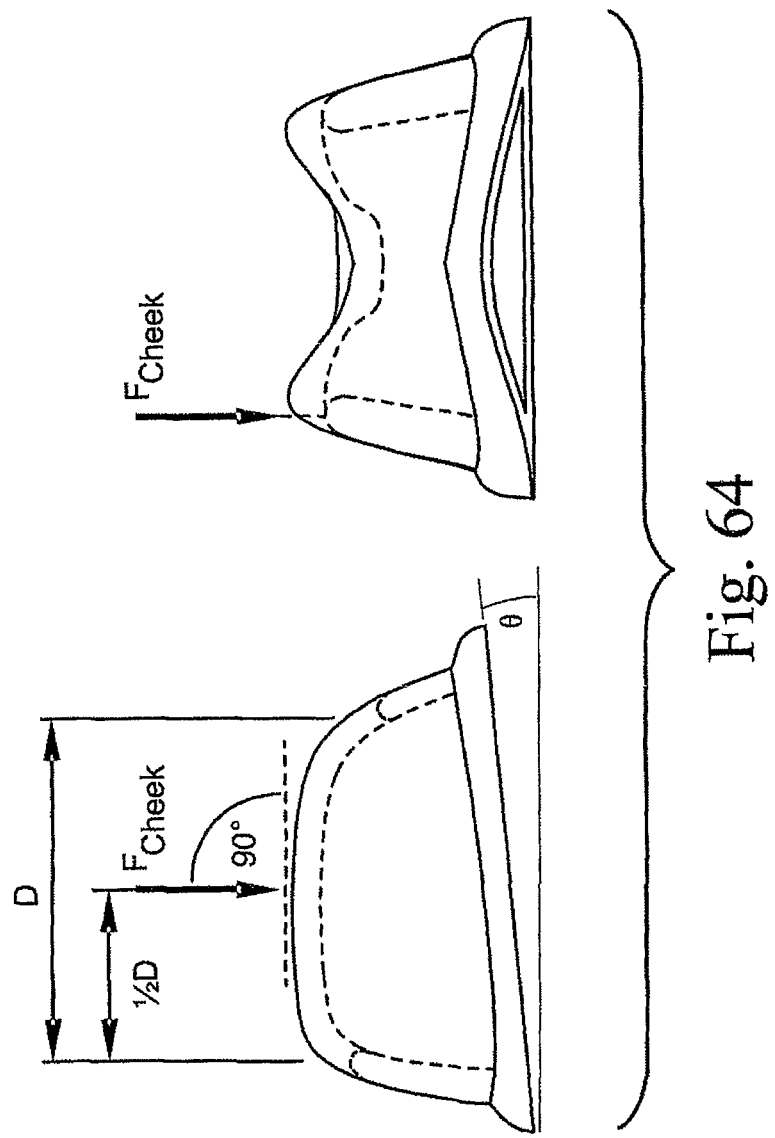
Figure 65:
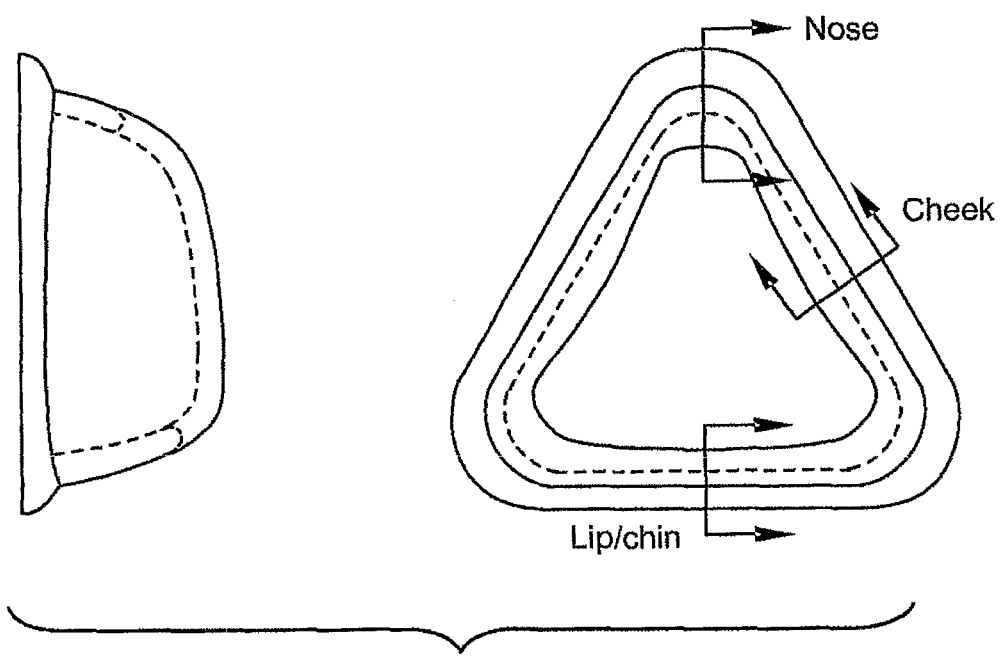
Figure 67:
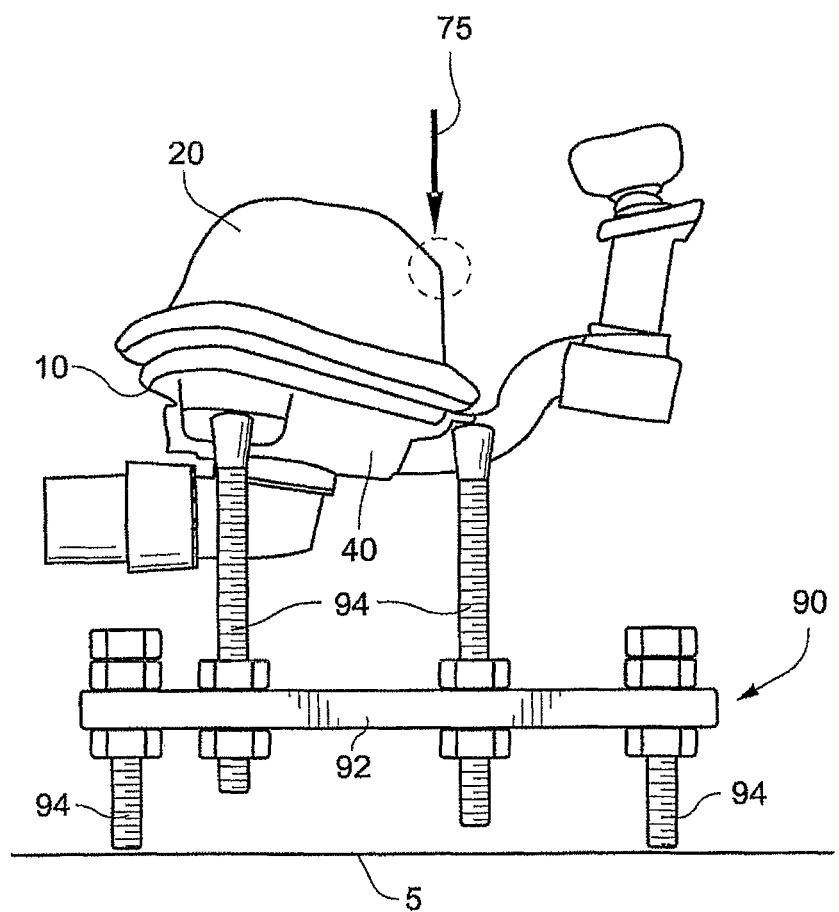
Figure 68:
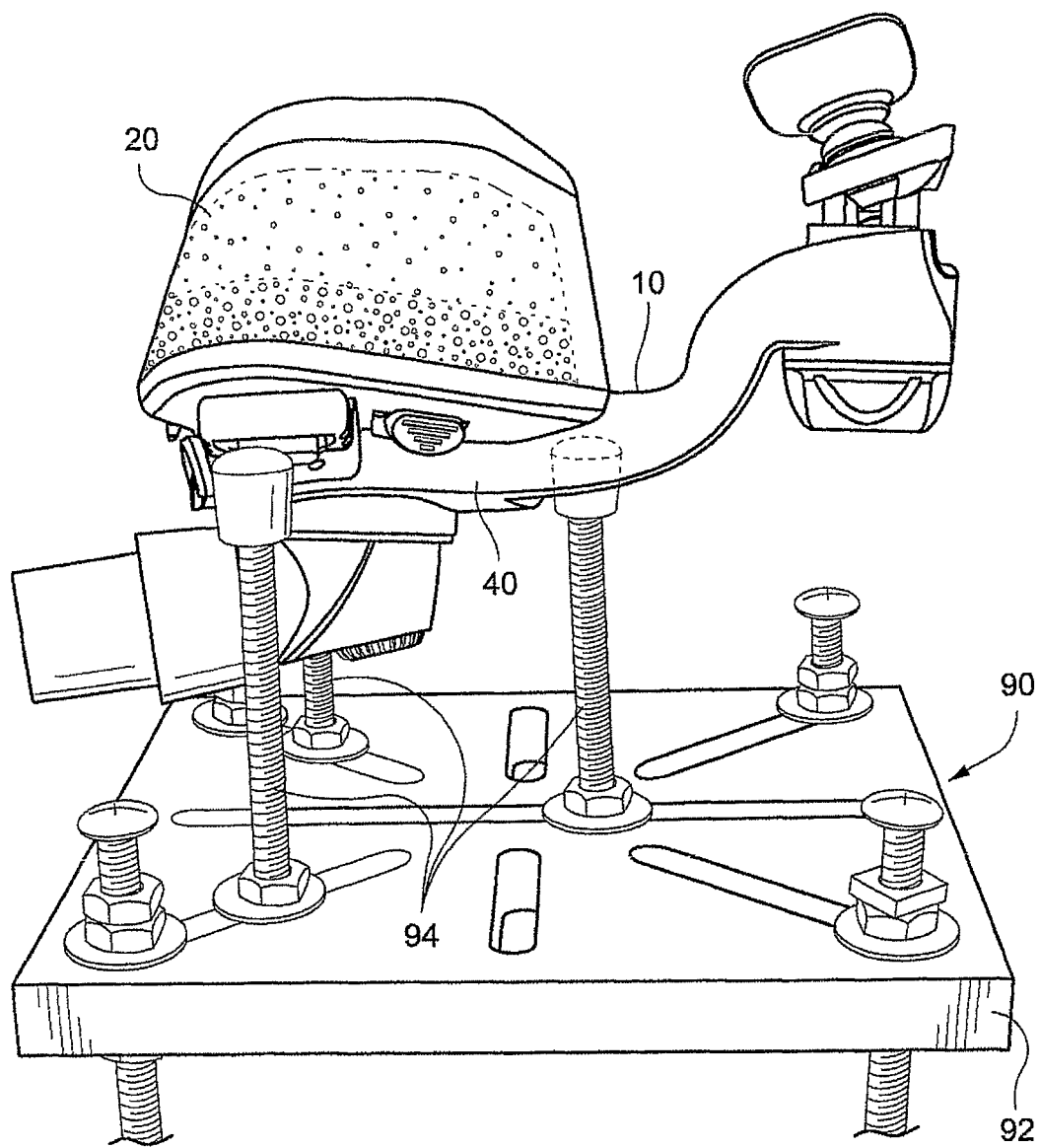
Figure 69:
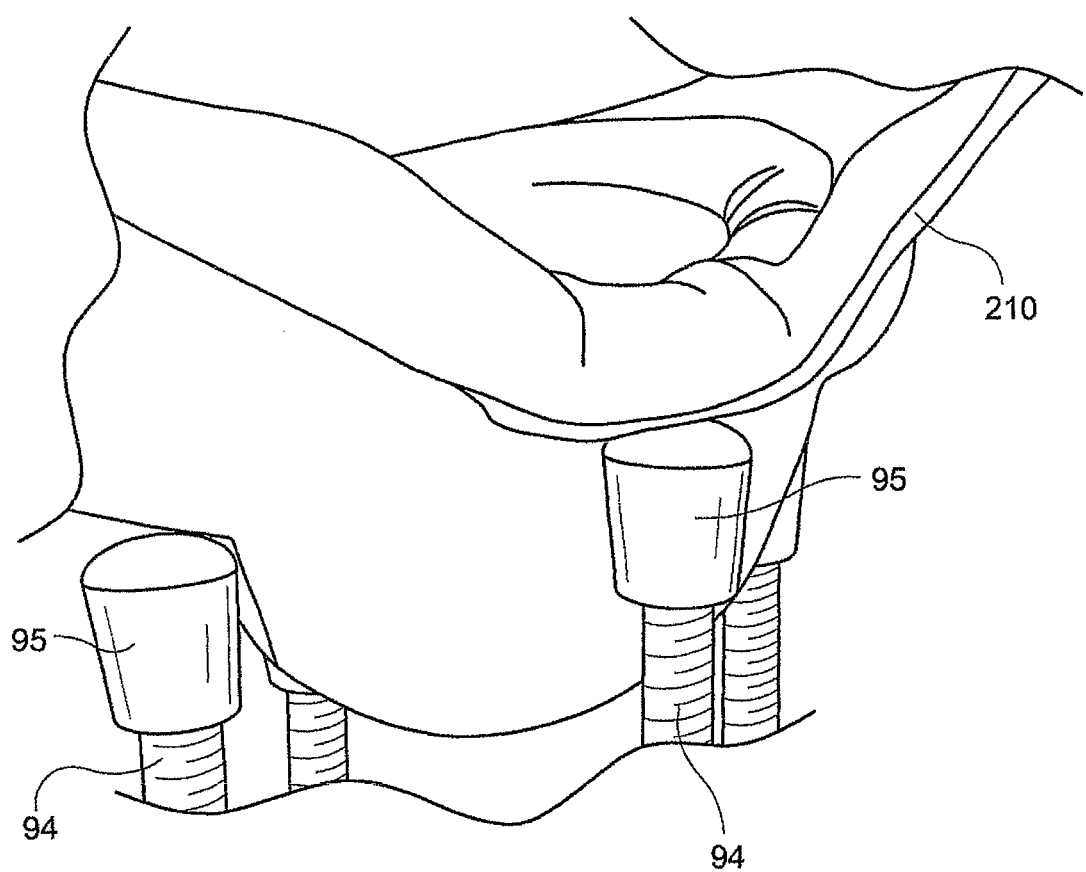
Figure 70:
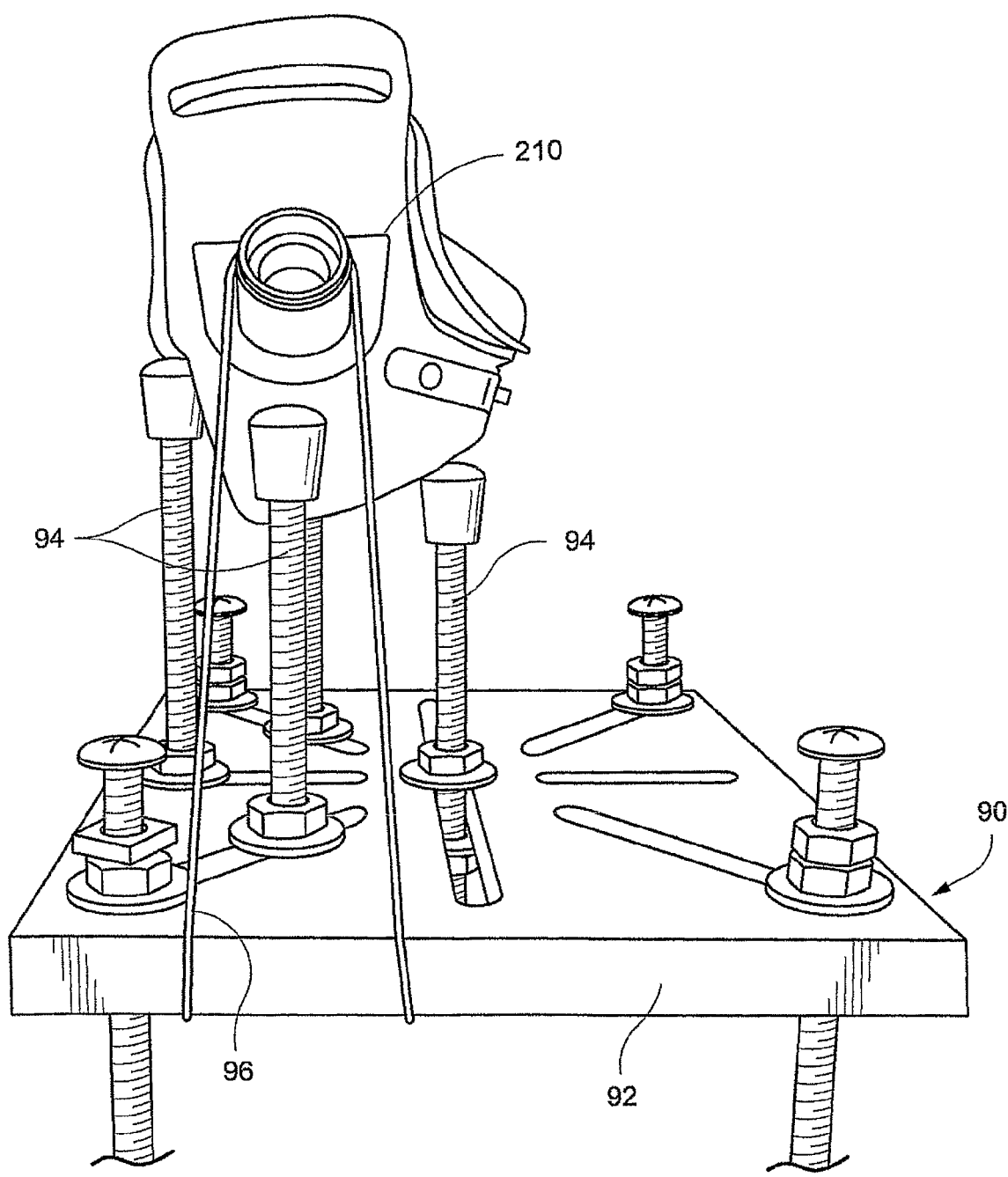
Figure 71:
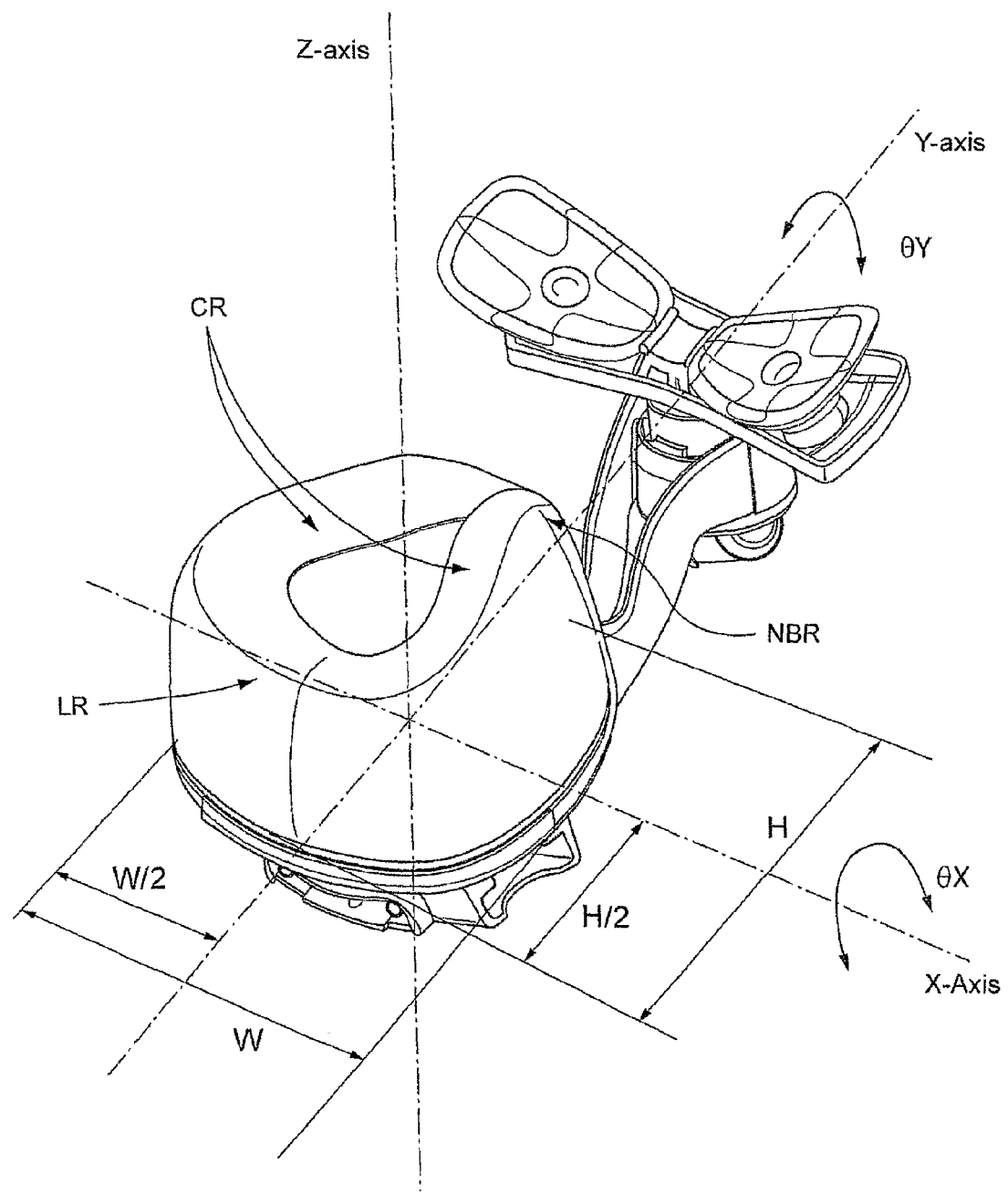
Figure 72:
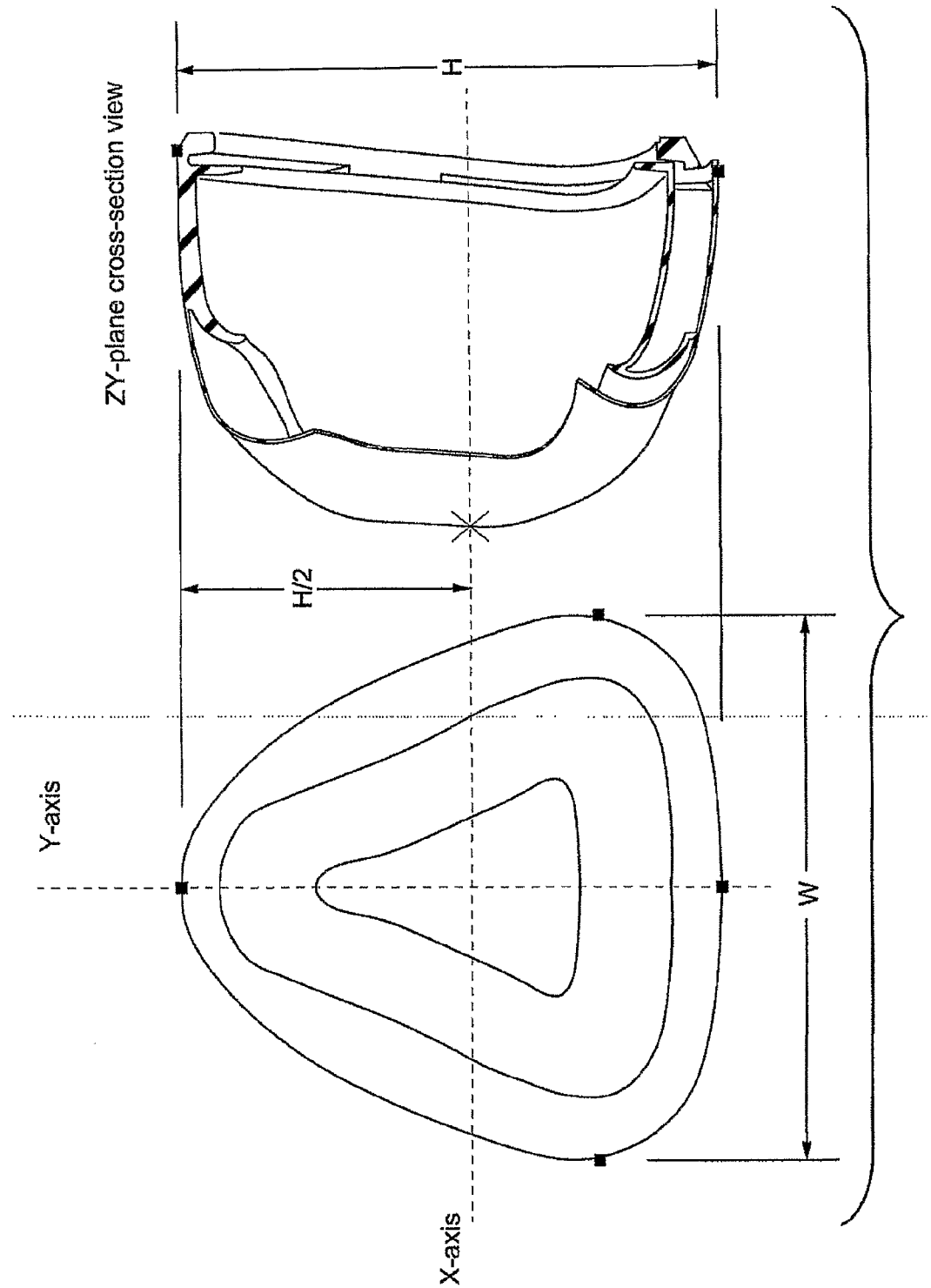
Figure 73:
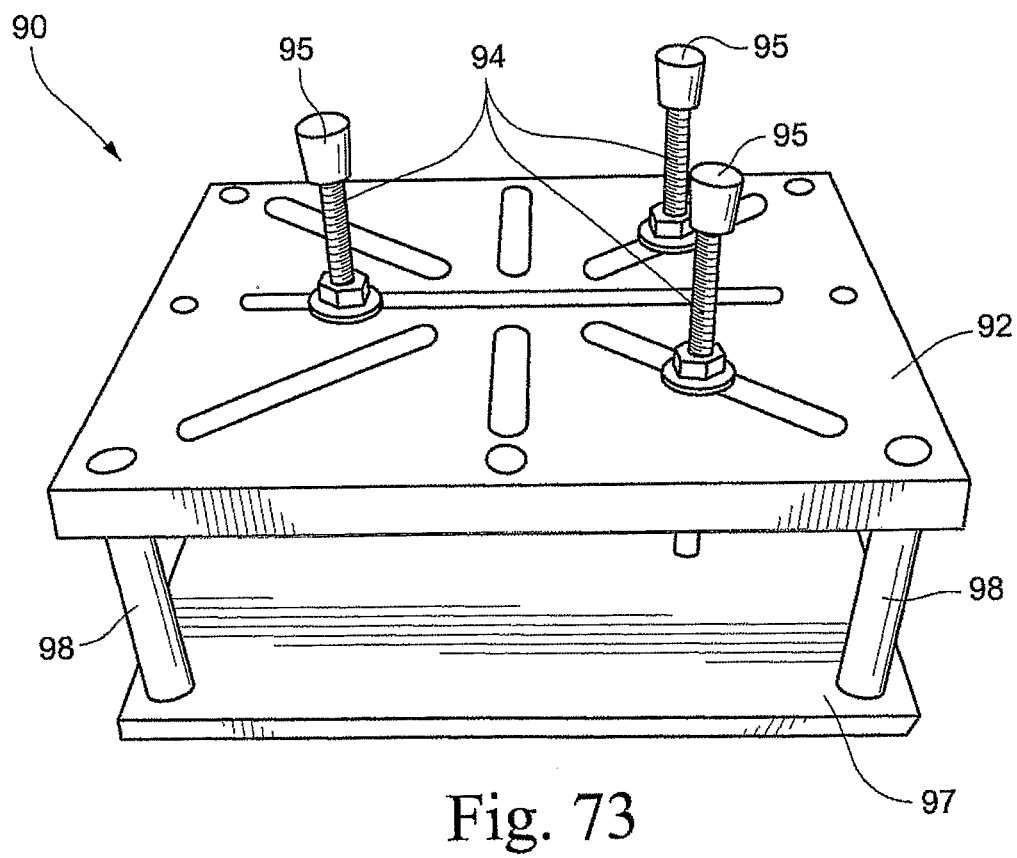
Figures 1, 74:
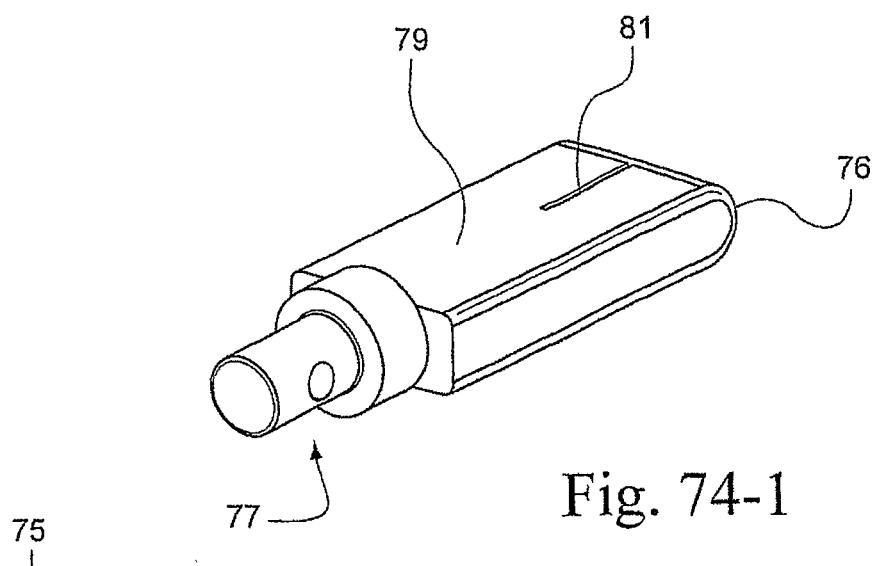
Figures 2, 74:
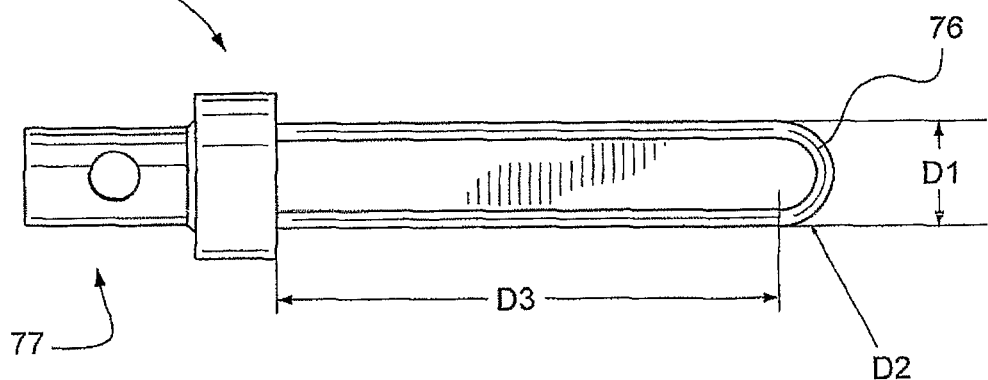
Figures 3, 74:
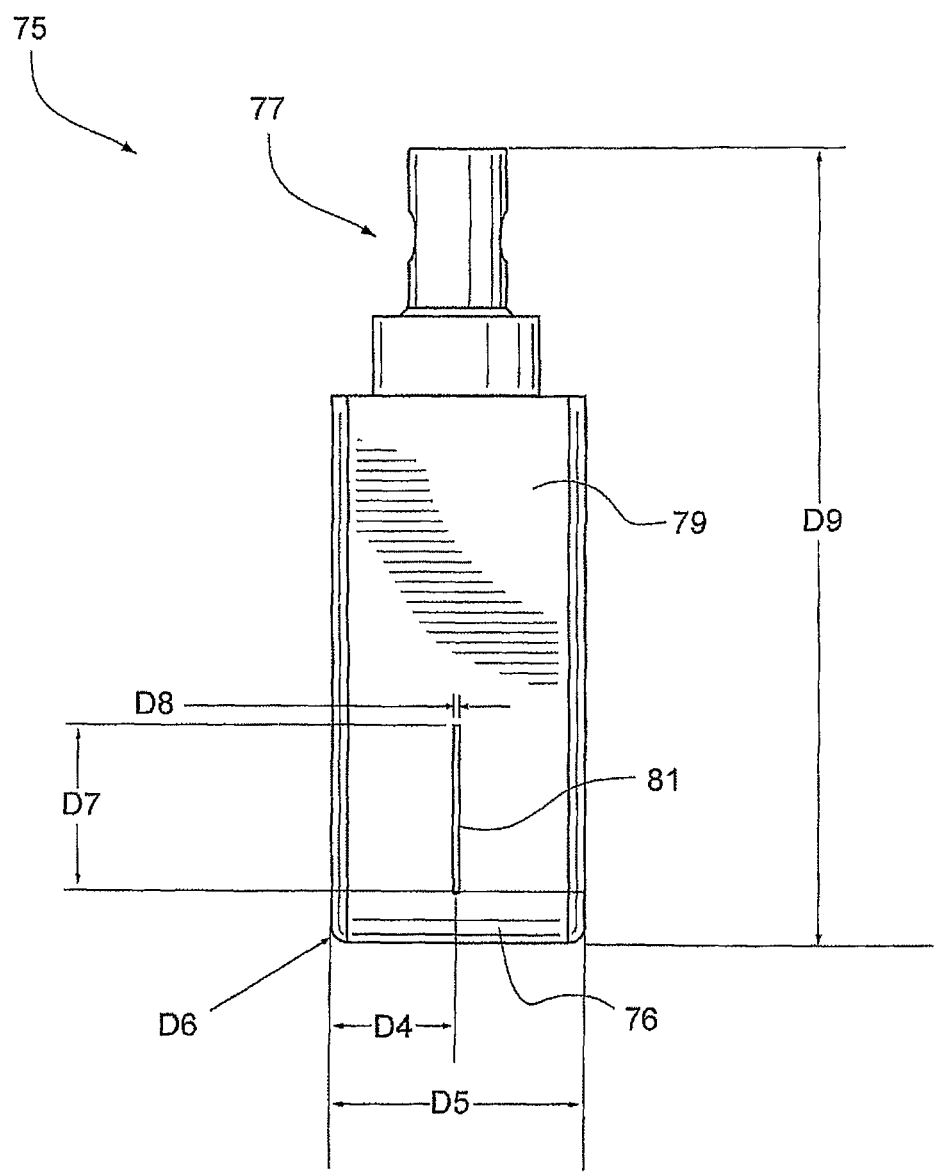
Figure 75:
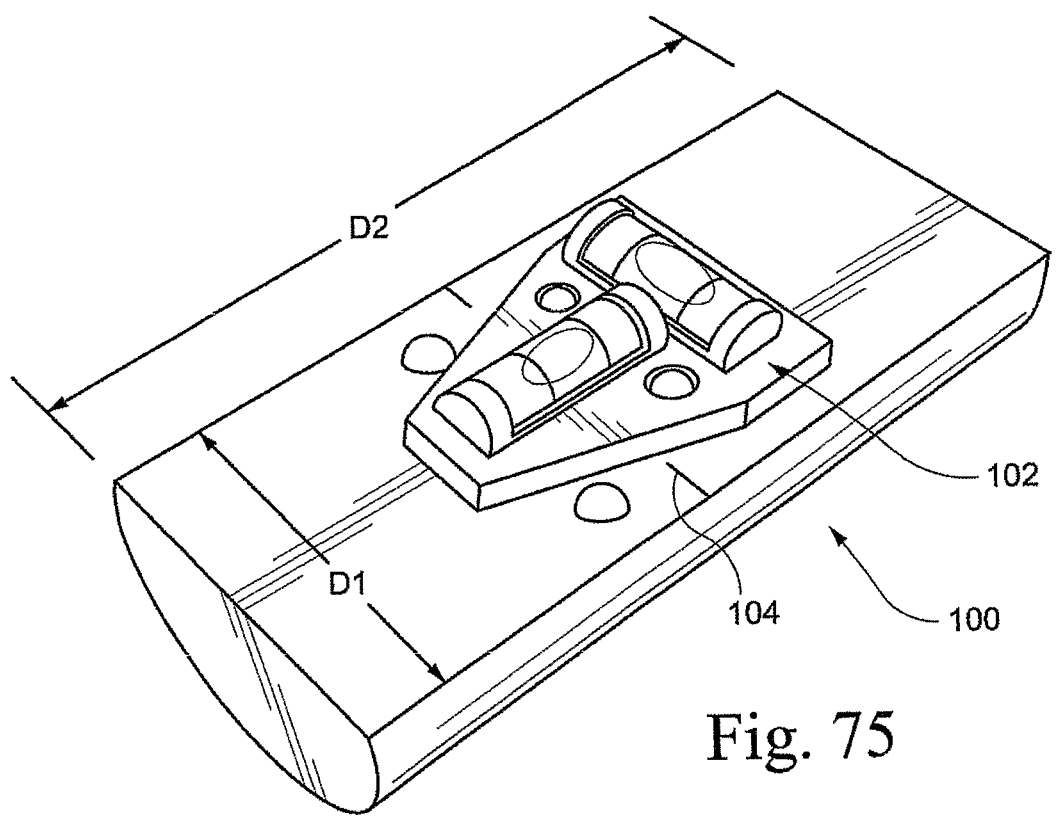
Figure 76:
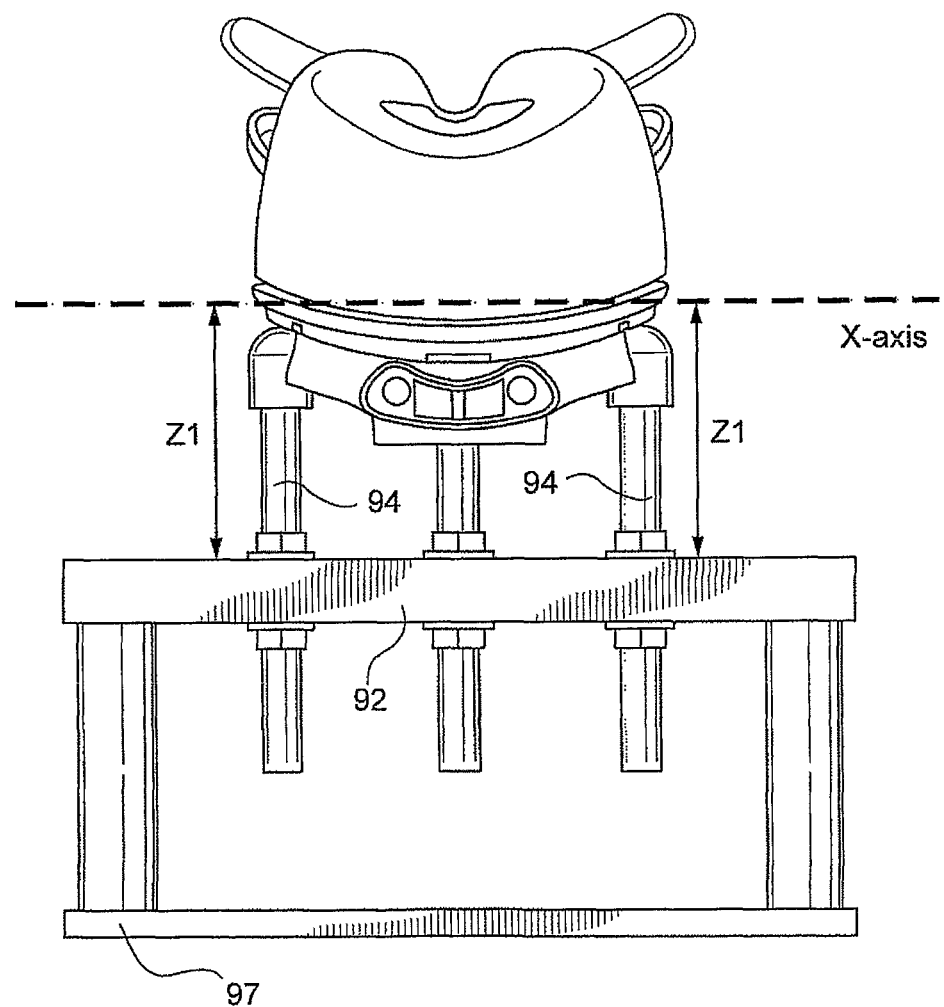
Figure 77:
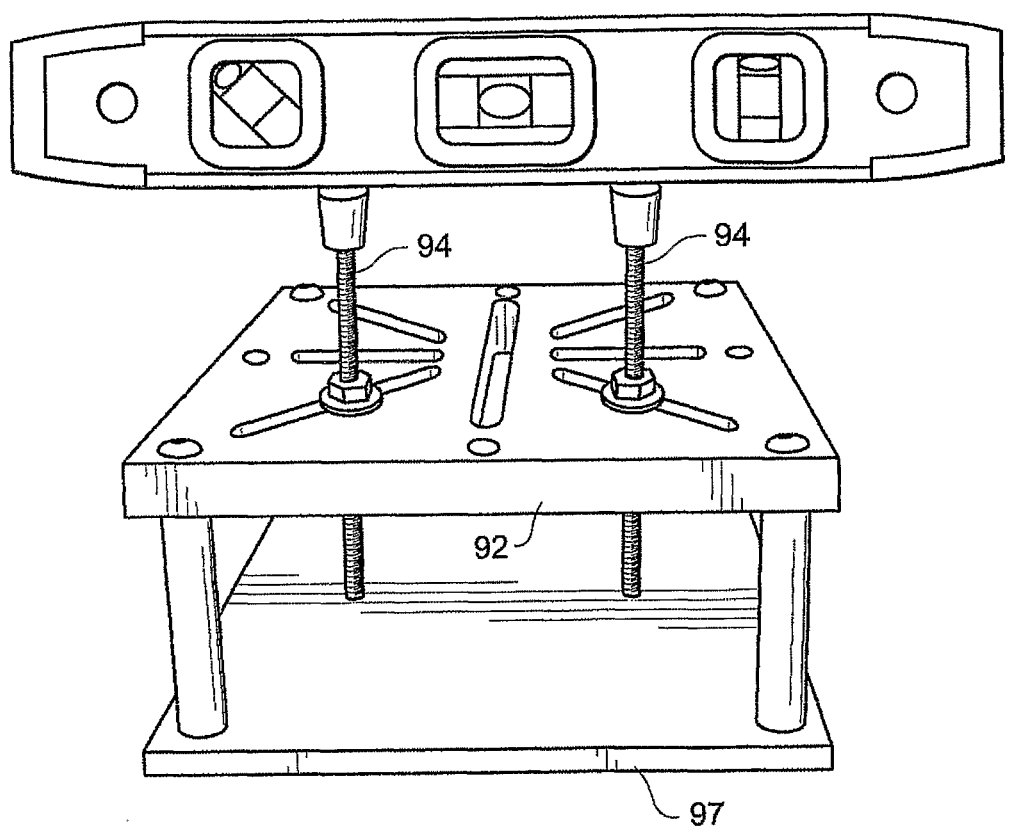
Figure 78:
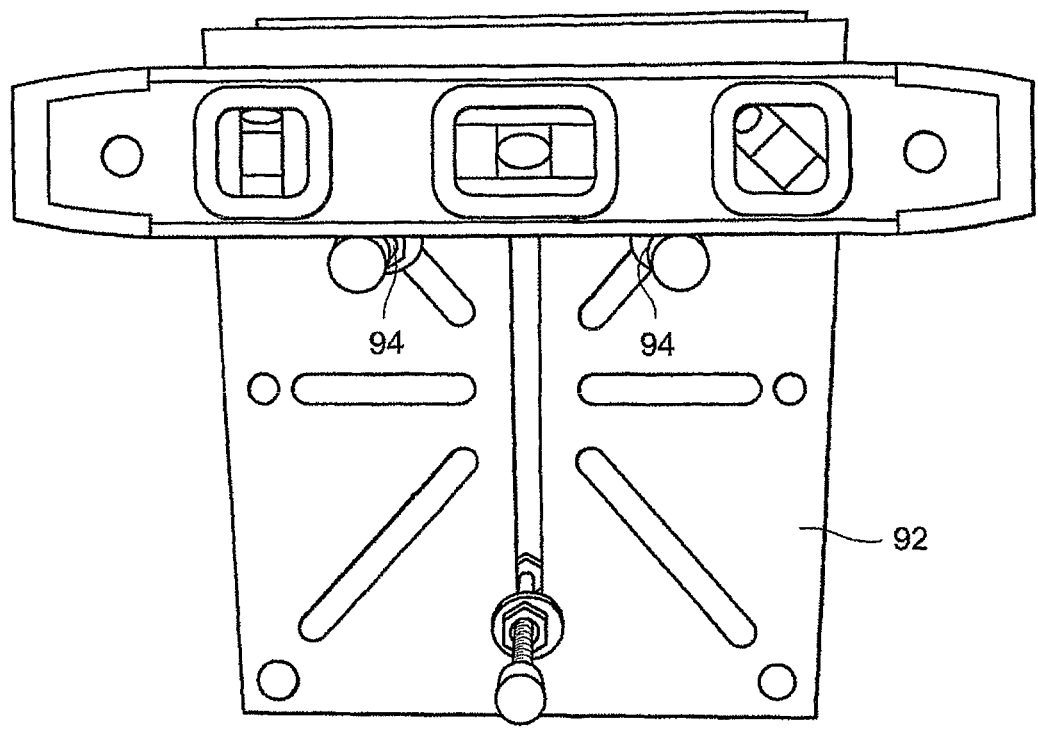
Figure 79:
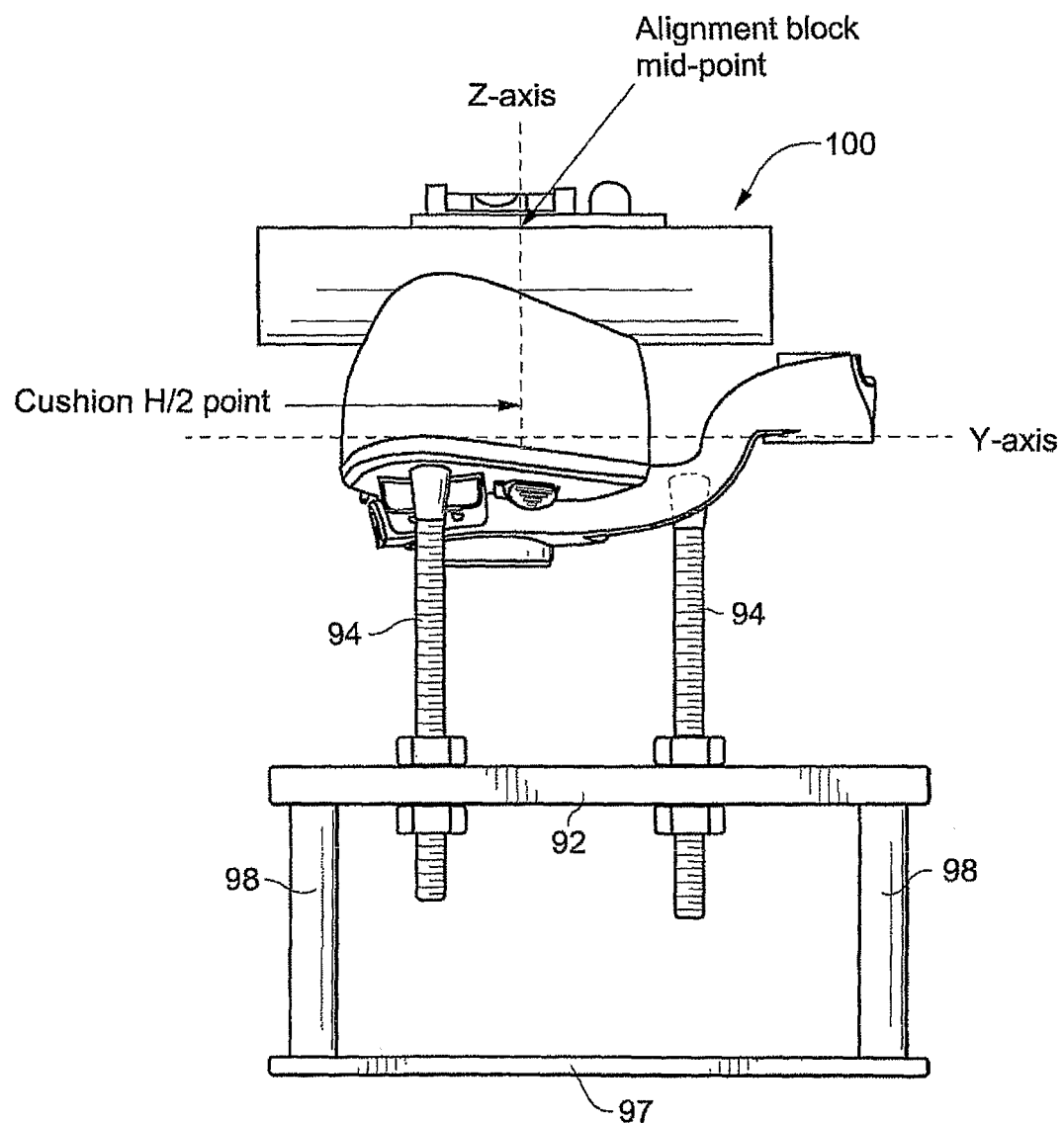
Figure 80:
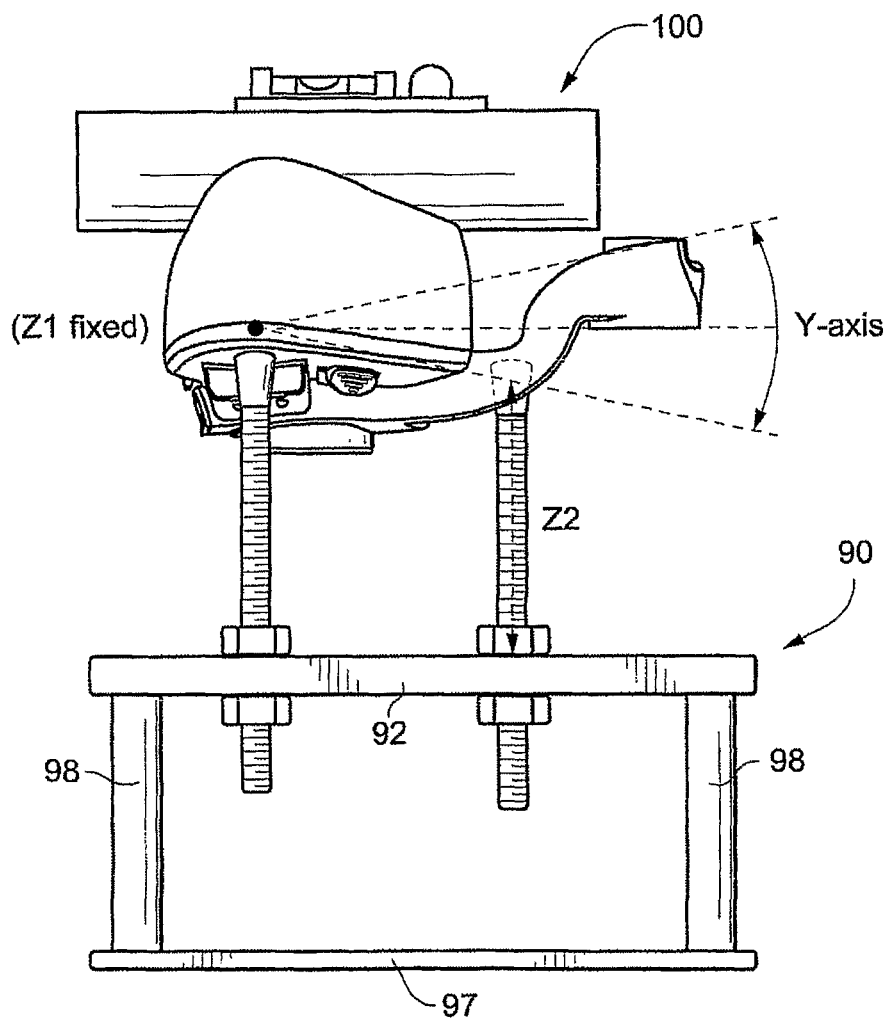
Figure 81:
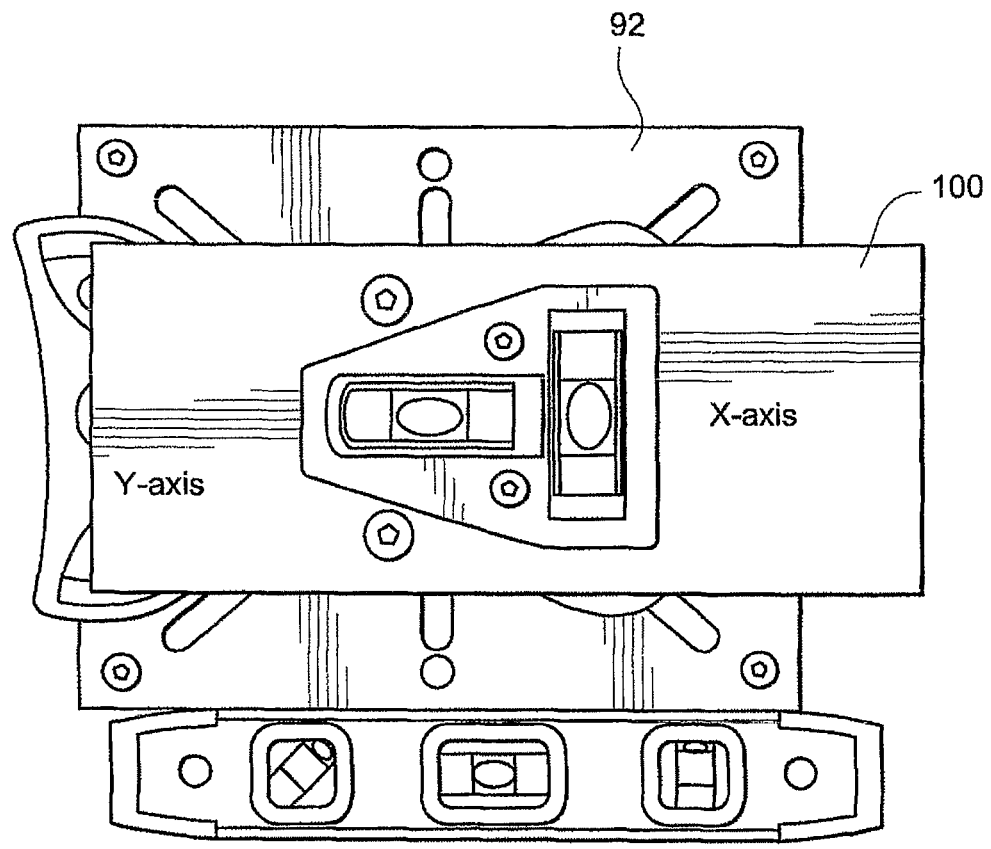
Figure 82:
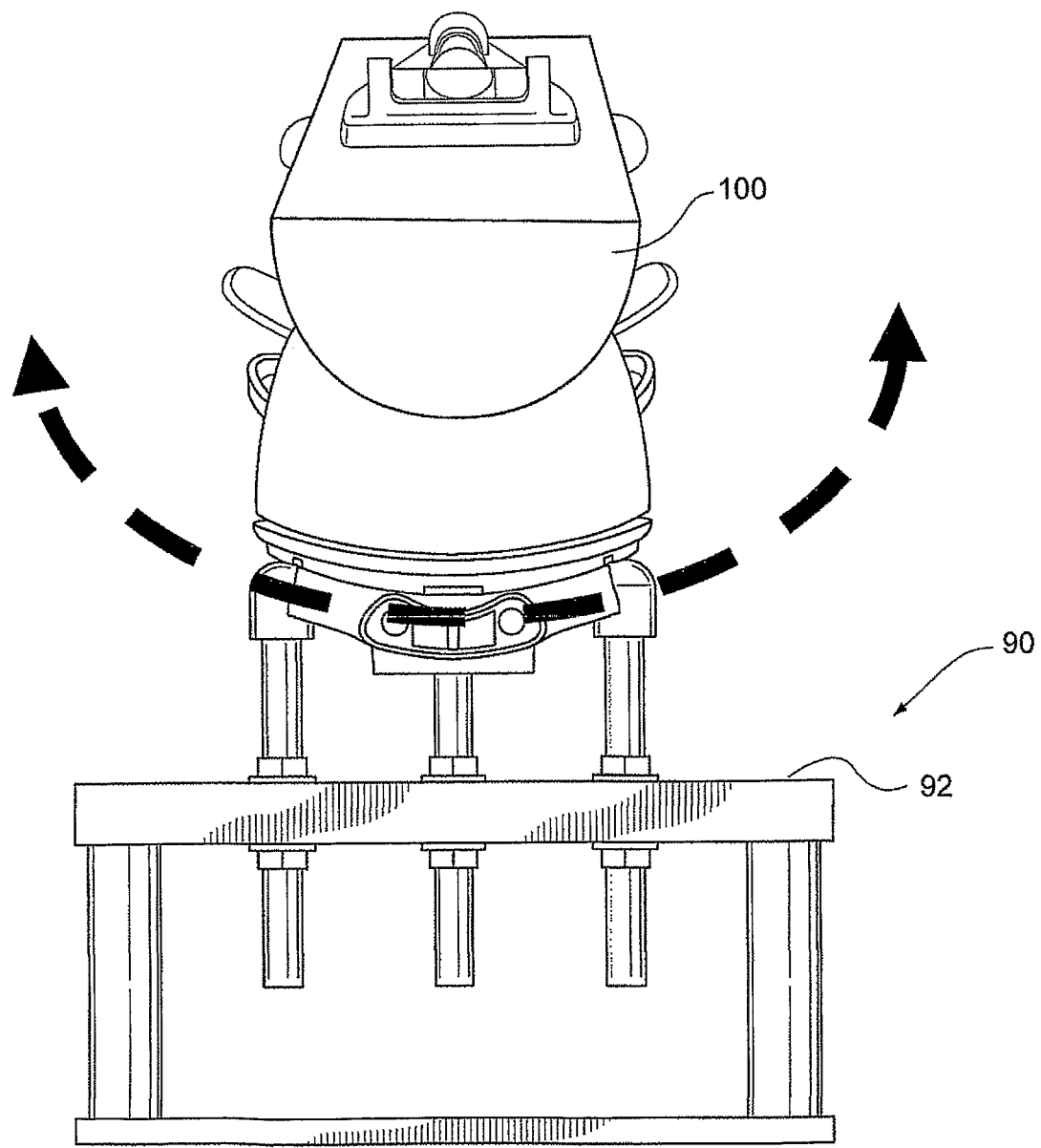
Figure 83:
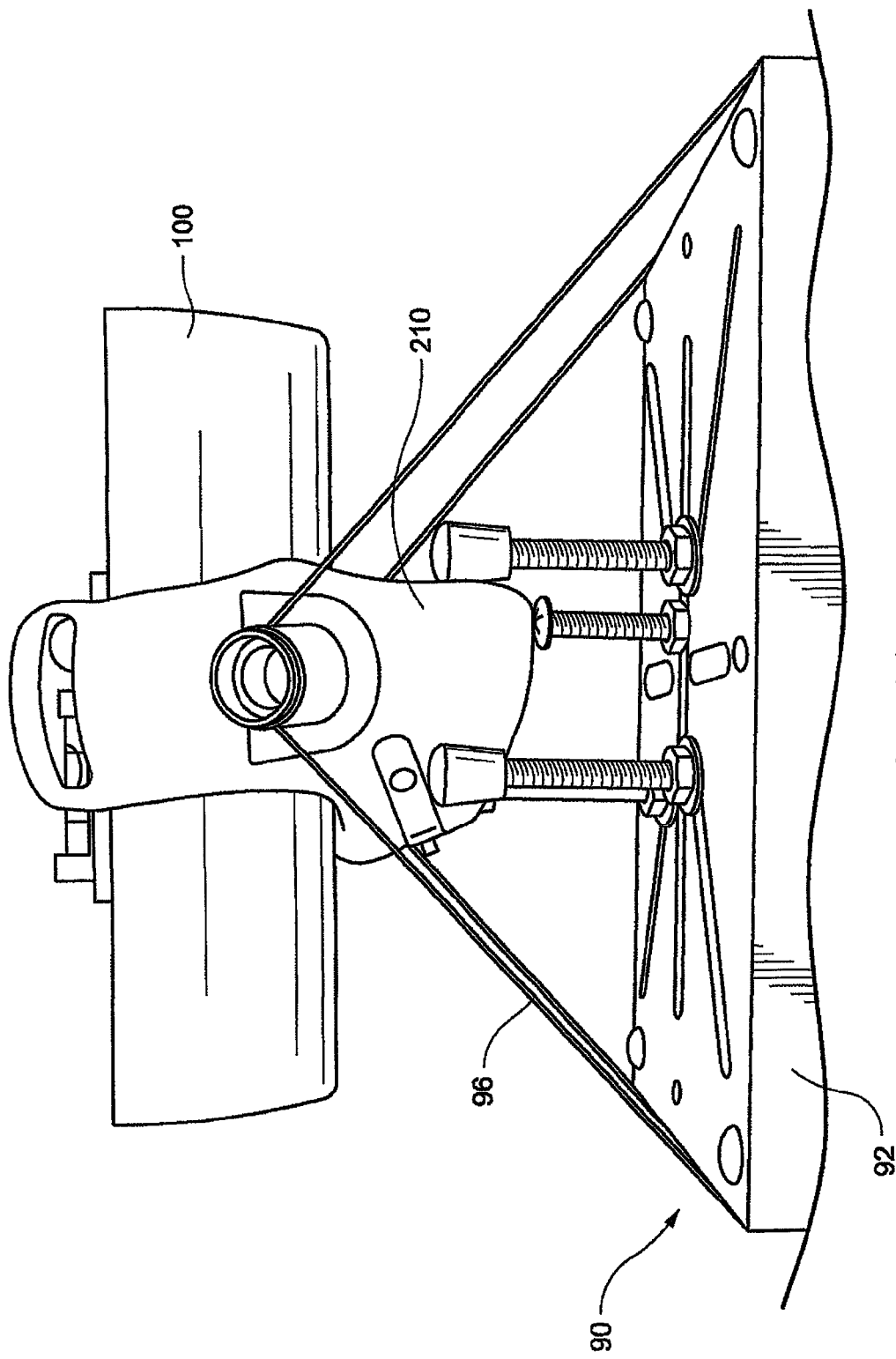
Figure 84:
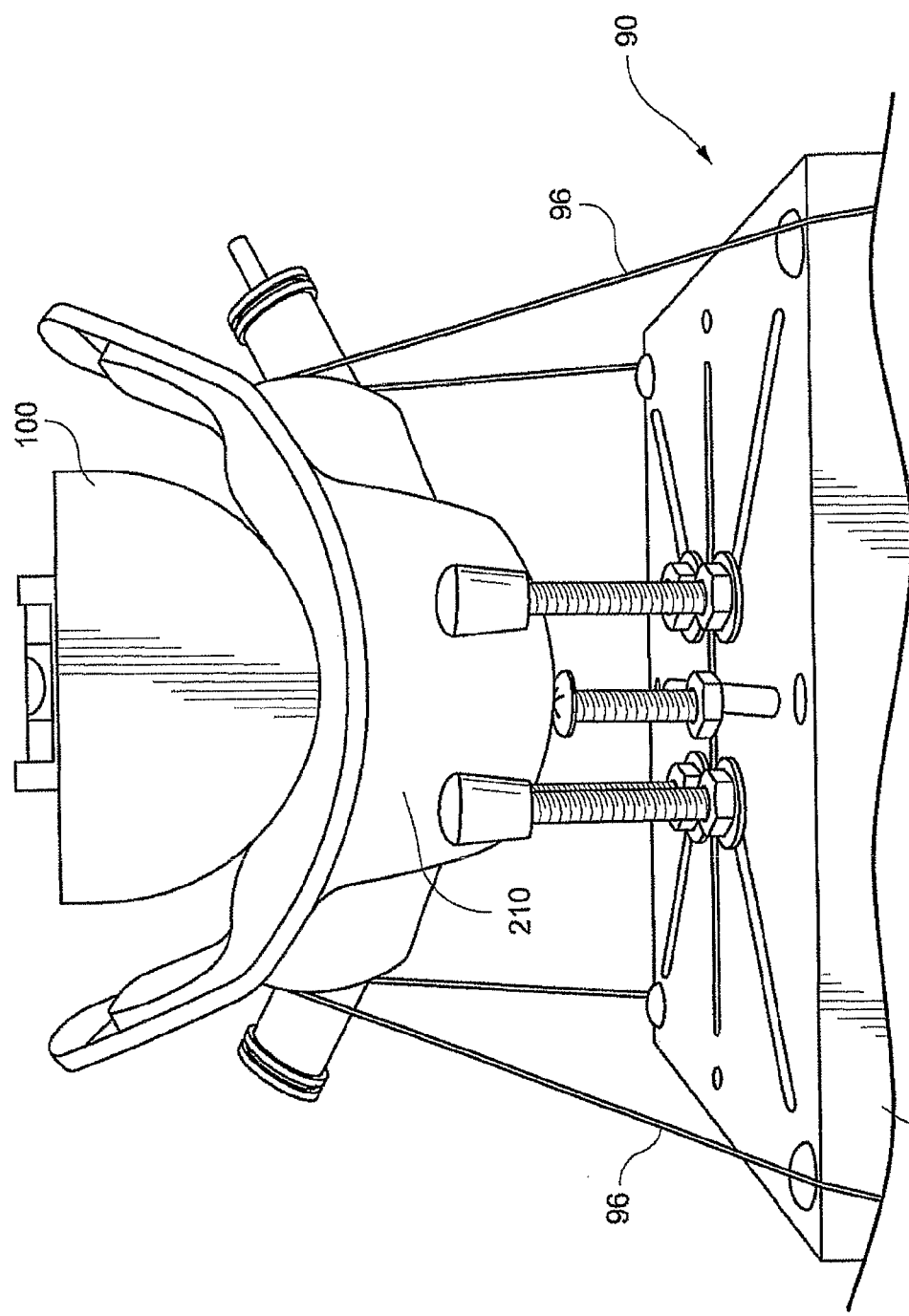
Figure 85:
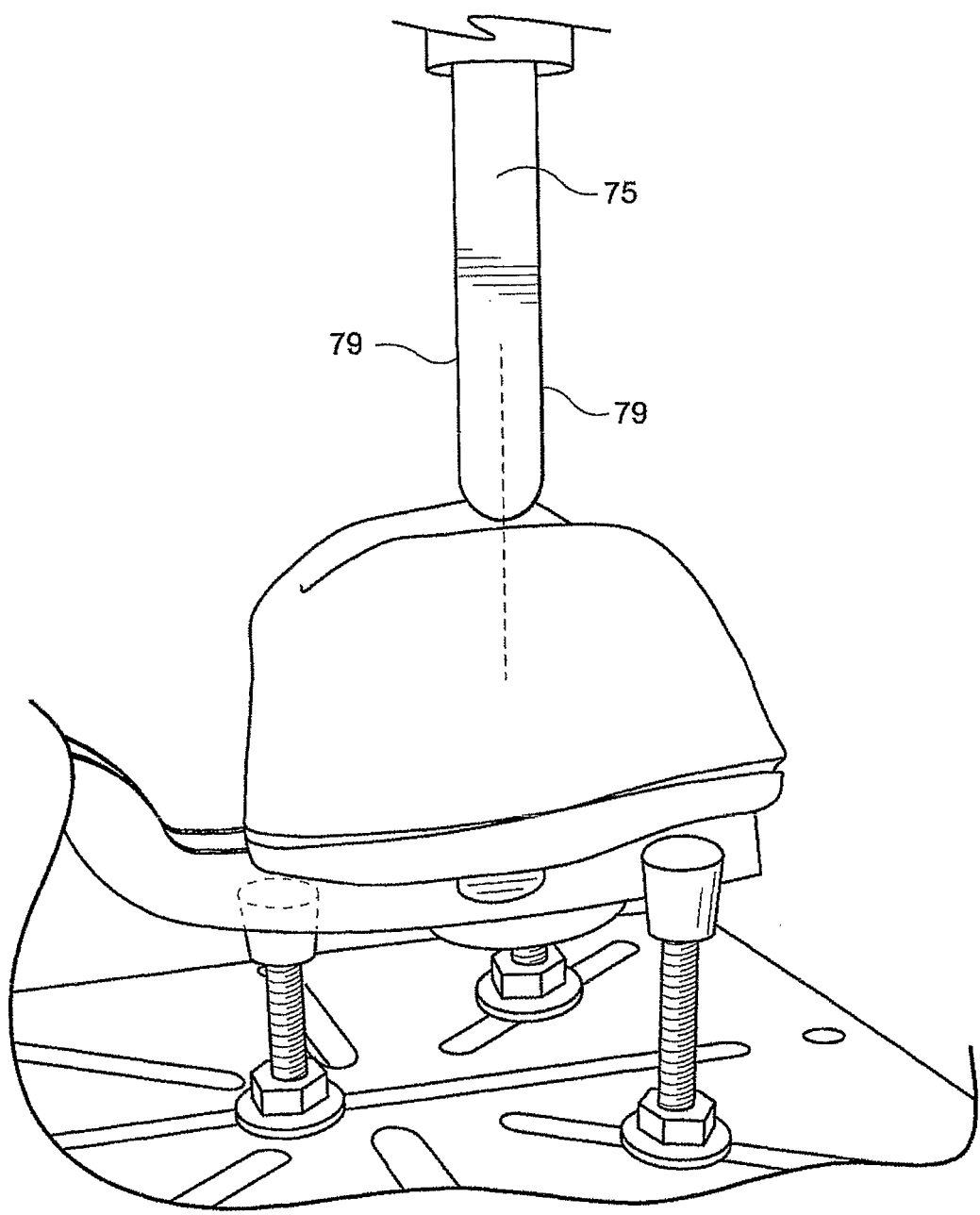
Figure 86:
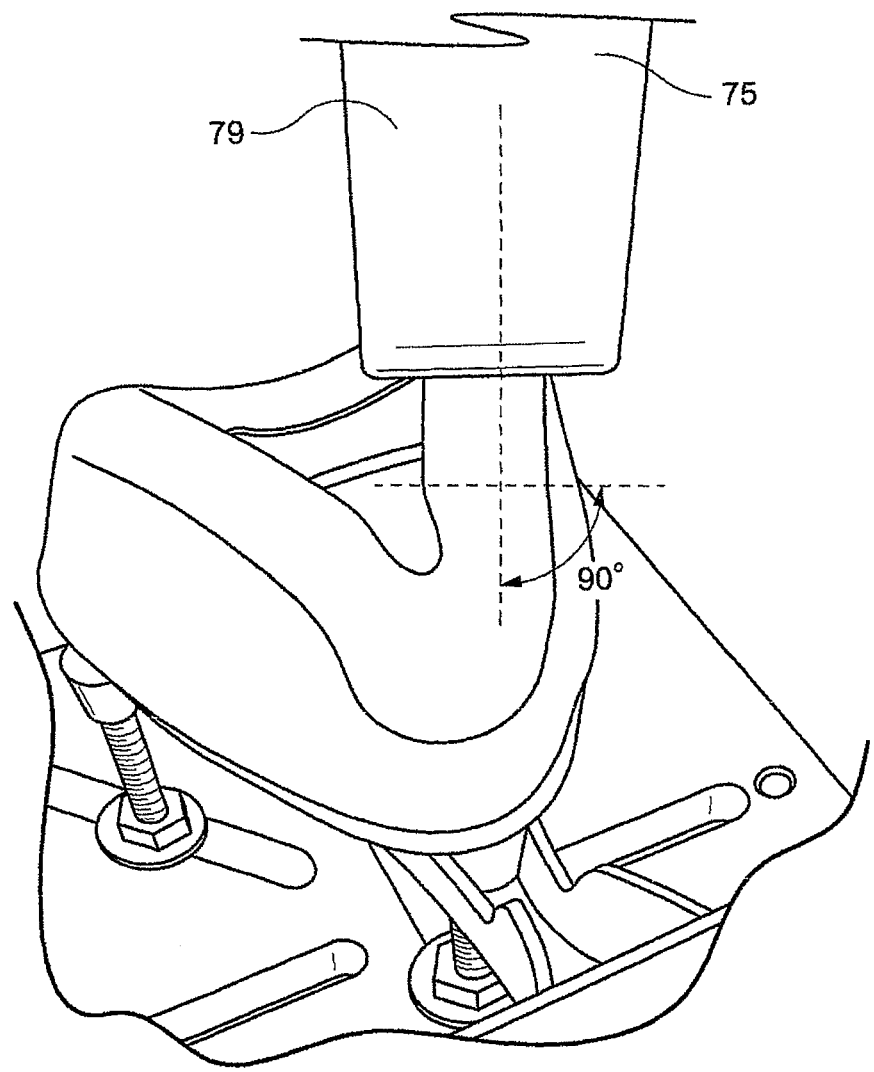
Figure 87:
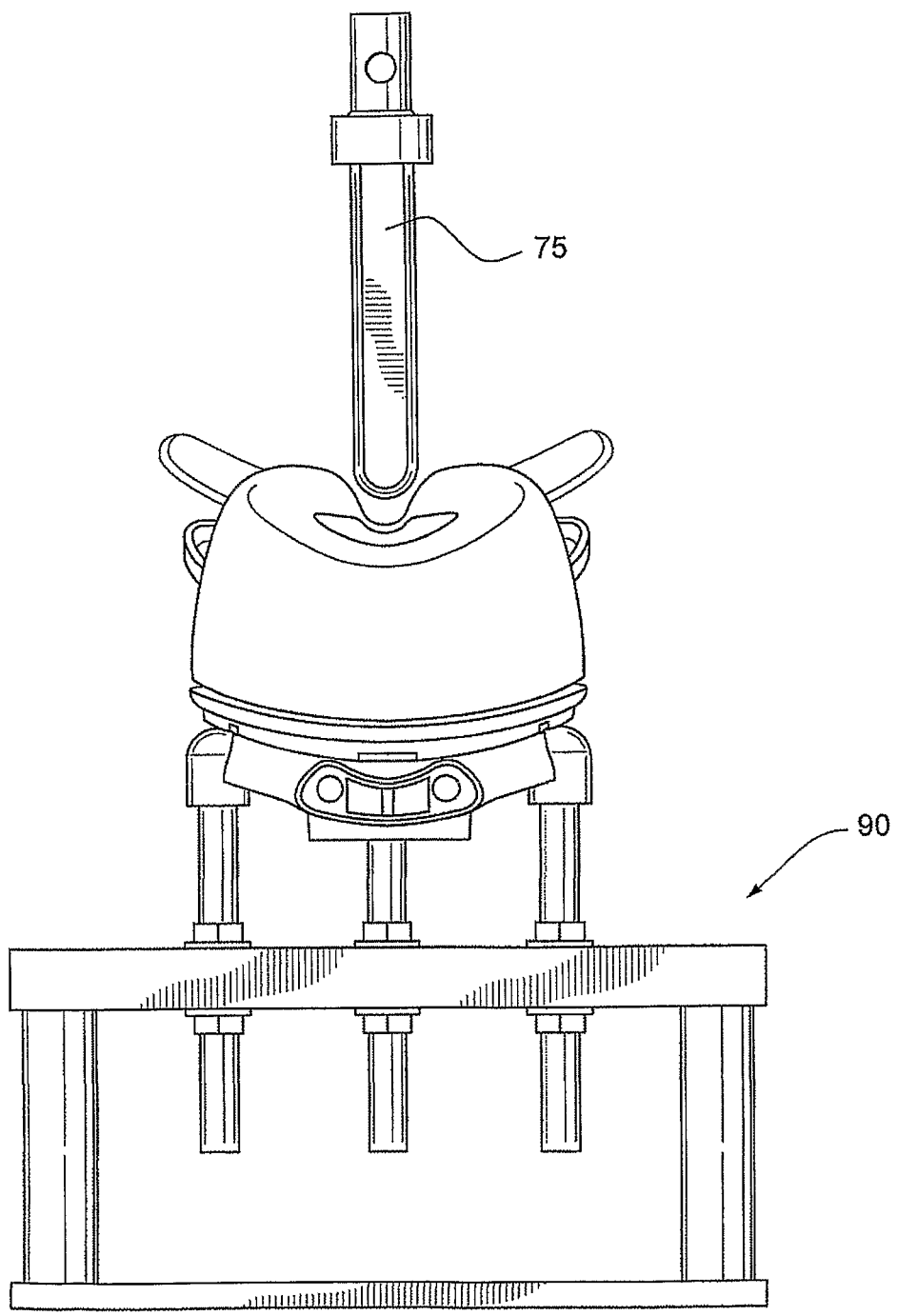
Figure 88:
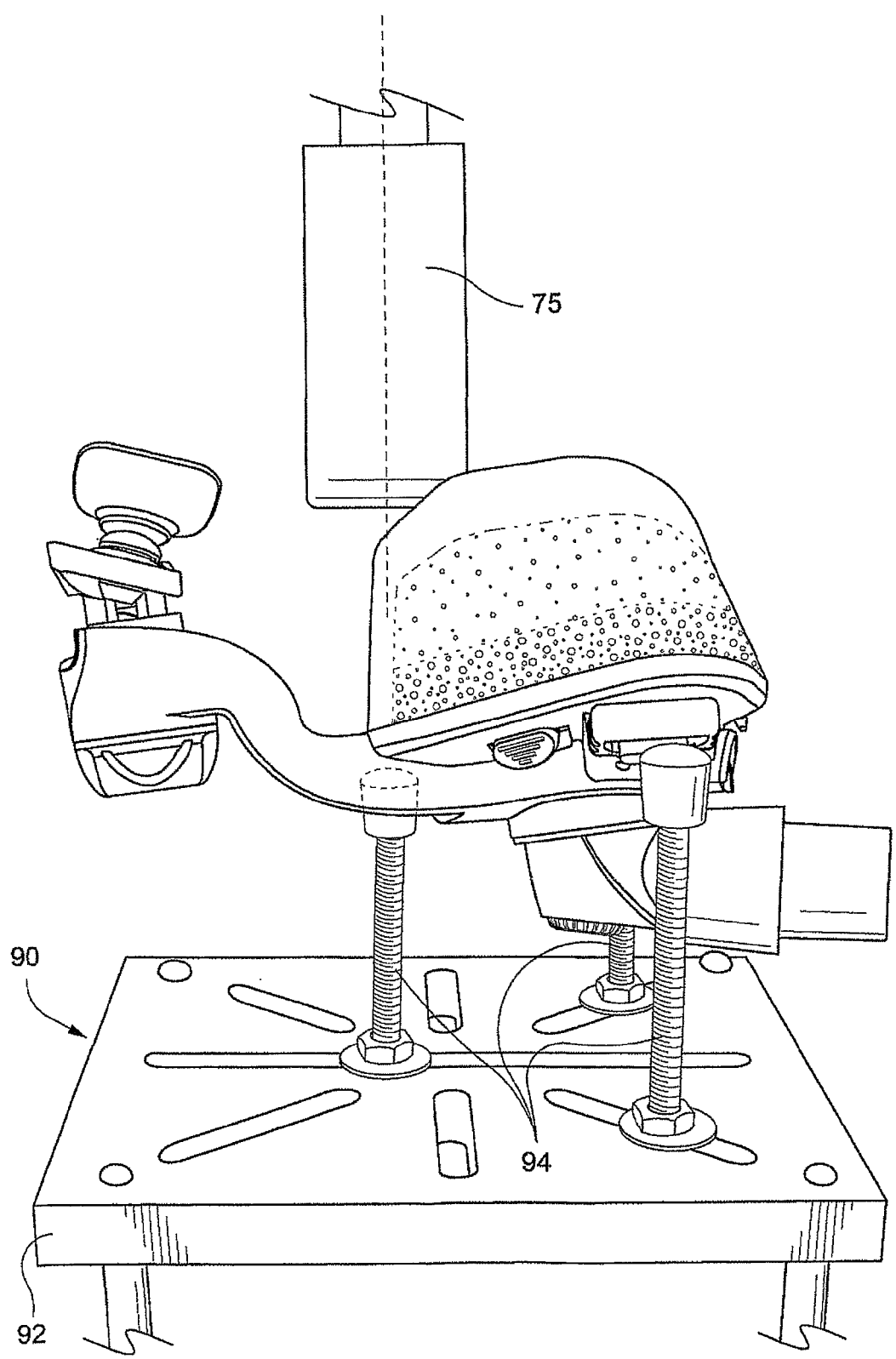

FIG. 62 schematically illustrates how an indenter may be applied to the flexible structure in the lip/chin and nasal bridge regions in accordance with the method of an embodiment of the present invention;

FIG. 63 is an enlarged view illustrating how an indenter may be applied to the flexible structure in the nasal bridge region according to an embodiment of the present invention;

FIG. 64 schematically illustrates how an indenter may be applied to the flexible structure in the cheek region according to an embodiment of the present invention;

FIG. 65 defines cross-sectional views in a nose or nasal bridge region, cheek region, and lip/chin region;

FIG. 66 shows loading diagrams for the SleepNet Mojo mask in the nasal bridge, cheek, and chin regions as defined per FIG. 65, and loading diagrams for the SleepNet Phantom mask in the nasal bridge, cheek, and lip regions as defined per FIG. 65;

FIG. 67 is a schematic view of a mask mounted in a support jig for testing according to an embodiment of the present invention;

FIG. 68 is a perspective view of the support jig of FIG. 67 with a mask superimposed;

FIG. 69 is an enlarged perspective view showing a chin region support for SleepNet Phantom mask according to an embodiment of the present invention;

FIG. 70 is a perspective view showing the SleepNet Phantom mask in the support jig according to an embodiment of the present invention;

FIG. 71 illustrates a cushion coordinate system;

FIG. 72 illustrates cushion reference points;

FIG. 73 is a perspective view of a mask support jig according to an embodiment of the present invention;

FIG. 73B are plan views of the jig of FIG. 73 according to an embodiment of the present invention;

FIGS. 74-1 to 74-3 are various views of an indenter according to an embodiment of the present invention;

FIG. 75 is a perspective view of an alignment block according to an embodiment of the present invention;

FIG. 76 is a view along the ZX plane illustrating the setting up of side posts according to an embodiment of the present invention;

FIG. 77 illustrates leveling of the jig X-axis supports according to an embodiment of the present invention;

FIG. 78 illustrates checking the symmetry of the jig X-axis supports according to an embodiment of the present invention;

FIG. 79 illustrates locating the alignment block on the cushion according to an embodiment of the present invention;

FIG. 80 illustrates adjusting the jig Y-axis support according to an embodiment of the present invention;

FIG. 81 is a top view illustrating the alignment block on the cushion with the spirit level indicating flat plane according to an embodiment of the present invention;

FIG. 82 illustrates alignment of the X-axis using the alignment block according to an embodiment of the present invention;

FIGS. 83 and 84 are various views showing the SleepNet Phantom mask in a support jig according to an embodiment of the present invention;

FIGS. 85 and 86 illustrate alignment of the indenter in the cheek region according to an embodiment of the present invention;

FIGS. 87 and 88 illustrate alignment of the indenter in the nasal bridge region according to an embodiment of the present invention;

FIGS. 89-1 and 89-2 are cross-sectional views showing a flexible structure according to an embodiment of the present invention in non-compressed and compressed positions;

FIG. 90 is a schematic view illustrating a known single gel bladder being compressed in use.

FIG. 91 is a schematic view showing the outer and inner walls and chamber of a flexible structure according to an embodiment of the present invention; and FIGS. 92-1 and 92-2 are schematic views showing gels being cured at a non-parallel angle with respect to one another.

4. DETAILED DESCRIPTION OP ILLUSTRATED EMBODIMENTS

FIGS. 1 to 11 illustrate a mask assembly 10 including a flexible structure 20 according to an embodiment of the present technology. As illustrated, the mask assembly 10 includes flexible structure 20, a frame 40, a forehead support 50 (providing one or more forehead pads 52), an elbow 60 (with swivel 62) provided to the frame and adapted to be connected to an air delivery tube that delivers breathable gas to the patient, and a headgear assembly (not shown) adapted to removably attach to the frame (e.g., via headgear slots or clips 61) and forehead support (e.g., via headgear clips or slots 51) so as to maintain the mask assembly in position on the patient's head in use. In an embodiment, the flexible structure 20 may be retrofit or otherwise provided to an existing mask (e.g., existing cushion clip may be used to attach the flexible structure to an existing frame of the mask). For example, the mask assembly 10 may be of similar construction to the ResMed ACTIVA LT nasal mask (with existing cushion clip 42 used to attach flexible structure 20 to the frame 40), however in the present example a different form of flexible structure 20 is adopted.

Another form of mask may not include a forehead support.

The flexible structure and frame may together define a plenum, that is, an enclosed volume of gas under pressure. The flexible structure may incorporate one or more internal chambers, the spaces within such one or more chambers may be filled with one or more materials such as air, gel or foam. The structure may be formed in one part, or may be assembled from more than one part. The flexible structure may provide sealing and cushioning functions, as well as retention features with a frame.

In this specification, the word "cushion" will be used interchangably with the phrase "flexible structure".

In this specification, the word "bladder" will be used to refer to the structure that may be filled with a material. For example, the bladder may be manufactured from liquid silicone rubber (LSR), or polyurethane or another room temperature vulcanising (RTV) rubber. The filling material may be a gel.

In order to adequately describe the materials and structures preferred for the present technology, we have used a number of existing test methods, and created new test methods when needed. These test methods are described in the last section of our patent application.

4.1 Flexible Structure Performance

The challenge of making a respiratory mask cushion that is comfortable to wear and effective for a broad range of people for a long period of time is surprisingly complex. A face is a complex three dimensional structure defined by both rigid bone and flexible tissue. Different regions of the face have different sensitivities, different structures and different capacity to bear loads. Different people have differently shaped and sized noses. It is possible to manufacture an entirely rigid mask cushion that be a perfect fit for a single person, however in order to accommodate a greater range of different face shapes and sizes, it is generally preferable to have at least some regions of flexibility in a cushion, without requiring excessive force on a patient's face to effect a seal in that region. Furthermore it is generally desirable for a mask cushion to be able to accommodate patient movement without breaking effective seal, and to be able to accommodate movement from tube drag.

In the following discussion, reference will be made to force-indentation behaviour of a cushion. Test methods for performing force-indentation analysis of a cushion are described in detail in a later section of the specification. In brief, the test methods simulate in-use performance of cushions and are influenced by a combination of features including material properties and the shape and configuration of the mask (including the cushion). The indenter test simulates the effect of a face pressing into a cushion and is reflective of the force on the face by measuring local indentation by an indentor. As will be subsequently described and in accordance with the present technology, certain forms of force-indentation behaviour are preferred in certain regions of the face, whereas other forms of behaviour are preferred in other regions of the face. The rate of increase of force with displacement reflects sensitivity of a cushion to headgear tension. At a certain indentation (or extension of the indenter) the force rapidly increases, reflective of the cushion being close to fully compressed and the force on the face rapidly increasing with further indentation. At this point the cushion may be described as "bottoming out".

We have discovered that when the force-indentation curve of a mask does not increase too, rapidly, but has a gradually increasing slope, a mask is easier to adjust because the cushion does not suddenly bottom out. In this way the headgear adjustment is more "forgiving" of headgear tension. In some masks there is a very fine line between sealing and being uncomfortable, such masks may be described as being overly "sensitive" to headgear tension.

The nasal bridge region is an area of the face of interest. This region generally comprises a thin layer of skin over bone. It is typically sensitive to excessive forces. It is also typically variable amongst people with different ethnic backgrounds. For example, people with an East Asian family background often have low nasal bridge heights, whereas people with a Caucasian family background often have higher nasal bridge heights. The difference in heights may be in the order of approximately 20 mm. A corresponding nasal bridge region of the cushion may be identified. A mask cushion in accordance with an aspect of the present technology is constructed to exert a low, comfortable force on the nasal bridge and to effect a seal and yet be able to accommodate such a range in nasal bridge heights. Such a mask cushion is constructed to provide the low comfortable force over a range of indentations that spans the typical range of nasal bridge heights encountered for the mask. Hence an aspect of one form of the present technology is to provide a mask cushion that provides a low force on the nasal bridge over a range of approximately 20 mm. In one form, the cushion is arranged to be sufficiently viscoelastic in the nasal bridge region so that it relieves pressure on the nasal bridge over time. In another form the cushion may be more elastic in the nasal bridge region. In another form there may be no soft filling material in the cushion in the nasal bridge.

Another region of the face of interest is the cheek region of the face. This region of the face is along the sides of the nose. A cushion in accordance with an aspect of the present technology may be structured to deliver a relatively higher force to the cheek region of the patient's face compared to the nasal bridge region.

A third region of the face of interest for nasal masks is an upper lip region. This region is between the mouth and nose of the patient. In this region there is a layer of skin and muscle over the teeth. Some patients find this region less sensitive than the nasal bridge, but more sensitive than the cheek region. This region may not be contacted by full-face masks. In one form the cushion includes a viscoelastic aspect in the centre of the lip region.

A fourth region of the face of interest is a lower lip or chin region. Depending on the size and shape of a mask in comparison to a person's face, a cushion may be positioned on skin adjacent the teeth of the lower jaw, or if lower down the face, on bone. Unlike the previous three regions, the lower-lip or chin region may move relative to the rest of the face with jaw movement. A full-face mask system in accordance with the present technology may have a different set of properties, such as capacity to accommodate such jaw movement.

Regions intermediate of the above identified regions may be of separate interest. A cushion in accordance with the present technology may be structured to have different properties in the corresponding cushion regions to those regions identified above, and have a blend of properties for intermediate regions of the cushion.

4.1.1 Mask with Flexible Structure Force Indentation Curves

The following tables list approximate indentation forces in the different regions for masks with different flexible structures in accordance with the present technology, for indentation distances shown. The RCFI-1 forces and RCFI-1 indentations measured in the present test are associated with respective in-use forces and indentations of the mask, however the exact forces felt by a particular patient will depend on factors such as the size and shape of their nose, the mask position on the face and the tension in headgear. FIGS. 12-1, 13-1, and 14-1 illustrate test results of load versus indentation in different regions for both prior art masks (shown in solid lines) and for masks including flexible structures in accordance with embodiments of the present technology (shown in broken lines with data points). Also, the following tables list data points in the figures for the masks including flexible structures in accordance with the present technology. As illustrated, each data point for a mask including a first flexible structure is represented by a diamond symbol, each data point for a mask including a second flexible structure is represented by a square symbol, each data point for a mask including a third flexible structure is represented by a cross symbol, each data point for a mask including a fourth flexible structure is represented by a circle symbol, and each data point for a mask including a fifth flexible structure is represented by a triangle symbol.

Figures 1, 12:
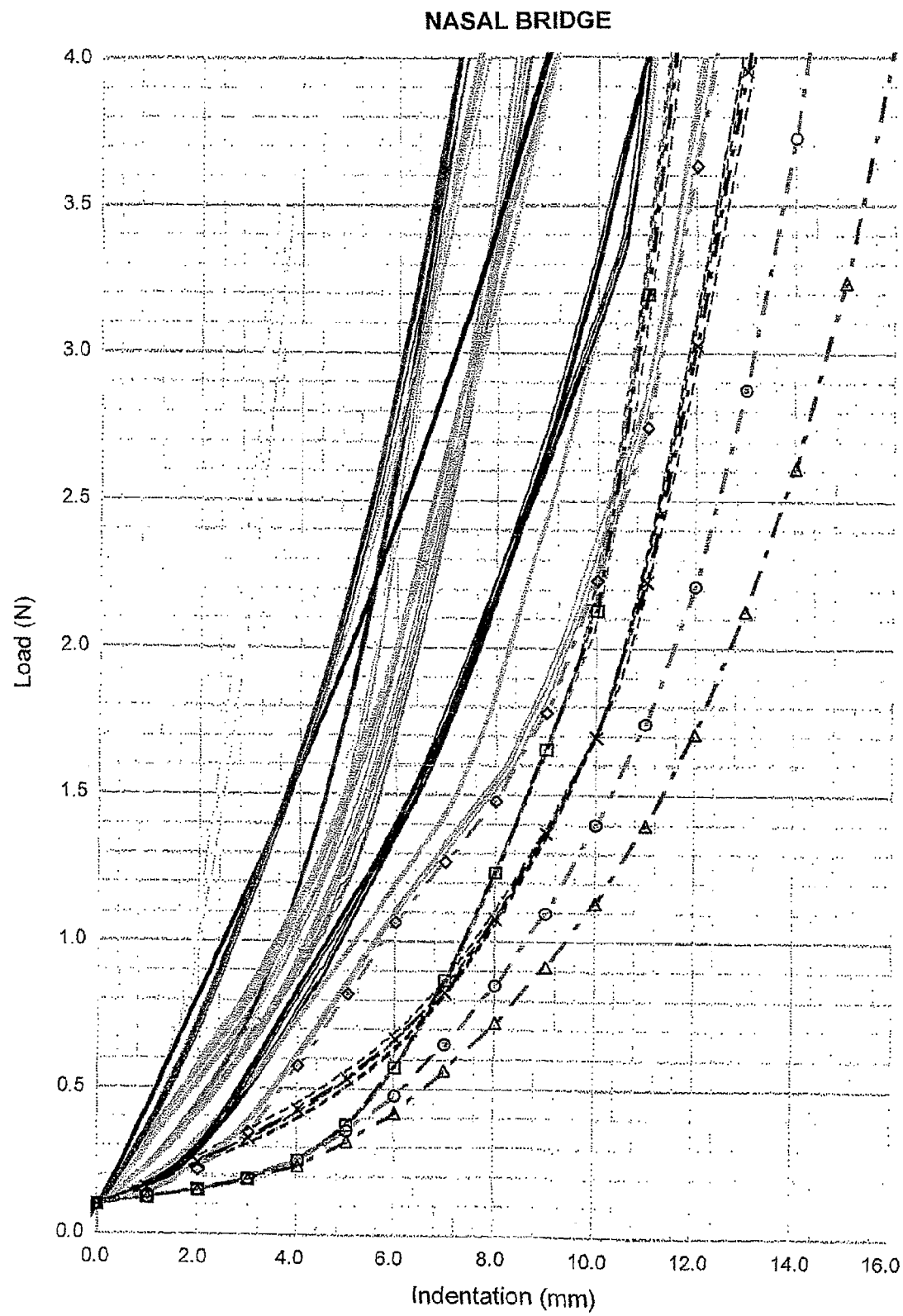
Figures 2, 12:
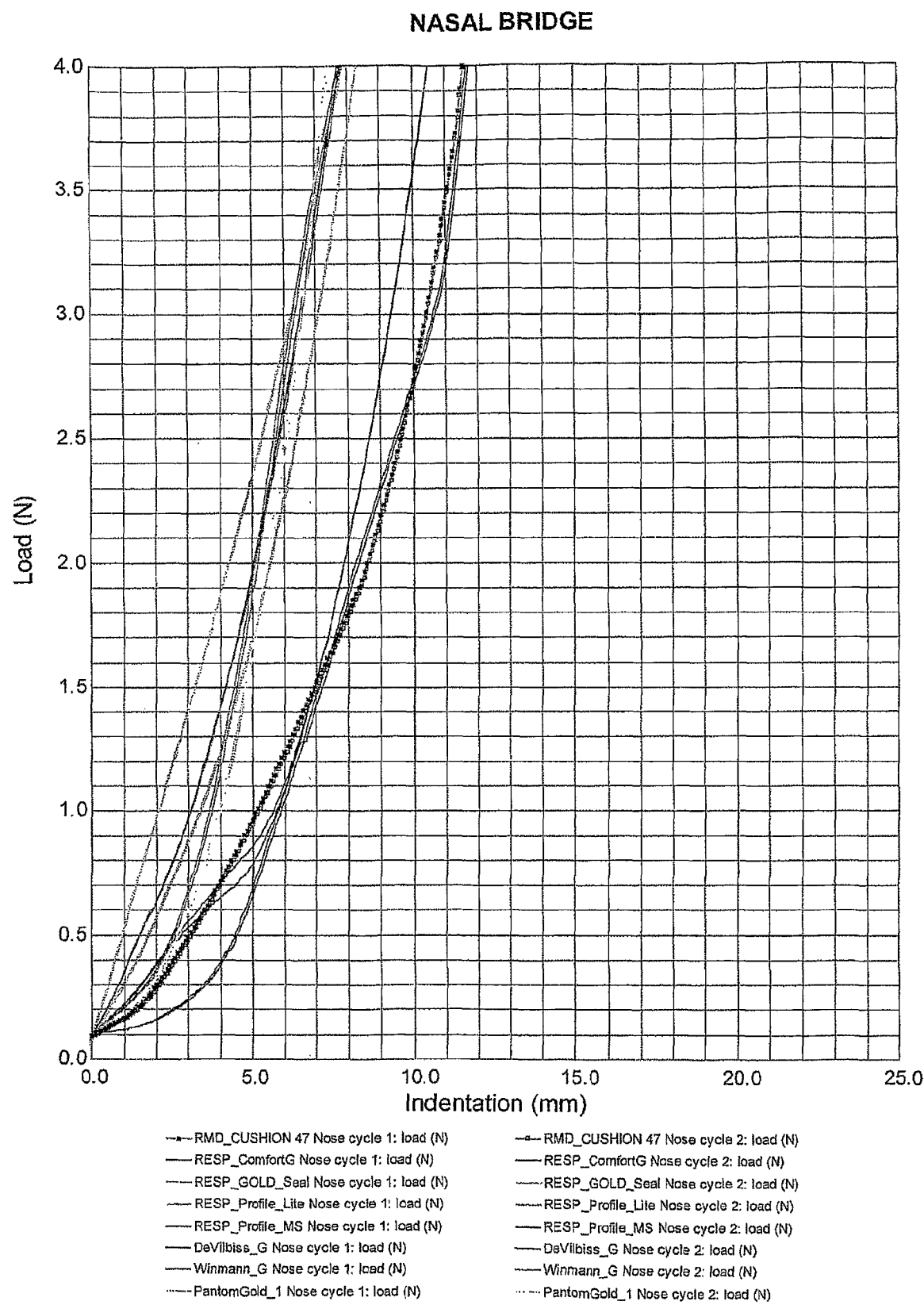
Figures 1, 13:
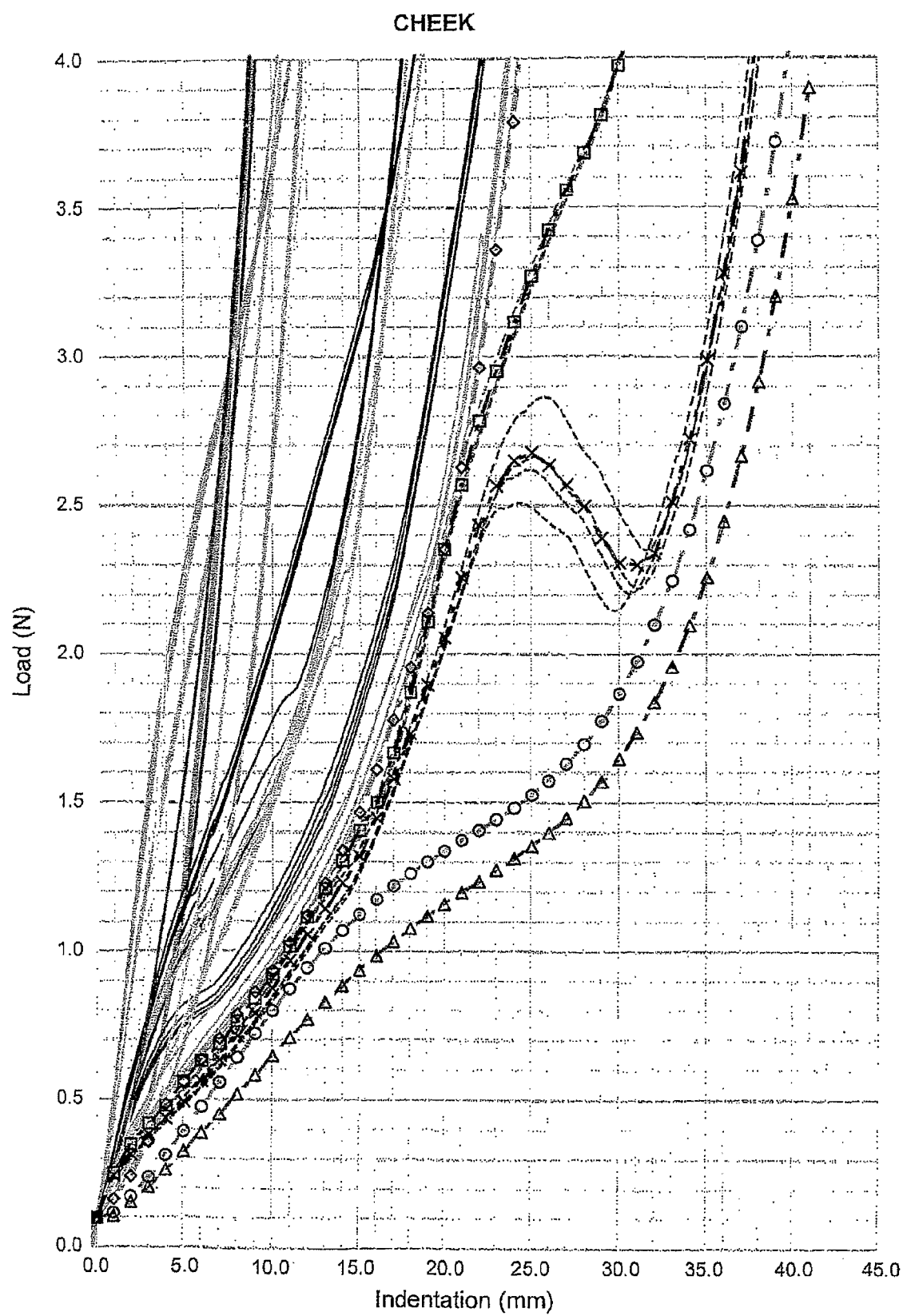
Figures 2, 13:
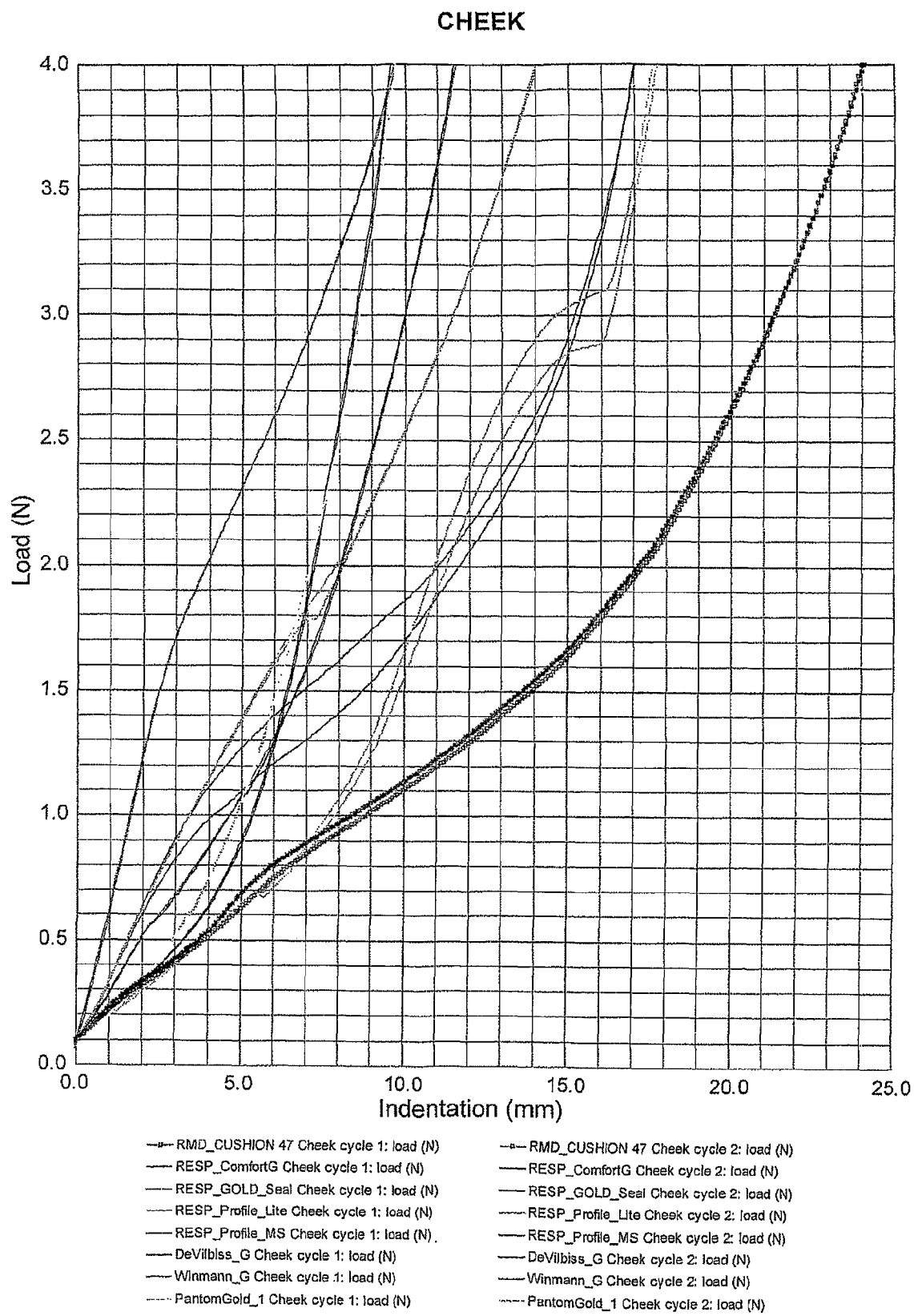
Figures 1, 14:
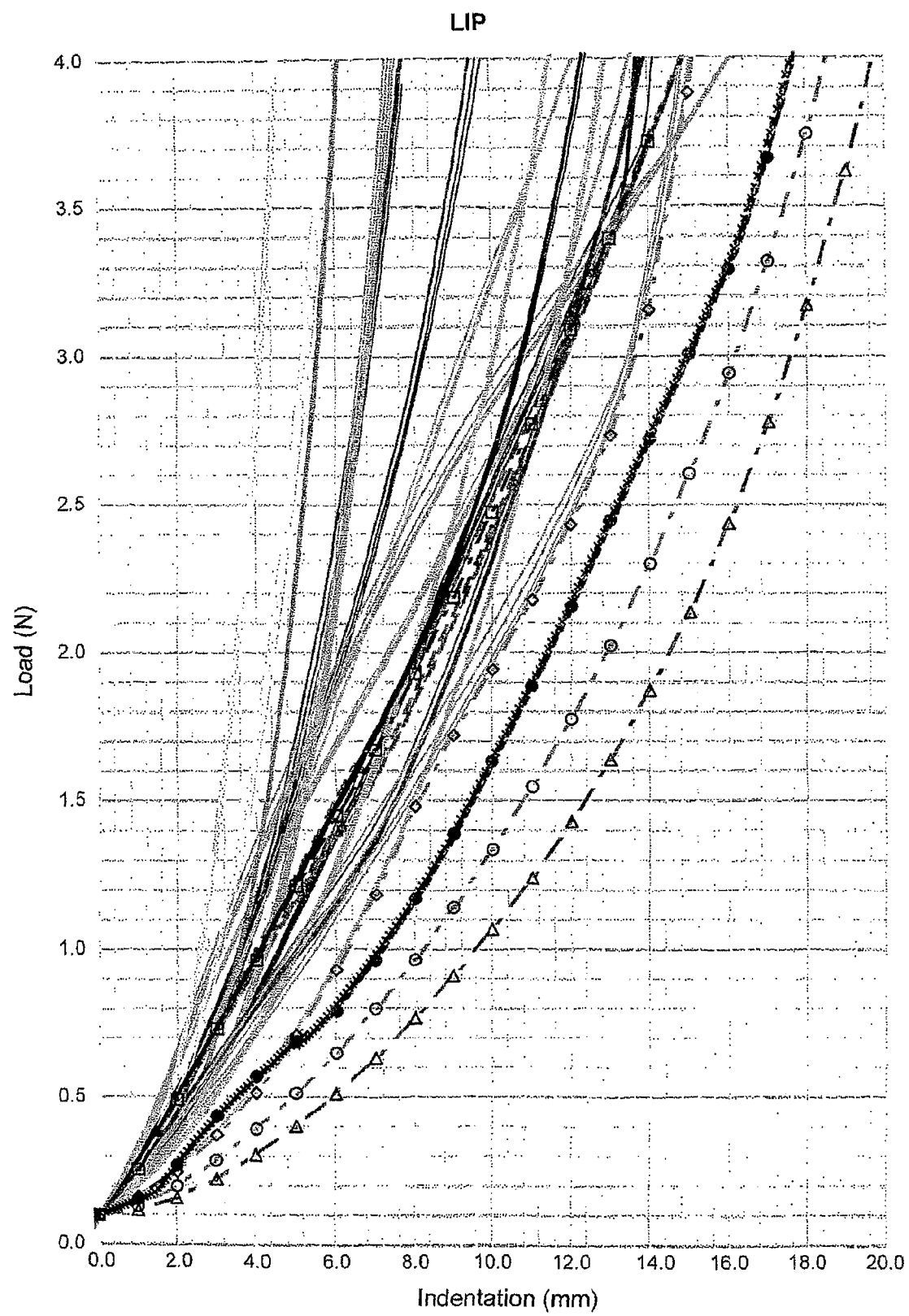
Figures 2, 14:
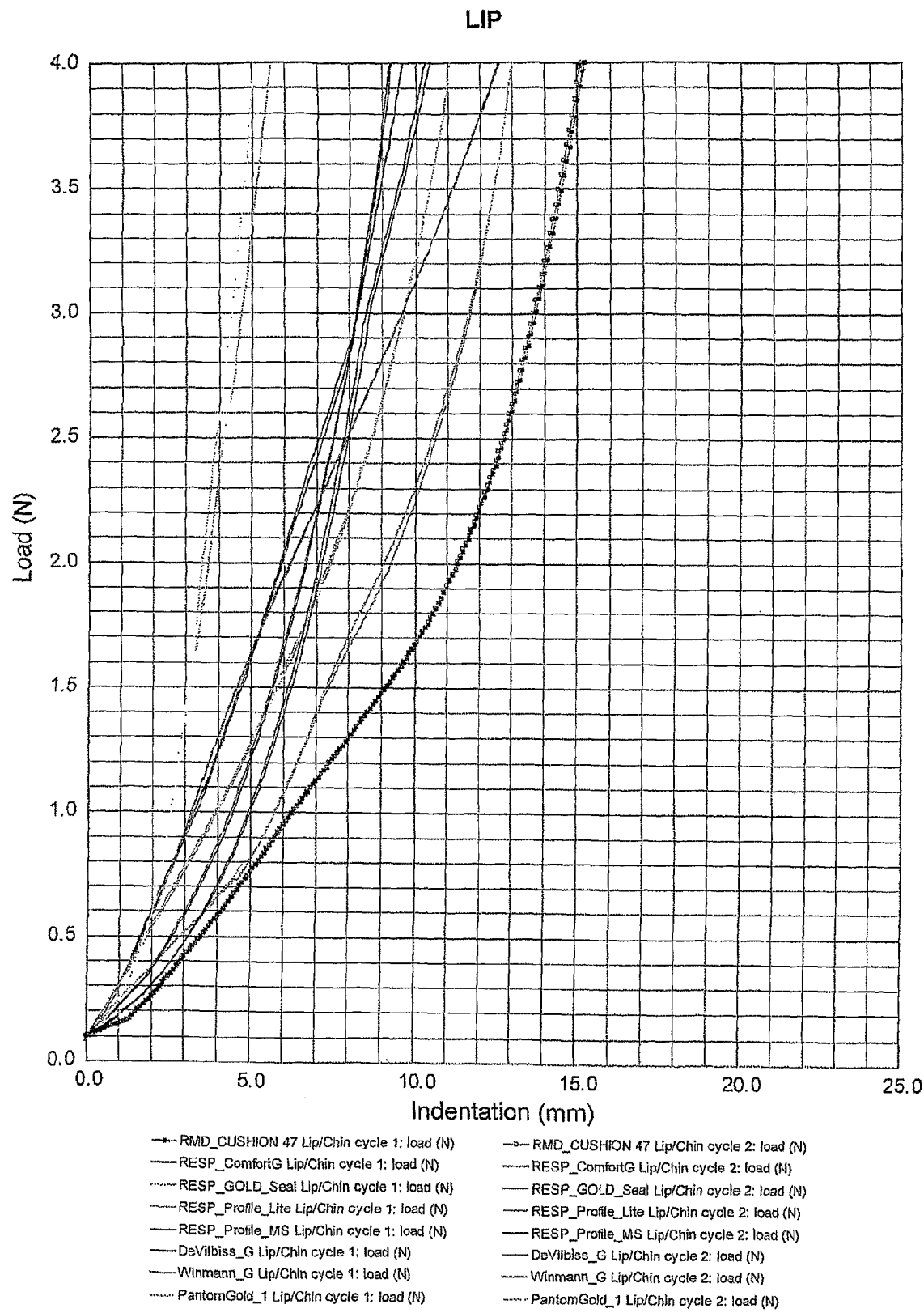
Figure 15:
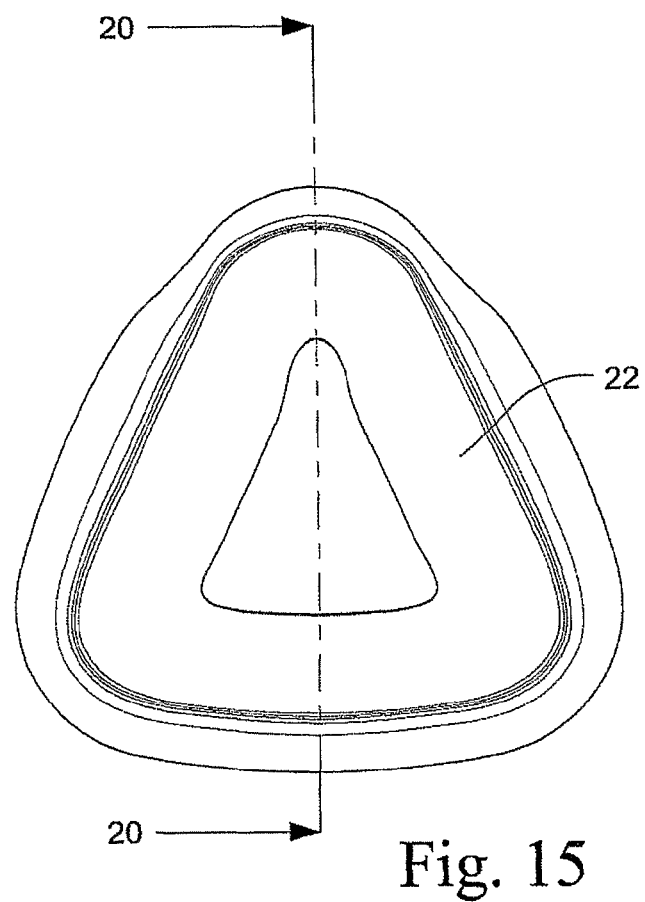
FIG. 15 is a view showing a patient contacting side of a flexible structure according to an embodiment of the present invention.
Figure 16:
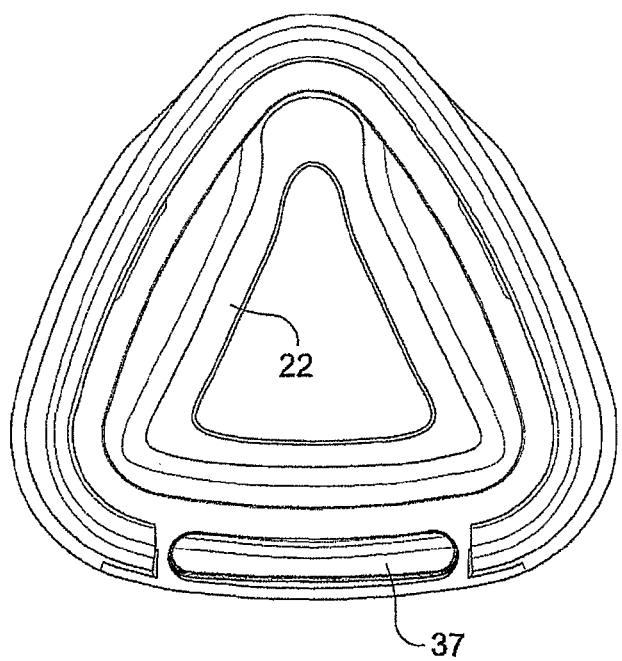
FIG. 16 is a view showing a frame contacting side of the flexible structure of FIG. 15.
Figure 17:
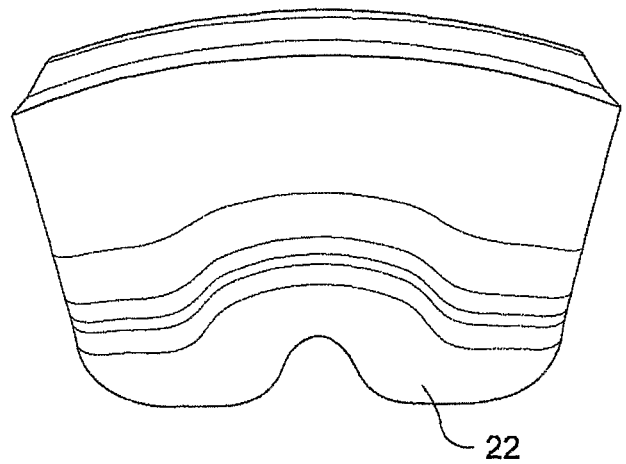
FIG. 17 is a top view of the flexible structure of FIG. 15.
Figure 18:
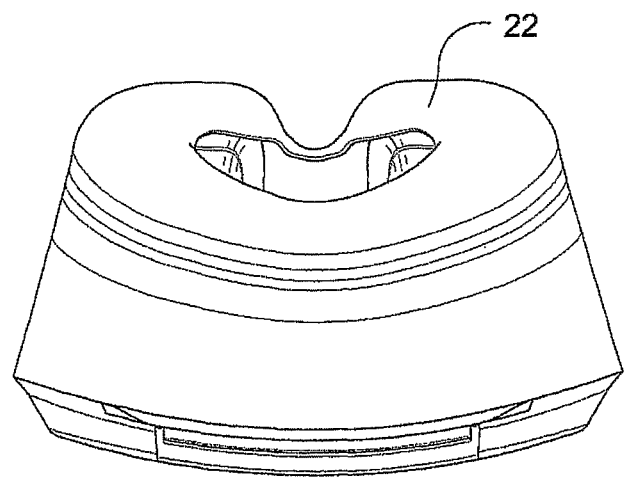
FIG. 18 is a bottom view of the flexible structure of FIG. 15.
Figure 19:
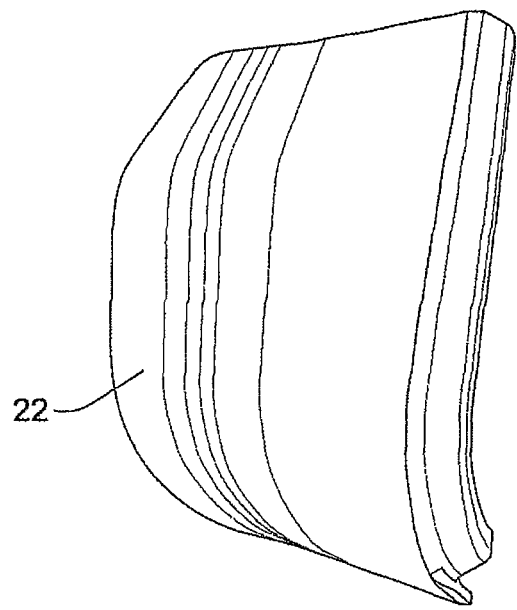
FIG. 19 is a side view of the flexible structure of FIG. 15.

FIG. 12-1 and the table of section 4.1.2 show test results for load versus indentation in the nasal bridge region, FIG. 13-1 and the table of section 4.1.3 show test results for load versus indentation in the cheek region, and FIG. 14-1 and the table of section 4.1.4 show test results for load versus indentation in the lip region.

The data points and results graphs were determined using the testing equipment and procedures described in ResMed Cushion Force Indentation Test Method #1 (RCFI-1).

As shown in FIGS. 12-1, 13-1, and 14-1, flexible structures in accordance with aspects of the present technology allow greater deformation at lower forces than flexible structures known in the art.

For example, as shown in FIG. 12-1, a flexible structure in accordance with one form of the present technology has in the nasal bridge region, an RCFI-1 force of less than about 1 N at an RCFI-1 indentation of about 6 mm. Furthermore, such flexible structure has an RCFI-1 force of less than about 1.5N at an RCFI-1 indentation of about 8 mm. Furthermore, such flexible structure has an RCFI-1 force of less than about 2N at an RCFI-1 indentation of about 10 mm. By way of contrast, one prior art gel mask manufactured by SleepNet corporation exceeds an RCFI-1 force of 2N at an RCFI-1 indentation of about 3 mm in the nasal bridge region.

For example, as shown in FIG. 14-1, flexible structures according to embodiments of the invention in a lip region may be associated with an RCFI-1 force of about 0.6 N or less for an RCFI-1 indentation of about 4.0 mm. By way of comparison flexible structures known in the art are associated with an RCFI-1 force of about 0.7 N or more for the same indentation, e.g. 1.5N or 2N.

In another example, as shown in FIG. 13-1, flexible structures according to embodiments of the invention in a cheek region may be associated with an RCFI-1 force of about 0.6 N or less for an RCFI-1 indentation of about 5.0 mm, whereas flexible structures known in the art are associated with an RCFI-1 force greater than about 0.6 N for the same indentation.

This arrangement allows flexible structures in accordance with embodiments of the present invention to deform and conform to the patient's face without significant forces being applied to the patient's face in use. The testing procedure and resulting graphs (FIGS. 12-1, 13-1, and 14-1) provide a way to accurately compare flexible structures of different masks and more clearly illustrate the conforming properties of flexible structures in accordance with embodiments of the present invention with respect to flexible structures known in the art.

Thus, the flexible structures according to embodiments of the present invention allow more even force distribution of an applied load, whereas flexible structures of the prior art may have concentrated pressure points that are uncomfortable.

Furthermore a flexible structure in accordance with the present technology has a flatter, more gradual transition region on a force indentation analysis, leading to a more gradual increase in force on the face, rather than suddenly bottoming out. A disadvantage of a cushion that suddenly bottoms out is that it may be very sensitive to headgear tension forces, that is very small changes in headgear tension may lead to rapid increase in forces on the face. By way of contrast, a preferred form of cushion in accordance with the present technology is not as sensitive to small changes in headgear tension.

FIGS. 12-2, 13-2, and 14-2 show graphs determined using the testing equipment and procedures described in ResMed Cushion Force Indentation Test Method #2 (RCFI-2). FIG. 12-2 shows test results for load versus indentation in the nasal bridge region, FIG. 13-2 shows test results for load versus indentation in the cheek region, and FIG. 14-2 shows test results for load versus indentation in the lip region.

In each of FIGS. 12-2, 13-2, and 14-2, a flexible structure in accordance with one form of the present technology has an RCFI-2 force of less than about 1 N at an RCFI-2 indentation of about 5 mm.

As shown in FIG. 12-2, a flexible structure in accordance with one form of the present technology has in the nasal bridge region, an RCFI-2 force of less than about 3 N at an RCFI-2 indentation of about 10 mm.

As shown in FIG. 13-2, a flexible structure in accordance with one form of the present technology has in the cheek region, an RCFI-2 force of less than about 2 N at an RCFI-2 indentation of about 10 mm.

As shown in FIG. 14-2, a flexible structure in accordance with one form of the present technology has in the lip region, an RCFI-2 force of less than about 2 N at an RCFI-2 indentation of about 10 mm.

4.1.2 Nasal Bridge Region

| Indentation (RCFI-1 mm) | Cushion #1 (RCFI-1N) | Cushion #2 (RCFI-1N) | Cushion #3 (RCFI-1N) | Cushion #4 (RCFI-1N) | Cushion #5 (RCFI-1N) |
|---|---|---|---|---|---|
| 0 | 0.100 | 0.100 | 0.100 | 0.100 | 0.100 |
| 1 | 0.136 | 0.125 | 0.158 | 0.125 | 0.125 |
| 2 | 0.220 | 0.153 | 0.246 | 0.153 | 0.153 |
| 3 | 0.350 | 0.191 | 0.330 | 0.191 | 0.191 |
| 4 | 0.576 | 0.256 | 0.428 | 0.256 | 0.237 |
| 5 | 0.821 | 0.376 | 0.534 | 0.358 | 0.321 |
| 6 | 1.066 | 0.572 | 0.669 | 0.477 | 0.418 |
| 7 | 1.273 | 0.869 | 0.827 | 0.651 | 0.562 |
| 8 | 1.478 | 1.236 | 1.078 | 0.851 | 0.725 |
| 9 | 1.780 | 1.655 | 1.371 | 1.097 | 0.916 |
| 10 | 2.231 | 2.129 | 1.696 | 1.400 | 1.134 |
| 11 | 2.748 | 3.200 | 2.226 | 1.743 | 1.400 |
| 12 | 3.634 | 4.666 | 3.026 | 2.212 | 1.710 |
| 13 | 4.596 | 6.204 | 3.955 | 2.877 | 2.129 |
| 14 | | | 4.931 | 3.727 | 2.612 |
| 15 | | | | 4.900 | 3.240 |

4.1.3 Cheek Region

| Indentation (RCFI-1 mm) | Cushion #1 (RCFI-1N) | Cushion #2 (RCFI-1N) | Cushion #3 (RCFI-1N) | Cushion #4 (RCFI-1N) | Cushion #5 (RCFI-1N) |
|---|---|---|---|---|---|
| 0 | 0.1000 | 0.1000 | 0.1000 | 0.1000 | 0.1000 |
| 1 | 0.1620 | 0.2520 | 0.2430 | 0.1153 | 0.1059 |
| 2 | 0.2410 | 0.3490 | 0.3140 | 0.1720 | 0.1534 |
| 3 | 0.3570 | 0.4200 | 0.3830 | 0.2387 | 0.2065 |
| 4 | 0.4830 | 0.4790 | 0.4360 | 0.3127 | 0.2640 |
| 5 | 0.5570 | 0.5590 | 0.4920 | 0.3918 | 0.3248 |
| 6 | 0.6320 | 0.6290 | 0.5600 | 0.4738 | 0.3880 |
| 7 | 0.7040 | 0.6850 | 0.6320 | 0.5570 | 0.4526 |
| 8 | 0.7850 | 0.7630 | 0.7130 | 0.6398 | 0.5177 |
| 9 | 0.8620 | 0.8410 | 0.7910 | 0.7208 | 0.5826 |
| 10 | 0.9340 | 0.9220 | 0.8750 | 0.7990 | 0.6466 |
| 11 | 1.0280 | 1.0150 | 0.9680 | 0.8735 | 0.7091 |
| 12 | 1.1210 | 1.1150 | 1.0560 | 0.9436 | 0.7697 |
| 13 | 1.2300 | 1.2110 | 1.1430 | 1.0090 | 0.8279 |
| 14 | 1.3390 | 1.3050 | 1.2300 | 1.0693 | 0.8834 |
| 15 | 1.4670 | 1.4070 | 1.3200 | 1.1246 | 0.9362 |
| 16 | 1.6100 | 1.5010 | 1.4480 | 1.1751 | 0.9860 |
| 17 | 1.7780 | 1.6660 | 1.5790 | 1.2210 | 1.0330 |
| 18 | 1.9550 | 1.8710 | 1.7310 | 1.2630 | 1.0773 |
| 19 | 2.1390 | 2.1110 | 1.8960 | 1.3017 | 1.1192 |
| 20 | 2.3540 | 2.3540 | 2.0550 | 1.3380 | 1.1592 |
| 21 | 2.6280 | 2.5690 | 2.2570 | 1.3729 | 1.1978 |

-continued

| Indentation (RCFI-1 mm) | Cushion #1 (RCFI-1N) | Cushion #2 (RCFI-1N) | Cushion #3 (RCFI-1N) | Cushion #4 (RCFI-1N) | Cushion #5 (RCFI-1N) |
|---|---|---|---|---|---|
| 22 | 2.9640 | 2.7840 | 2.4350 | 1.4077 | 1.2358 |
| 23 | 3.3600 | 2.9520 | 2.5660 | 1.4436 | 1.2738 |
| 24 | 3.7860 | 3.1170 | 2.6500 | 1.4821 | 1.3131 |
| 25 | 4.3030 | 3.2720 | 2.6780 | 1.5248 | 1.3546 |
| 26 |  | 3.4250 | 2.6340 | 1.5735 | 1.3997 |
| 27 |  | 3.5560 | 2.5690 | 1.6299 | 1.4498 |
| 28 |  | 3.6800 | 2.4970 | 1.6961 | 1.5065 |
| 29 |  | 3.8080 | 2.3910 | 1.7741 | 1.5716 |
| 30 |  | 3.9730 | 2.3070 | 1.8661 | 1.6470 |
| 31 |  | 4.1410 | 2.3010 | 1.9743 | 1.7350 |
| 32 |  |  | 2.3410 | 2.1010 | 1.8376 |
| 33 |  |  | 2.5130 | 2.2487 | 1.9576 |
| 34 |  |  | 2.7240 | 2.4198 | 2.0974 |
| 35 |  |  | 2.9890 | 2.6169 | 2.2600 |
| 36 |  |  | 3.2820 | 2.8426 | 2.4484 |
| 37 |  |  | 3.6150 | 3.0995 | 2.6659 |
| 38 |  |  | 4.0790 | 3.3904 | 2.9160 |
| 39 |  |  |  | 3.7180 | 3.2022 |
| 40 |  |  |  | 4.0850 | 3.5285 |
| 41 |  |  |  |  | 3.8989 |

4.1.4 Lip Region

| Indentation (RCFI-1 mm) | Cushion #1 (RCFI-1N) | Cushion #2 (RCFI-1N) | Cushion #3 (RCFI-1N) | Cushion #4 (RCFI-1N) | Cushion #5 (RCFI-1N) |
|---|---|---|---|---|---|
| 0 | 0.1000 | 0.1000 | 0.1000 | 0.1000 | 0.1000 |
| 1 | 0.1620 | 0.2540 | 0.1530 | 0.1298 | 0.1163 |
| 2 | 0.2450 | 0.4900 | 0.2680 | 0.1982 | 0.1588 |
| 3 | 0.3700 | 0.7310 | 0.4350 | 0.2861 | 0.2228 |
| 4 | 0.5130 | 0.9620 | 0.5690 | 0.3915 | 0.3049 |
| 5 | 0.7080 | 1.2120 | 0.6890 | 0.5129 | 0.4020 |
| 6 | 0.9300 | 1.4480 | 0.7910 | 0.6492 | 0.5122 |
| 7 | 1.1840 | 1.6700 | 0.9620 | 0.7997 | 0.6340 |
| 8 | 1.4800 | 1.9290 | 1.1700 | 0.9641 | 0.7672 |
| 9 | 1.7210 | 2.1880 | 1.3880 | 1.1427 | 0.9118 |
| 10 | 1.9430 | 2.4750 | 1.6330 | 1.3363 | 1.0690 |
| 11 | 2.1790 | 2.7710 | 1.8870 | 1.5464 | 1.2407 |
| 12 | 2.4330 | 3.0900 | 2.1560 | 1.7750 | 1.4295 |
| 13 | 2.7340 | 3.3960 | 2.4470 | 2.0249 | 1.6388 |
| 14 | 3.1550 | 3.7190 | 2.7200 | 2.2996 | 1.8730 |
| 15 | 3.8810 | 4.0290 | 3.0070 | 2.6032 | 2.1370 |
| 16 | 4.7690 |  | 3.2890 | 2.9409 | 2.4367 |
| 17 |  |  | 3.6640 | 3.3186 | 2.7786 |
| 18 |  |  | 4.1680 | 3.7431 | 3.1702 |
| 19 |  |  |  | 4.2222 | 3.6197 |

4.1.5 Illustration of Cushion Behaviour

Figure 6:
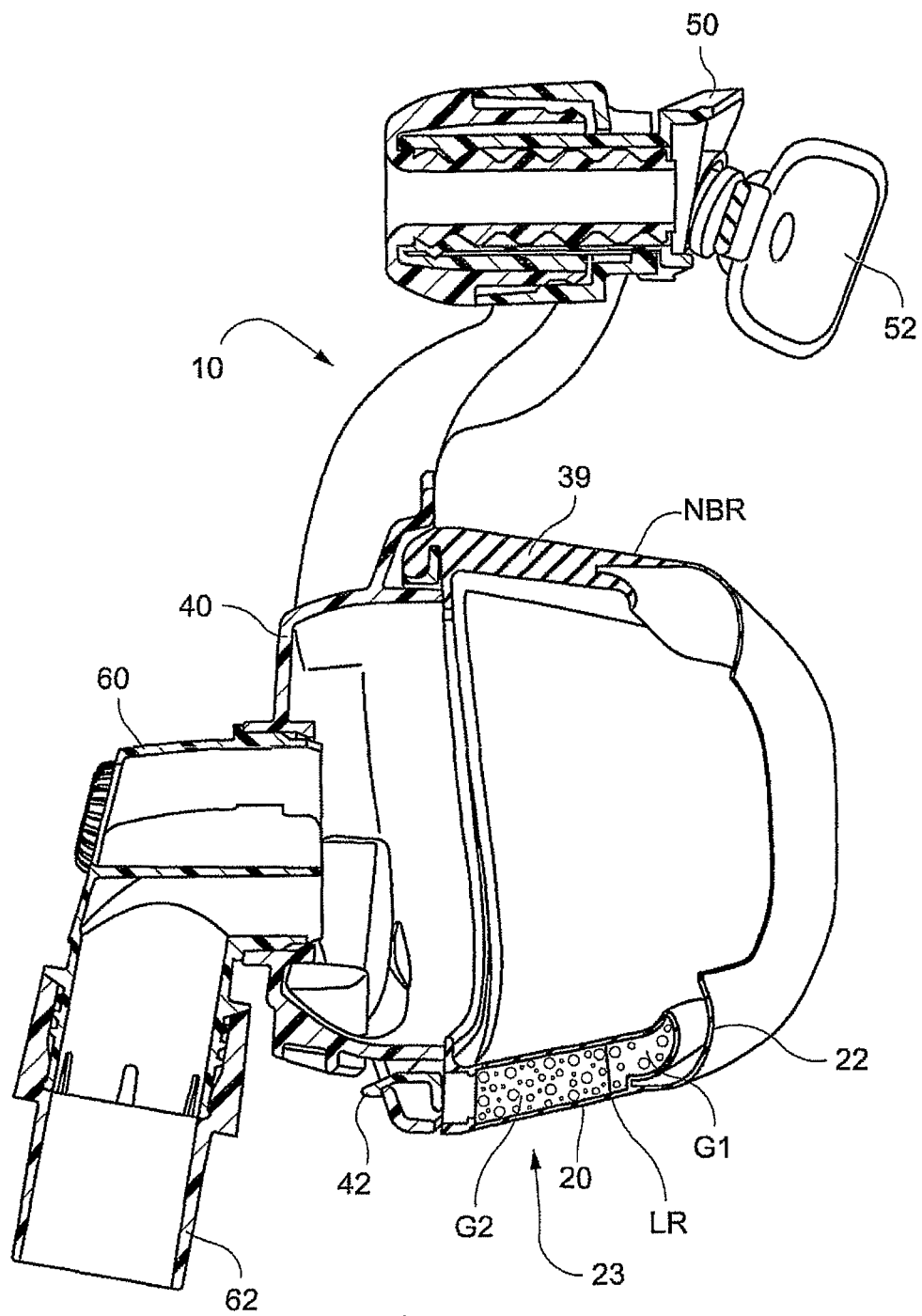
FIG. 6 is a cross-sectional view of the nasal mask assembly of FIG. 1 taken from the forehead support at the top to the swivel elbow at the bottom.
Figure 7:
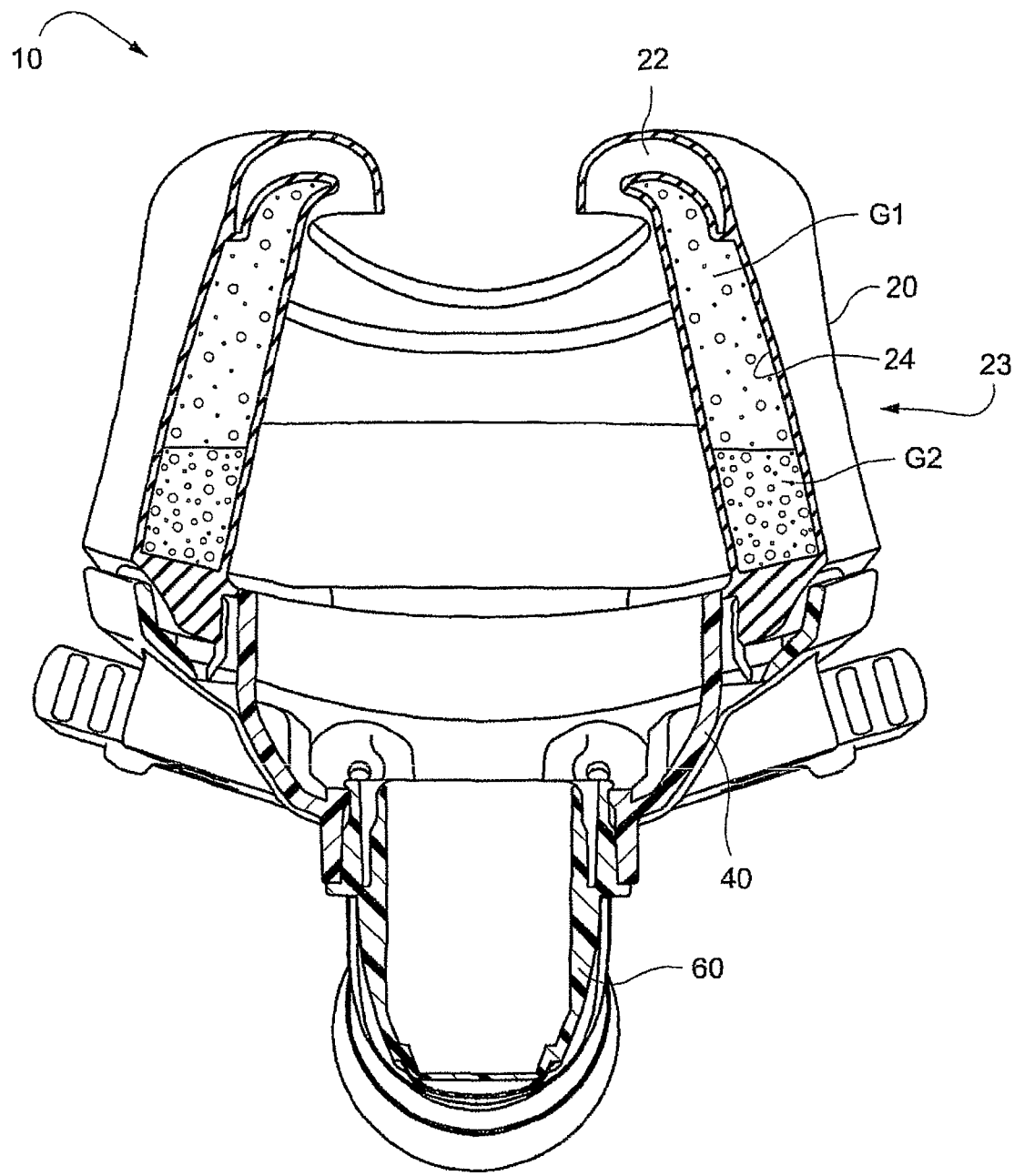
FIG. 7 is a top cross-sectional view of the nasal mask assembly of FIG. 1.
Figure 8:
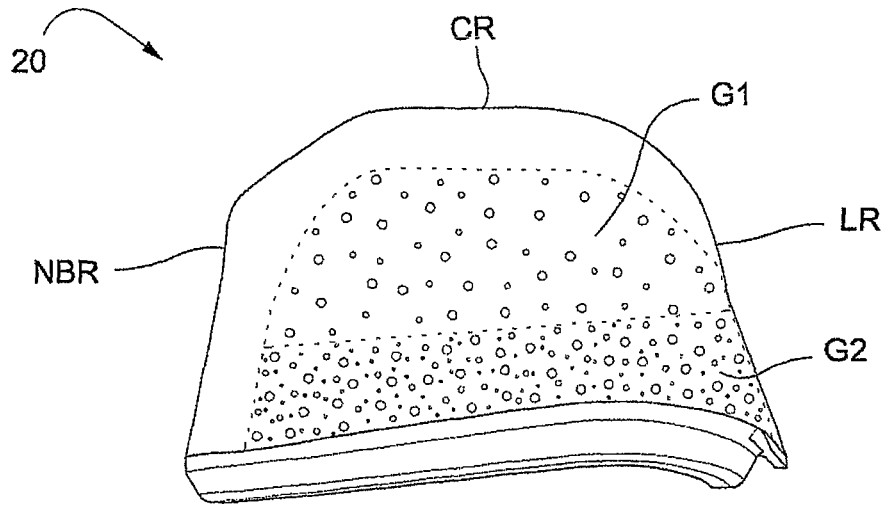
FIG. 8 is a side view of a flexible structure according to an embodiment of the present invention.
Figures 1, 47:
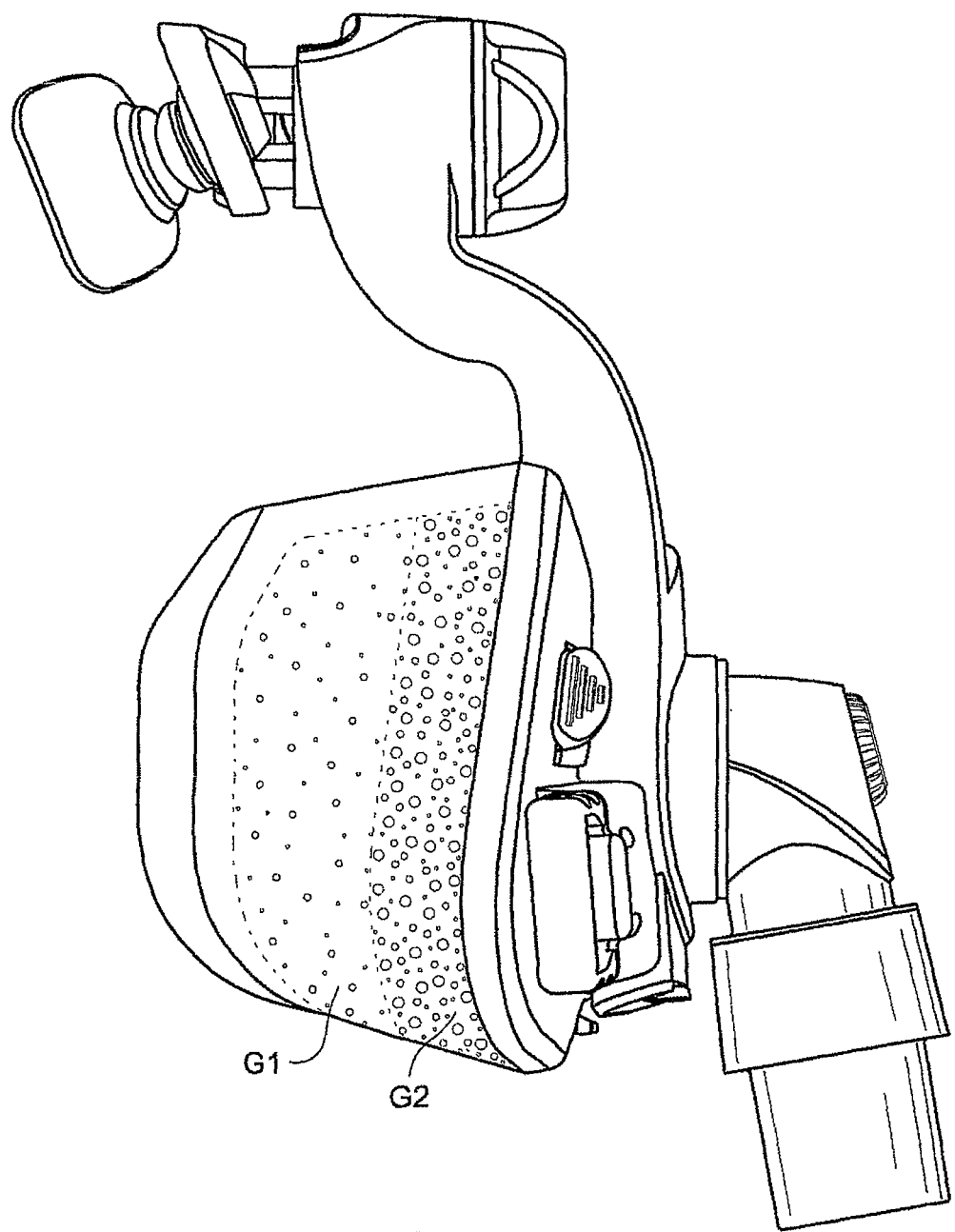
Figures 2, 47:
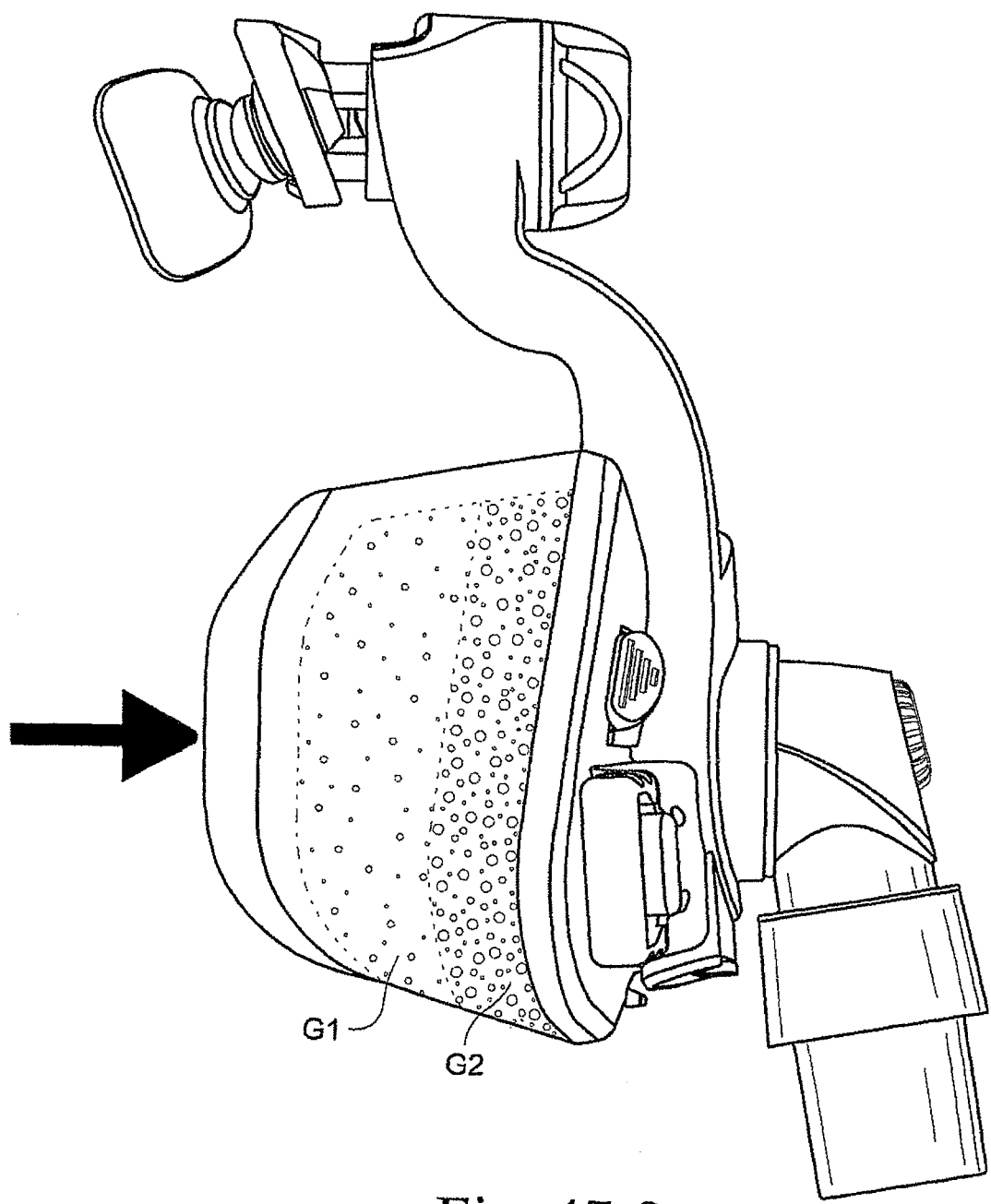
Figures 3, 47:
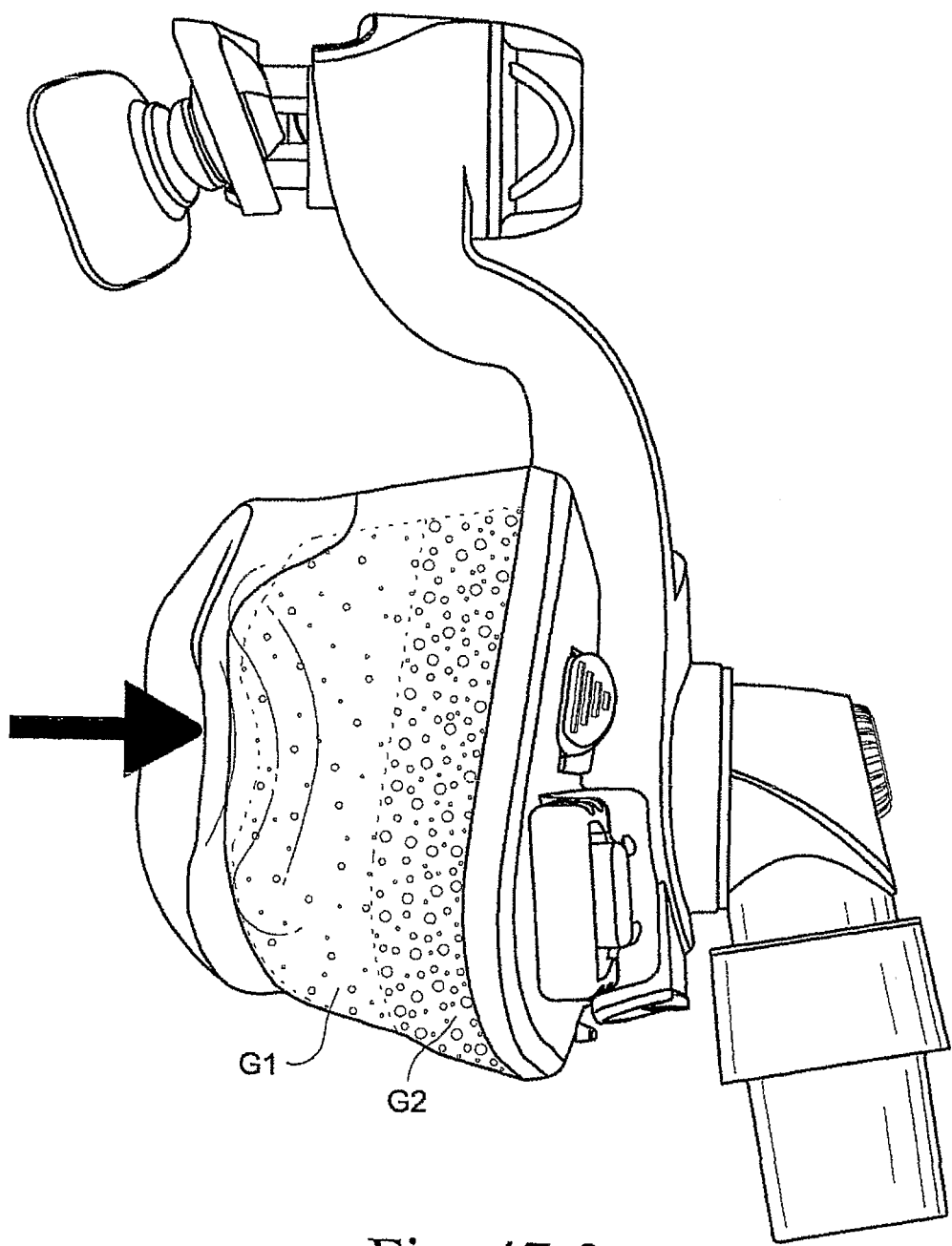
Figures 4, 47:
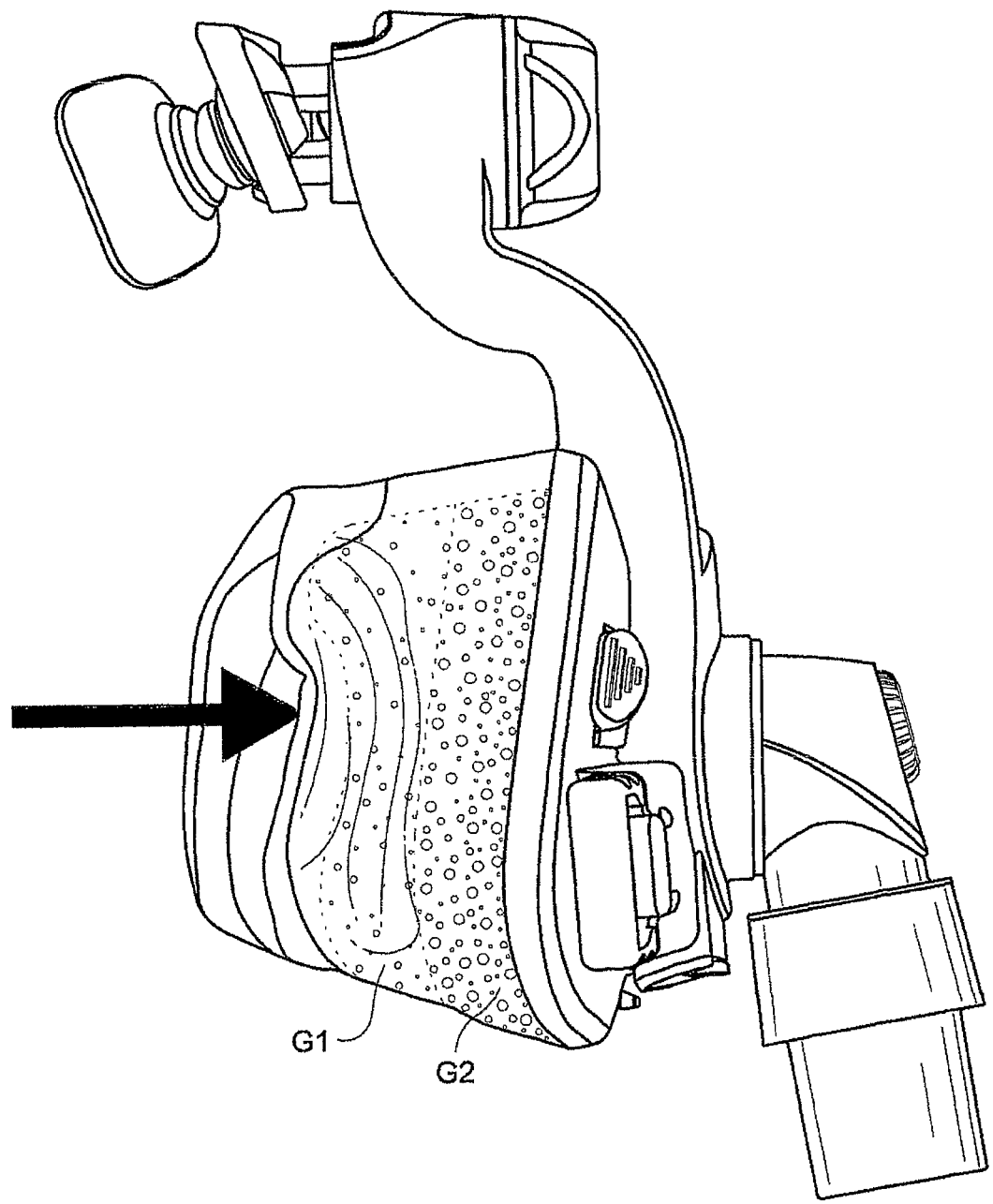
Figures 5, 47:
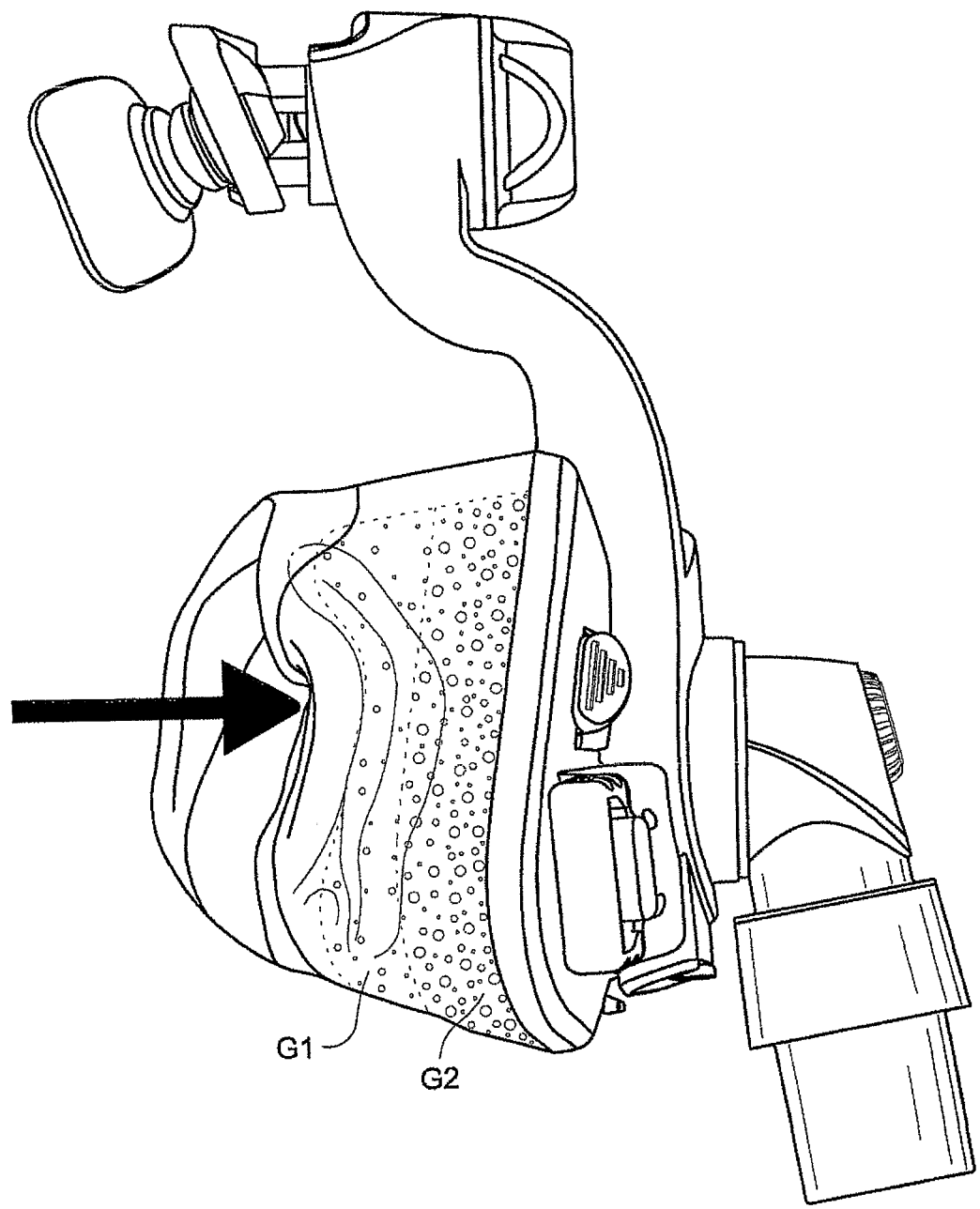
Figures 6, 47:
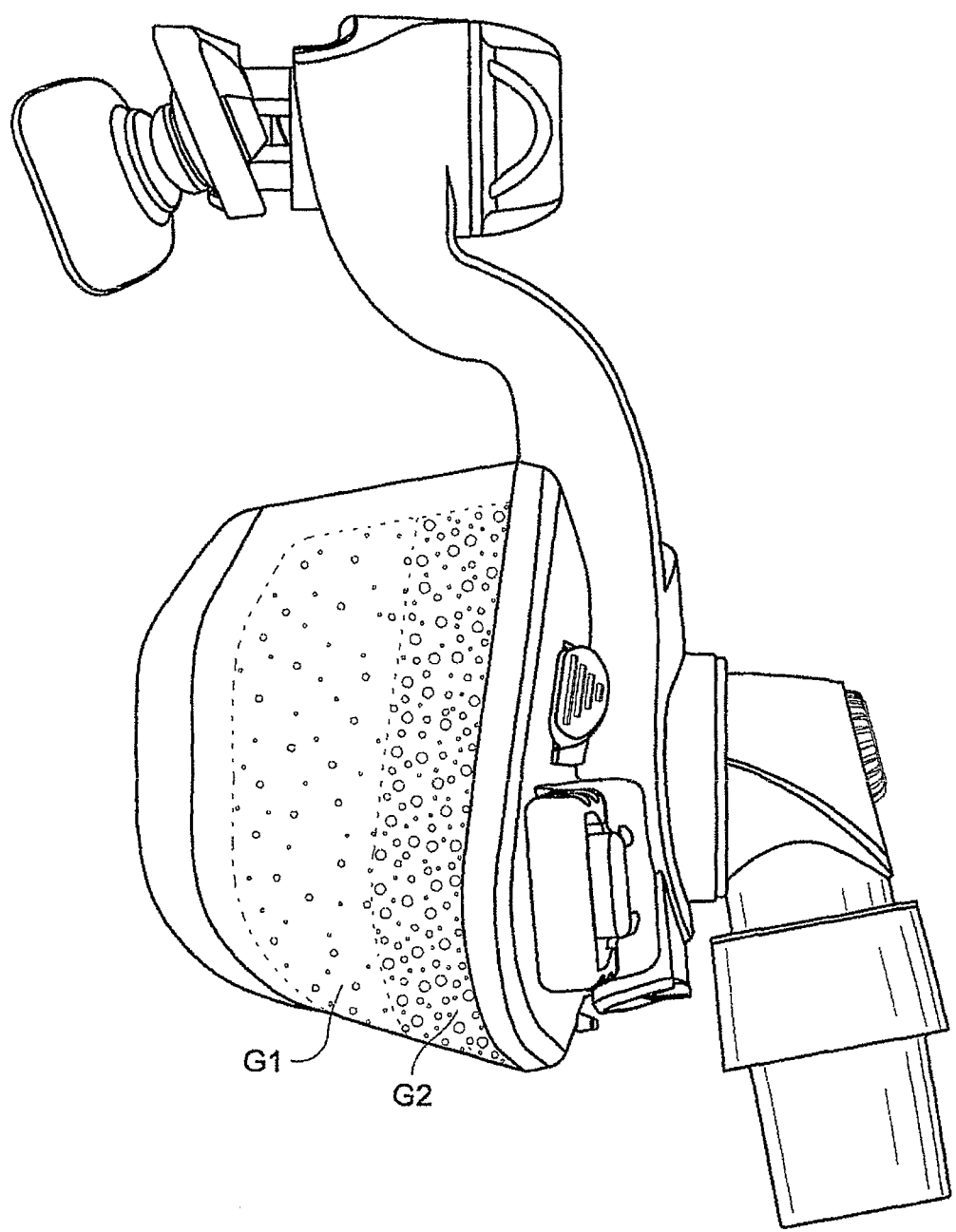

FIGS. 47-1 to 47-6 provides sequential views to illustrate an exemplary flexible structure being compressed. In this embodiment, the flexible structure includes first and second layers of gel G1, G2, with the softer, first layer G1 positioned closer to the patient's face in use.

FIG. 47-1 shows the flexible structure in its original shape before force is applied, and FIG. 47-2 shows the introduction of a force F to a cheek region of the flexible structure. FIGS. 47-3, 47-4, and 47-5 show deformation, bending, and/or compression of the flexible structure as force is progressively applied to the flexible structure. FIG. 47-6 shows the flexible structure in its original shape after the force is removed.

As illustrated, as force is progressively applied to the flexible structure, deformation, bending, and/or compression differs in the first layer G1 and the second layer G2. Thus, while the first and second layers G1, G2 are connected or coupled to one another within the bladder, the first and second layers may act somewhat independent from one another to a certain extent and may behave differently from one another.

When the compressive force is removed (FIG. 47-6), the gels G1, G2 resiliently return to their original shape. In an embodiment, a force may be applied to the flexible structure such that the first layer G1 is only deformed and the second layer G2 maintains its original shape, whereupon the first layer G1 resiliently returns to its original shape following removal of the force.

As shown in FIGS. 89-1 and 89-2 (FIG. 89-1 showing the flexible structure before force is applied and FIG. 89-2 showing the flexible structure after force is applied, e.g., engagement with the patient's cheek), the boundary or point between the first and second layers G1, G2 may act as a "hinge" point to encourage or promote bending of the flexible structure. That is, such hinge point may promote controlled, gradual bending of the first layer G1 relative to the second layer G2 as shown in FIG. 89-2. As illustrated, the flexible structure tends to bend at the hinge point rather than uncontrollably buckle and collapse.

This arrangement is in contrast to known bladders with a single gel G in which the bladder uncontrollably buckles and collapses towards or away from the breathing cavity (as indicated in dashed lines) upon the application of a compressive force as shown in FIG. 90.

Figure 4:
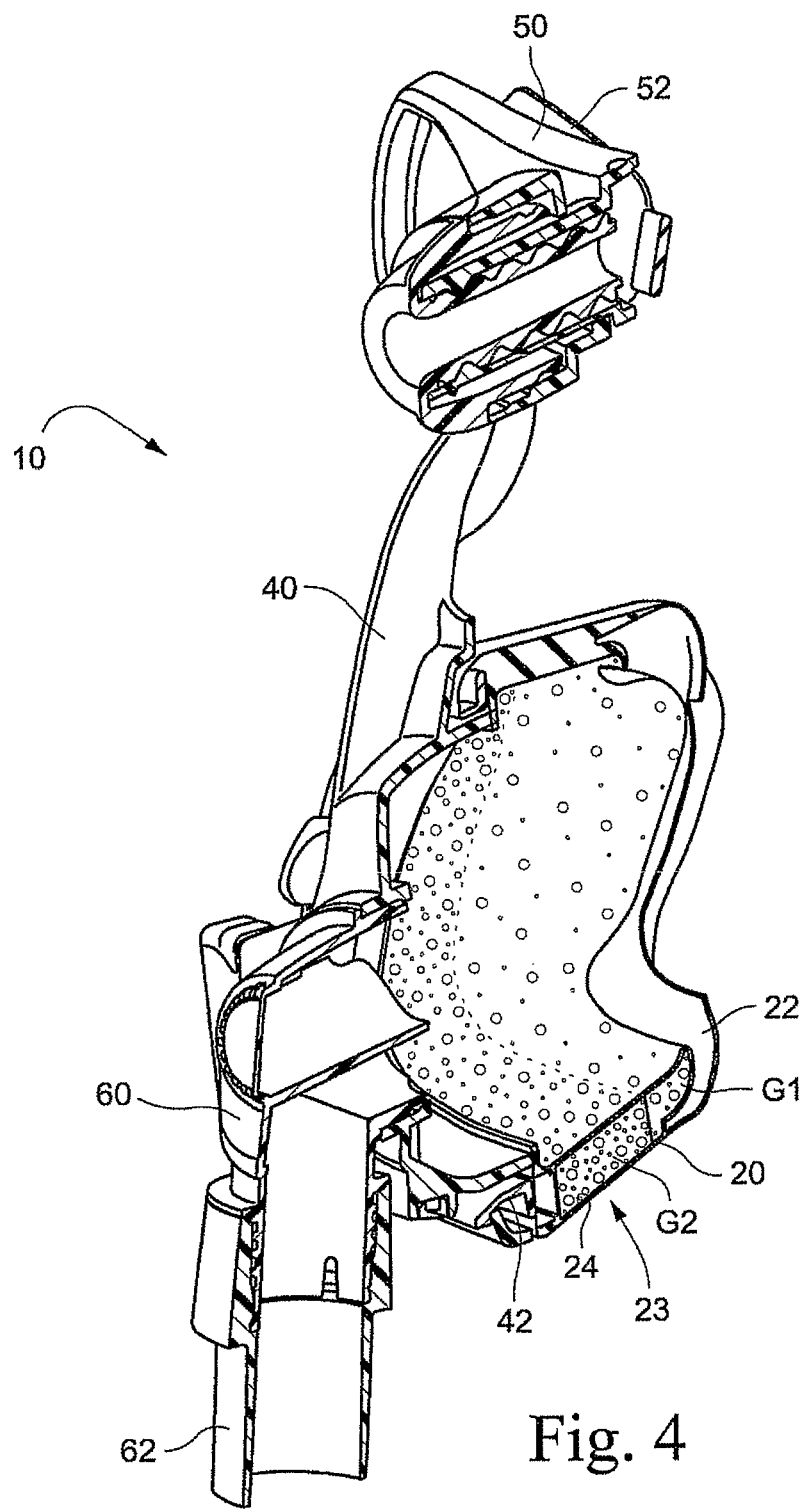
FIG. 4 is a perspective cross-sectional view of the nasal mask assembly of FIG. 1.
Figure 5:
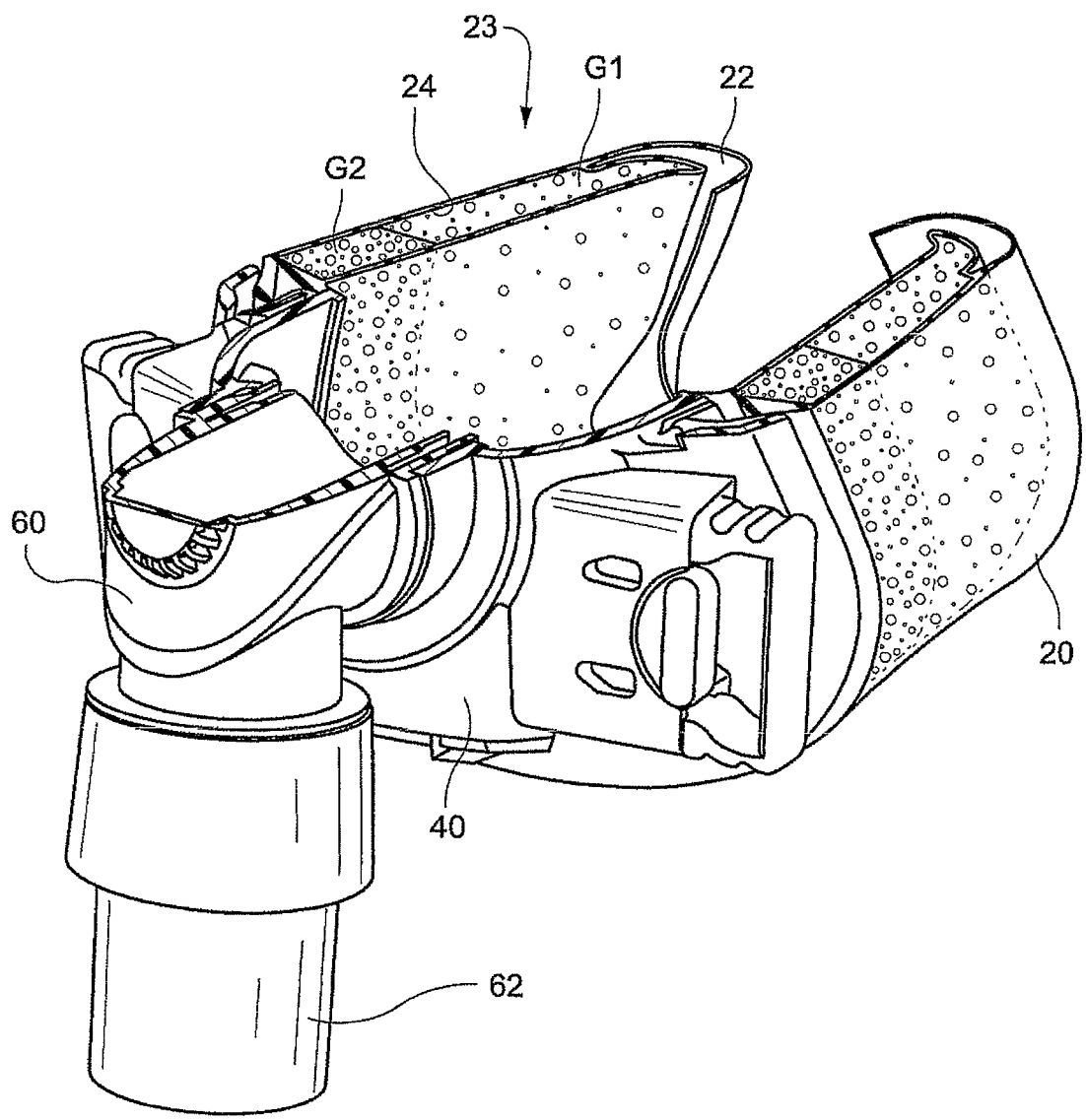
FIG. 5 is another perspective cross-sectional view of the nasal mask assembly through line 5-5 of FIG. 1.

Such arrangement allows deformation, bending, and/or compression to be controlled by adjusting the properties and/or fill level or height, or angle of the two gels. In addition, the wall thickness and/or wall angles defining the chamber and/or the membrane, etc. affects the properties. In the illustrated embodiment, the flexible structure gradually deforms or bends to a certain extent as force is applied, rather than rapidly deforming and buckling under load. Also, the properties of the flexible structure allow greater deformation at lower forces than flexible structures known in the art, e.g., see FIGS. 12-1 to 14-1. Such arrangement also makes less critical where the patient places the flexible structure on their face, in a lateral sense, as the flexible structure can readily conform to the patient's face and avoid bending away from the breathing chamber The properties of the flexible structure allow force to be distributed rather than concentrated at a certain region, which improves comfort in use. As shown in FIGS. 47-3 and 47-4, force F is applied at an intermediate point of the cheek region and then distributed over a larger portion of the cheek region, e.g., along the length of the cheek region as indicated by the ripples or undulations within the first layer G1, and beyond. Thus, the force associated with deformation may be less than those known in the art.

Also, in an embodiment, deformation of the softer, first gel G1 may be associated with the relatively smaller sloped portion of each curve on the graph (i.e., greater deformation with respect to load) while deformation of the harder, second gel G2 may be associated with the point on the graph at which the slope begins to more sharply increase (i.e., less deformation with respect to load).

4.2 Soft Materials

As described above, a flexible structure in accordance with the present technology may include regions having one or more spaces filled with one or more soft materials. Such regions of the flexible structure may provide a cushioning function, a sealing function, or both a cushion and sealing function. Different regions of the flexible structure may have different requirements and hence may be filled with different materials, or different combinations of materials, and or different amounts of materials. Such filling materials may be for example gels, or gel-like materials; foams and rubbers. The type of gel determines the shape and position of the cushion force response curves. Selecting the gel with different properties influences the level of cushion adaptability to the face. As will be now described, two mechanical properties of interest are the elasticity, and the viscoelasticity of such filling materials.

A more elastic gel will remain more constant over time and allow one region to maintain a different force response from a neighbouring region. This allows a maintained patient contact force profile and can alleviate pressure on certain regions of the face at cost of other supporting regions. Higher storage modulus (elastic) gels will ensure or allow: consistent loading during the course of therapy; defined force loading regions; more "springy" feel; more responsive to dynamic movement; and quicker setup time/quicker to established seal.

A more viscous gel will, over time, more evenly distribute the force over the region with which it is in contact. This may relieve localised pressure points. However, this attribute may impact the efficacy of the initial fit, as the fit may change as the cushion and gel material "adapts" to the face. Higher loss Modulus (viscous) gels will ensure or allow: ability to mold or adapt to facial profiles; more evenly distributed force loading regions; more fluidic and "damping" feel; and absorbed dynamic movement.

4.2.1 First Material (Very Soft Viscoelastic)

A first gel material in accordance with the present technology is very soft and visco-elastic. Such first gel material has an indentation resistance that is too soft to be measured using ASTM D2240 Durometer test methods Type OO and Type OOO. Hence using such test methods on the first gel material will give values of less than about 10, such as zero.

In one form, using the cone penetration tests according to ASTM D217 on the first gel material will yield values above 200, for example in the ranges of about 200 to about 350, preferably 250 to 320, more preferably around 280 to 310. In other forms the gel has cone penetration values between about 200 and 300, in the range of about 250 to about 300, in the range of about 215 to about 315, in the range of about 230 to about 270.

In this or another form, the first gel material may have a Young's Modulus of about 2-5 kPA. In one example the Young's Modulus is about 2.5 to about 4 kPA (this is the modulus in the relaxed state). The Young's Modulus is calculated by first measuring the durometer on any given standard scale (e.g., Shore OOO-S) or non-standard scale (e.g., REX GAUGE GO), and then converting the measured durometer according to known conversion techniques, see, e.g., "Dimensionless Durometry" published October 2008 by the University of Wisconsin-Madison Rheology Research Center 1513 University Avenue, Madison, Wis. 53706 USA referenced by "RRC 182". Specifically, using the Shore OOO-S equipment, a durometer of 3.3 (specimen in relaxed state) will result in a Young's Modulus calculation of 3.6 kPa, while using REX GAUGE GO equipment, a durometer of 9.2 (specimen in relaxed state) will result in a Young's Modulus calculation of 2.4 kPa.

The durometer/Young's Modulus ranges can vary as a result from testing either by hand or by using an operating stand and are accounted for in the ranges above. The durometer readings for the Shore OOO-S equipment were performed in conjunction with ASTM D2240-05 or D2240-02a, as the durometer measurements in this regard will not affect the calculated Young's Modulus values.

In this or another form, the first gel material may be a so-called "slow respond gel" which has a Rate of Return (the length of time the material takes to return to substantially the same thickness after being compressed by 50%) between 1 and 5 seconds, e.g., 2-3 seconds. Alternatively, the first gel material may be designed as a so-called "fast respond gel" which has a Rate of Return of 1 second or less.

Using the Dow Corning CTM1107, the first gel material has a reaction force of less than about 1N, preferably about 0.5N.

Using REX GAUGE GO test method on such first gel material will yield results around 5 to 15, preferably about 10.

The first gel material is viscoelastic, and has an Rt15 of about 20%, and an Rt30 of about 22%. In other forms, the Rt15 and Rt30 are in the range of about 15% to about 25%. (See Force Relaxation test methods defined in the last section of this specification)

A gel with a higher loss modulus will have more viscous properties, and may allow the product to form to the face overnight, or another period, and distribute cushion forces over the face more evenly (e.g., evenly over the nasal bridge, cheek and upper lip regions);

4.2.2 Second Material (Soft Viscoelastic)

A second gel material in accordance with the present technology is slightly harder than the first gel material, but is also visco-elastic.

When tested with ASTM Type OOO durometers, the second gel material will yield values in the range of 10 to 20.

In this or another form, when tested with ASTM D217 the material has Cone Penetration values in the range of 150 to 250, more preferably in the range of 175 to 225, more preferably in the range of 210 to 220.

In this or another form, using the Dow Corning CTM1107, the second gel material has a reaction force of between about 1.5N and about 2.5N, preferably about 1.8N to about 2.2N.

Using REX GAUGE GO test method on such second gel material, or another form will yield results around 40 to 50, e.g., 42 to 47, e.g., about 45.

In another example where the Young's Modulus is about 20 to about 40 kPA (this is the modulus in the relaxed state). Using the Shore OOO-S equipment, a durometer in the range of about 31-45 (specimen in relaxed state) will result in a Young's Modulus calculation in the range of about 20-36 kPa, while using REX GAUGE GO equipment, a durometer in the range of about 45-46 (specimen in relaxed state) will result in a Young's Modulus calculation in the range of about 19–20 kPa.

4.2.3 Third Material (Very Soft Elastic)

A third gel material in accordance with the present technology is very soft, and elastic.

The third gel material has a relative relaxation values Rt15 and Rt30 of less than about 5%, preferably less than about 2%.

In this or another form, the third gel material has a Type OOO durometer of less than about 20.

In this or another form, the third gel material has a Cone Penetration in the range of 200 to 350.

In this or another form, using the Dow Corning CTM1107, the third gel material has a reaction force of less than about 2N, preferably between about 0.5N and about 1.0N.

4.2.4 Fourth Material (Soft Elastic)

The fourth gel material has a relative relaxation values Rt15 and Rt30 of less than about 5%, preferably less than about 2%.

Using the Dow Corning CTM1107, the fourth gel material has a reaction force of between about 4N and about 5N, preferably about 4.5N.

In this or another form, when tested using Type OOO durometer, the fourth material has an indentation resistance of greater than about 45.

In this or another form, when tested with ASTM D217 the material has Cone Penetration values in the range of 150 to 250, more preferably in the range of 175 to 225, more preferably in the range of 210 to 220.

4.2.5 Fifth Material

A fifth material is a polyurethane foam with a density of about 30-90 kg/m3, e.g., 40-70 kg/m3. In an embodiment, the foam may include one or more similar properties to the foam described in PCT Publication No. WO 2008/011682, which is incorporated herein by reference in its entirety.

4.2.6 Sixth Material

A sixth material is a liquid silicone rubber with a low Type A durometer, for example in the range of less than about 10, e.g. less than about 5.

4.2.7 Seventh Material

A seventh material is a liquid silicone rubber with a Type A durometer in the range of about 35 to about 45, preferably about 38 to about 43.

4.2.8 Eighth Material

An eighth material is a liquid silicone rubber with a Type A durometer in the range of about 50 to about 80, preferably about 60 to about 70.

4.2.9 Ninth Material

A ninth filling material that could be used to fill a chamber of a cushion bladder is an oil or saline.

4.2.10 Tenth Material

A tenth filling material is a gel having a Type OOO indentation resistance in the range of about 20 to about 45. Such gel may be used to fill a chamber of a cushion bladder.

4.2.11 Eleventh Material

A tenth filling material is a gel having cone penetration in the range of about 5 to about 200. Such gel may be used to fill a chamber of a cushion bladder.

4.2.9 Commercial Sources of Suitable Gel Materials

Gels suitable for the present technology is a room-temperature vulcanizing two part silicone gel from Wacker, such as Wacker SilGel, Wacker Elastosil, or Dow Corning 7-9600.

WACKER SilGel (WACKER CHEMIE AG, MUNICH, GERMANY) is a pourable, addition-curing RTV-2 silicone rubber that vulcanizes at room temperature to a very soft silicone gel. It has a low viscosity, rapid heat cure, a pronounced inherent tack and has a flame retardant feature. Component B of WACKER SilGel contains the platinum catalyst, component A the crosslinker. Reducing the amount of component B will result in a harder, less tacky vulcanizate. The hardest formulation is achieved with a mixing ratio for A:B of approximately 1.5:1.

Another gel suitable for the present technology is DOW CORNING 7-9600 Soft Filling Elastomer (DOW CORNING CORPORATION, MICHIGAN, USA). This is a two-part platinum-catalyzed silicone elastomer based on a platinum catalyzed polydimethylsiloxane composition that will cure at a variety of temperatures from ambient to 140° C. See Dow Corning datasheet Ref. No. 52-1032A-01, which is incorporated herein by reference in its entirety.

Another gel suitable for the present technology is WACKER ELASTOSIL® P 26028 VP A/B. This a flowable, addition-curing two-part silicone rubber that cures to produce a crystal-clear gel.

Another gel suitable for the present technology is CYTEC CONATHANE® DPEG-30112. This a two-part polyurethane gel with a light amber color.

Another gel suitable for the present technology is CYTEC CONATHANE® DPEG-30103. This a two-part polyurethane gel with a light amber color.

Prior to curing, gels typically present as two-part mixtures, A and B, although gels can present as one or three part curing systems. By varying the mixing ratio of the two parts A and B, the resultant cured gel will have different properties, particularly relating to hardness.

4.3 Method of Manufacturing Flexible Structure

4.3.1 Seal-Forming Portion

A flexible structure in accordance with the present technology provides sufficient seal to maintain positive pressure therapy. There may be separate seal-forming and cushioning portions, or they may be formed or assembled into one piece. One type of seal-forming portion may be described as a compression, or gasket-type seal. Such a seal-forming portion may include a seal-forming surface that is pressed against the skin to effect a seal, for example transmitting headgear tension forces. Another type of seal-forming portion may be described as a "flap seal of thin material". The flap seal may be thin and able to conform to the contours of the patient's face when positive pressure is applied within the mask and when the flap is sufficiently close to the patient's face. Such a seal-forming portion may also be described as a "facial flap", comprising a relatively thin member of a flexible and semi-resilient material. Such a facial flap may respond to system pressure in the plenum urging it into tight sealing engagement with the face. See for example U.S. Pat. No. 3,330,273 (Bennett), the contents of which are hereby expressly incorporated by cross-reference. Adhesion may also be used to effect a seal.

In accordance with the present technology, a seal-forming portion may comprise compression-type seal, a flap-type seal or some combination. For example, one form of seal-forming portion may include a first flap-type seal at an outer end of the flexible structure and have a second, thicker stiffer flap adjacent the first flap. The second flap may include a space filled with a soft material. In one form of the present technology, different regions of the cushion as described above may include a flap type seal, and others a compression seal. For example, we prefer to use a flap-type seal in the nasal bridge region of the cushion, although in other forms, a compression-type seal may be used in the nasal bridge region.

4.3.2 Cushioning Portion

A flexible structure in accordance with one form of the present technology provides a soft cushioning function that may be compressed within a range of distance without an uncomfortable increase in force on the face of the patient, so called "bottoming out". Such functional behaviour may be provided by a range of physical structures and material properties. For example, a flexible structure may include a wall that is solid and manufactured from a silicone having a Type A durometer in the range of about 30 to about 80, more preferably in the range of about 35 to about 45. The wall may have an angled, curved or sickle shape to function as a spring, or may have some other shape to function as a spring. Another form of flexible structure in accordance with the present technology defines one or more interior spaces filled with soft material. In a preferred form, a flexible structure in accordance with the present technology comprises one or more chambers defining corresponding spaces that may be filled with a gel or gel-like material.

An advantage of this design is that the cushion is able to comfortably and effectively fit a wider range of facial shapes and sizes.

4.3.3 Integral LSR Moulded Cushion

In one form of the present technology the flexible structure comprises a cushion. The cushion is molded in a single piece from an elastic material such as silicone (e.g. LSR), for example as described in European Patent Application No. EP 08160921.6, filed 22 Jul. 22, 2008, the contents of which are hereby expressly incorporated by cross-reference. With reference to ASTM D2240-02a, preferably the silicone may have a durometer of 40 Type A. In another embodiment, the cushion may be molded in multiple pieces from silicone and joined together using an appropriate adhesive, e.g. glue, or for example by overmoulding.

An advantage of an LSR moulded cushion over for example vacuum-formed polyurethane bladder is that the LSR cushion may be less prone to breakage and the resultant leakage of gel material. The vacuum forming process may result in a bladder that is too thin on a face-contacting portion thereof, leading to breakages in that region. Furthermore the LSR cushion may be more readily washable at higher temperatures than a polyurethane bladder. Furthermore the LSR cushion may be less prone to "wrinkles" on its surface than a polyurethane bladder, such wrinkles may form leak paths and patient discomfort. A further advantage of an LSR moulded cushion over a polyurethane bladder is that the polyurethane bladder may be welded together leaving weld lines. Such weld lines may be located adjacent the sealing portion and may irritate a patient, may leave marks on a patient's face, or may be aesthetically unsightly. Another advantage of an LSR moulded bladder is that it may be more elastic than a polyurethane bladder allowing it to more readily stretch and conform to a patient's face.

In one form the cushion includes a single chamber. A chamber could be formed as a closed vessel that may be filled with a gel, by piercing for example.

Preferably in the illustrated embodiment, the cushion is structured to include a seal-forming flap or membrane 22, and a cushioning region 23 defined by a chamber 24 that is filled with a soft material such as one or more gels (e.g., first gel G1 and second gel G2 as shown in FIGS. 1-11). In the illustrated embodiment, the cushion provides a nasal interface with a nasal bridge region NBR, cheek region CR, and lip region LR. However, the cushion may be adapted for any suitable interface type, e.g., full-face.

Figure 20:
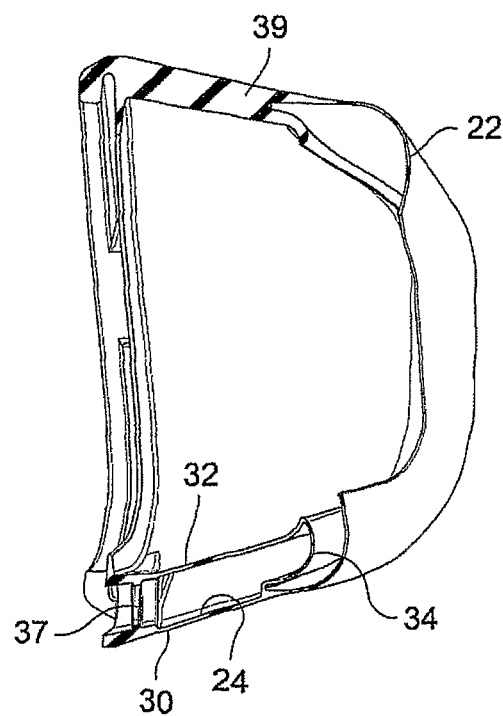
FIG. 20 is a cross-sectional view through line 20-20 of FIG. 15.
Figure 21:
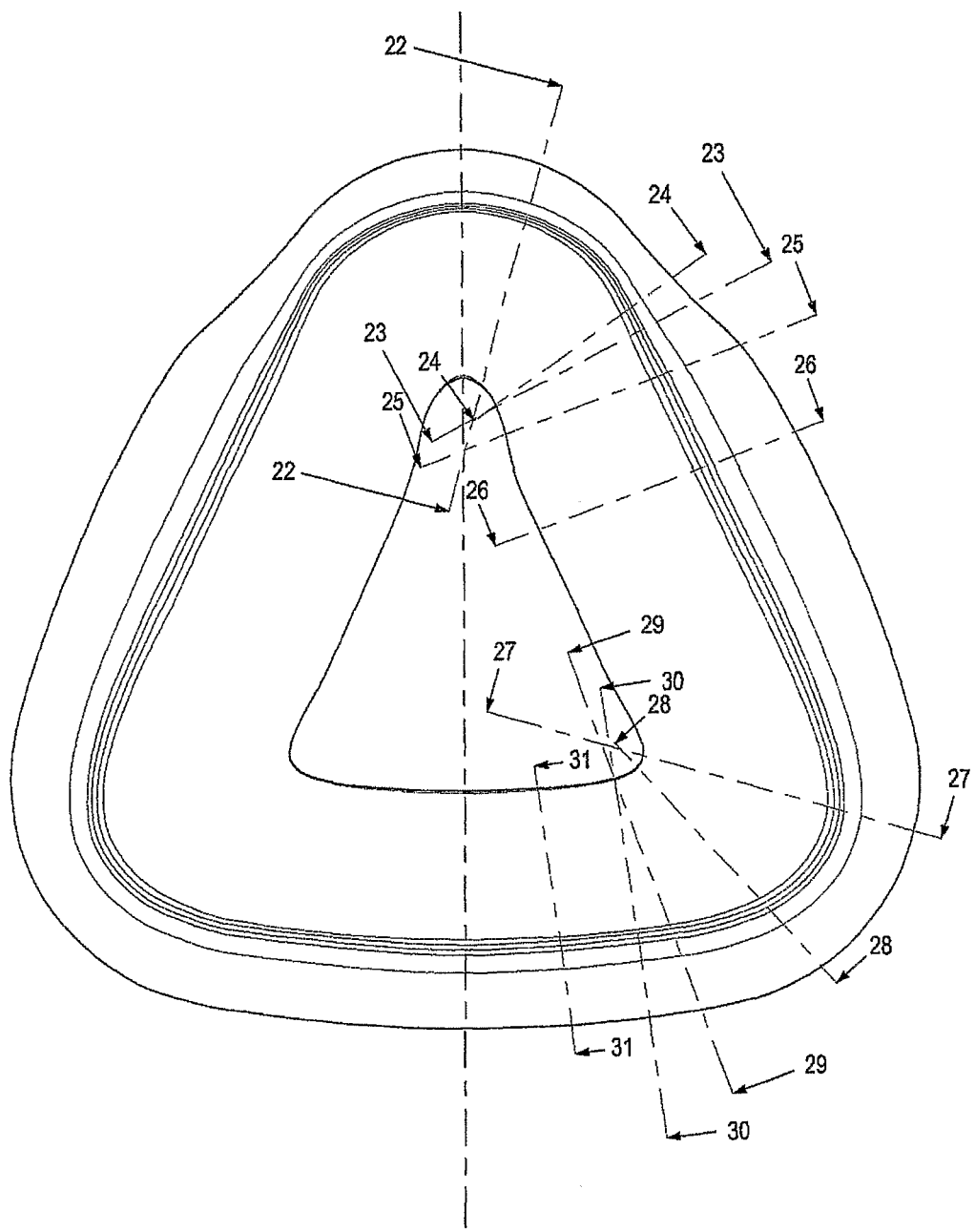
FIG. 21 is a view showing a patient contacting side of the flexible structure of FIG. 15 showing cross-section lines.

As shown in FIG. 20 for example, the chamber 24 includes an outer wall 30, an inner wall 32, and an arcuate upper wall 34 that interconnects the outer and inner walls, so that the outer wall, inner wall, and upper wall define the chamber for gel. The membrane 22 substantially covers the chamber 24 and provides a sealing structure. It should be appreciated that the wall thicknesses (e.g., in the range of 0.25 to 0.75 mm) may be the same or varied. In embodiments, the chamber may be referred to as a space or cavity and may be open or closed and may include one or more dividing walls. FIG. 91 is a schematic view showing the outer and inner walls 30, 32 and chamber 24. In an example, each wall 30, 32 may have a thickness $t_w$ of about 0.25-0.75 mm (e.g., 0.4-0.6 mm) and the chamber 24 may have a thickness $t_{ch}$ of about 5-10 mm (e.g., 6-8 mm). The combined thickness $t_{total}$ of the outer wall, inner wall and chamber may be greater than about 5 mm, e.g., about 5-12 mm, greater than about 7.5 mm, about 10 mm. The height H of the chamber may be greater than 5 mm, e.g., 5-10 mm, greater than 10 mm, e.g., 10-20 mm, or greater than 20 mm, e.g., 20-30 mm, in a cheek region and/or greater than 5 mm, e.g., 5-10 mm, greater than 10 mm, e.g., 10-20 mm, or greater than 20 mm, e.g., 20-25 mm, in a lip/chin region. In an example, one or more of the above dimensions may be selected to avoid buckling which may occur with thinner and/or taller walls of the cushion which will easily buckle in use leading to uncomfortable application of forces to the patient's face with little strap tension adjustment.

A cap or end wall 36 (e.g., see FIG. 23) may be provided to the base of the chamber 24 to enclose and retain the one or more gels within the chamber. The cap may be integral or a separate component. A gate or hole 37 is provided in the cap 36 (e.g., see FIGS. 16, 20, 33, and 37) to allow injection of the one or more gels into the chamber (e.g., gate may be formed before cap is attached). The gate 37 may be sealed once the gel(s) have been injected, the gate 37 may be sealed with a second cap. The cap 36 may provide a channel 38 around its perimeter that is structured to receive a cushion clip for attaching the flexible structure to the mask frame. However, the cap may provide other suitable structure for interfacing or otherwise attaching with the mask frame. In addition, a sealing lip 41 is provided to the base of the chamber, such sealing lip adapted to engage and form a seal with the mask frame in use.

Figure 9:
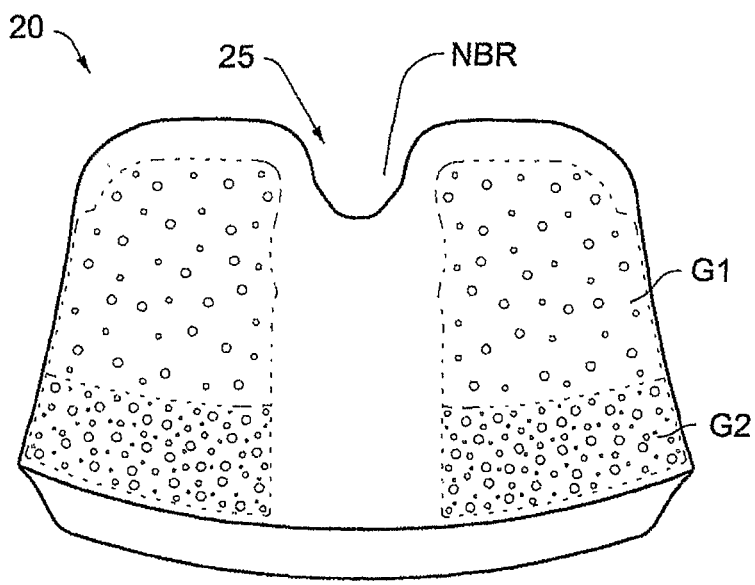
FIG. 9 is a top view of the flexible structure of FIG. 8 showing the nasal bridge region.
Figure 10:
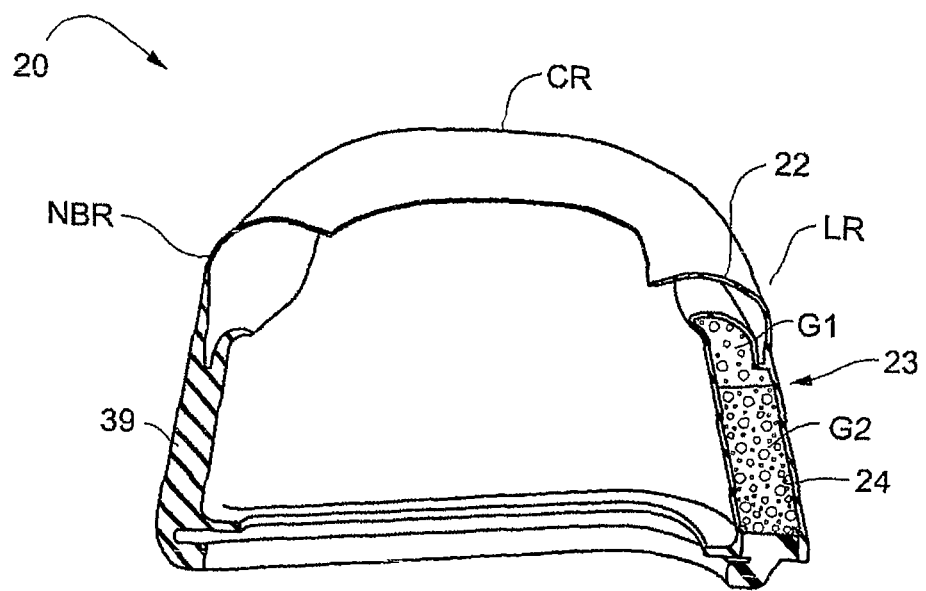
FIG. 10 is a cross-sectional view of the flexible structure of FIG. 8 taken from the nasal bridge region to the lip region.
Figure 11:
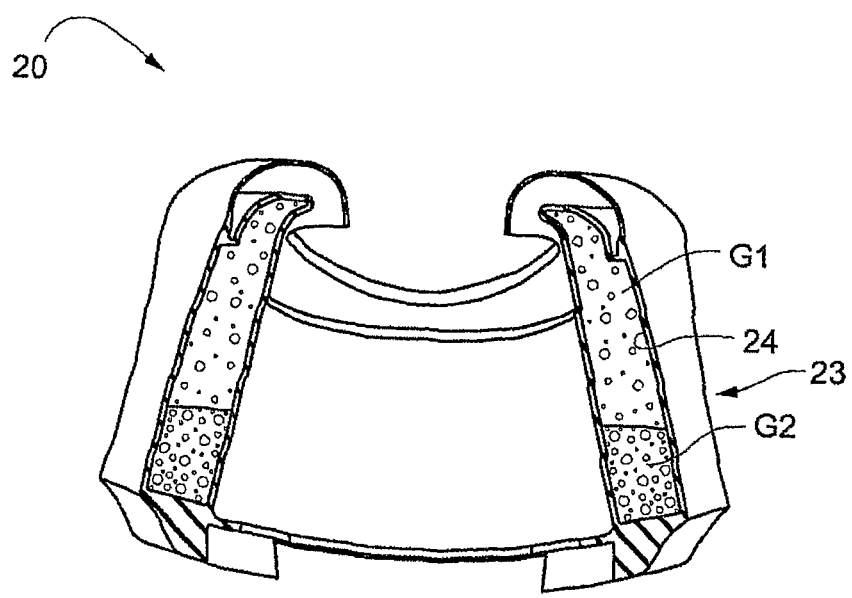
FIG. 11 is a cross-sectional view of the flexible structure of FIG. 8 taken in the cheek region.

In the illustrated embodiment, the chamber 24 is not provided about the entire perimeter of the flexible structure. As best shown in FIGS. 6 and 10, the chamber for one or more gels is not provided in the nasal bridge region NBR of the flexible structure. That is, the chamber for one or more gels is provided in cheek and upper lip regions CR, LR of the flexible structure and a solid silicone portion 39 is provided in the nasal bridge region NBR. Also, as shown in FIG. 9, a notch 25 is provided in the nasal bridge region NBR for receiving the patient's nasal bridge. However, in alternative embodiments, the chamber may extend around the entire perimeter of the cushion, and may be provided in one or more selected portions of the cushion.

The solid silicone portion in the nasal bridge region adds stiffness to the flexible structure to enhance lateral stability of the flexible structure in use, e.g., reduce side to side movement. In another form, solid silicone or other rubber portions may be included in other regions. For example, there may be a solid silicone piece between lip and cheek portions.

In another example, an air layer may be provided between gel layers or as a substitute for one of the gel layers, e.g., in one or more selected portions of the cushion. In another example, an air chamber (with no gel) may be provided to one or more selected portions of the cushion. In another example, a release agent may be provided between gel layers to allow relative movement between gel layers in use. In another example, the left and right cheek regions of the cushion may be asymmetric, e.g., one of the cheek regions may include different properties and/or dimensions than the other of the cheek regions.

Preferably the cushion includes an integrally moulded portion adapted to be removably and sealably engaged with a mask frame, e.g., for cleaning, replacement, etc.

Shape

FIGS. 15-31 illustrate various views and cross-sections of a flexible structure according to an embodiment of the present invention. Similar reference numerals have been used to indicate similar portions as described above. In this embodiment, as best shown in FIGS. 22-31, the outer and inner walls 30, 32 of the chamber are substantially straight or planar along its length.

The height of the cushion wall represents a distance that the cushion may compress prior to bottoming out. In a cheek region, a preferred form of cushion has a wall height in the uncompressed state of greater than about 18 mm, more preferably greater than about 25 mm, more preferably in the range of about 30 mm to about 40 mm. We have found this preferred height range leads to improved comfort so that the cushion does not bottom out too readily in use, however other heights may be used depending on the gel material and shape and configuration of the bladder. In an example, the wall height may be greater than about 10 mm, e.g., 10-50 mm, 15-40 mm, 20-30 mm, 25-40 mm. It is noted that such cushion wall height measurements exclude heights of relatively incompressible portions such as a solid clip, or a thickened cushion-to-frame portion.

As shown in FIGS. 21 to 31 for one form of cushion, and FIGS. 38 to 46 for another form of cushion, a preferred form of cushion may include an inwardly curved sealing flap 22 (e.g., about 2 cm long). Such a sealing flap is preferably integrally moulded with a wall portion. Preferably an outer end of the flap 22 is attached to a wall on an exterior side of the cushion For a nasal cushion in a lip region, a preferred form of cushion has a wall height in the uncompressed state of greater than about 10 mm, more preferably greater than about 15 mm. We have found that in certain forms, if a cushion is too short it may bottom out and feel hard on the lip region. However, in other forms a shorter structure may be used. In an example, the wall height may be greater than about 5 mm, e.g., 5-20 mm, 5-15 mm, 10-15 mm.

In other forms, the cushion may be structured and arranged to cantilever, or overhang (e.g. on an inner side, or an outer side) a more rigid frame wall so that in compression it does not bottom out with a small indentation. In such an overhanging or cantilevered cushion, shorter wall regions may be used.

A further advantage of a cushion in accordance with the present technology is that in compression it tends not to buckle and rapidly collapse as some prior art cushions that are for example, overly high and thin walled. Such buckling and collapse behaviour may lead to a rapid rise in force on the face. Instead, the preferred form of cushion tends to more gradually compress.

Another aspect of a cushion wall in accordance with one form of the present technology is that at least a portion of the cushion wall, e.g., the face contacting portion, is angled inwardly. Alternatively, the cushion wall have an alternative wall configuration (e.g., straight wall, outwardly angled wall) but structured (e.g., different inner and outer wall thicknesses) to promote inward bending into the breathing cavity upon the application of force in use. In an example, a substantial portion of the cushion wall if not the entire cushion wall is angled. For example, in this form, the cushion walls have an inwards slope from the frame side to the patient side of the cushion when viewed in cross-section. See for example, FIG. 20 and FIGS. 21-31. This leads to greater control of deflection of the cushion. Furthermore it may allow different cushion sizing wherein the walls may present at different angles to a large face compared to a small face enabling the same frame to be used on a wider range of faces.

In a cushion that has relatively straight walls, the cushion is very sensitive to the angle of patient contact with the cushion and relies on contacting the exact mid-point of the wall. When the first point of patient contact in such a mask is not at the mid point, the cushion may uncontrollably collapse or buckle, potentially leading to patient discomfort.

FIGS. 32-46 illustrate various views and cross-sections of a flexible structure according to an embodiment of the present invention. Similar reference numerals have been used to indicate similar portions as described above. In this embodiment, as best shown in FIGS. 39-46, the outer and inner walls 30, 32 of the chamber are curved or arcuate along its length (for example in one form concave or curved inwardly towards the breathing chamber, in another form convex or curved outwardly). In another form, a series of small straight surfaces may be used.

The curved walls are structured promote controlled bending or folding of the flexible structure as described above with respect to FIG. 89-2.

It should be appreciated that the flexible structure may be provided in different sizes, e.g., small, medium, and/or large.

Filling & Sealing

In a preferred form the illustrated embodiment, the chamber is filled with two layers of gel G1, G2, each layer being made from a gel of different properties. However, the chamber may be filled with one, or several layers. However, the chamber may be filled with a single layer of gel or the chamber may be filled with more than two layers of gel, e.g., 3 layers, 4 layers, 5 layers, or more. As illustrated, the layers are stacked in the axial sense (e.g., see FIGS. 1-11). However, the layers may be arranged in other suitable manners, e.g., layers extending parallel or perpendicular to the chamber axis. Each in an embodiment, each layer is separated by the next by ensuring the gel is sufficiently cured before the addition of the next layer. In an embodiment, some mixing between the layers may be allowed (e.g., before first layer cures) to provide more gradual change between layers. In another form, layers may be arranged not to bond together to provide movement between layers.

The following table provides exemplary parameters for two different embodiments of a flexible structure. Each embodiment includes a similar silicone component with similar side wall thicknesses, but the chamber is filled with different gels, i.e., one embodiment using Soft materials #1 and #2 and the other embodiment using Soft materials #3 and #4. In another form the fifth, sixth, ninth, tenth and or eleventh materials may be used.

In an embodiment, the height of the first gel to the second gel may be expressed as a ratio. For example, a ratio of height of the first gel to the second gel in a lip region may be different, e.g., lower or higher, than the corresponding ratio in a cheek region. For example, the lip region ratio may be in the range of about 0.25 to about 0.6, and a ratio of height of the first gel to the second gel in a cheek region may be in the range of about 0.5 to about 1.7.

| Parameter | Example 1 | Example 2 |
| --- | --- | --- |
| Layer 1 (e.g., G1) | Soft material #1 | Soft material #3 |
| Layer 2 (e.g., G2) | Soft material #2 | Soft material #4 |
| Inner wall thickness | 0.4 mm to 0.6 mm | 0.4 mm to 0.6 mm |
| Outer wall thickness | 0.4 mm to 0.6 mm | 0.4 mm to 0.6 mm |
| Layer 1 height lip region | 4 mm to 7 mm | 4 mm to 7 mm |
| Layer 1 height cheek region | 10 mm to 15 mm | 10 mm to 15 mm |
| Layer 1 height nasal bridge | 0 mm | 0 mm |
| Layer 2 height lip region | 12 mm to 15 mm | 12 mm to 15 mm |
| Layer 2 height cheek region | 9 mm to 18 mm | 9 mm to 18 mm |
| Layer 2 height nasal bridge region | 0 mm | 0 mm |
| Inward wall angle nasal bridge | 9° | 9° |
| Inward wall angle lip region | 13° | 13° |
| Inward wall angle cheek region | 11.4° | 11.4° |

The force response curves (e.g., see FIGS. 12-14) may be shifted to the right by, for example, increasing the height of the soft gel (first gel layer 1) relative to the height of the harder gel (second gel layer 2).

An advantage of using two gel layers, as shown in FIGS. 47-1 to 47-6, one can control a "hinge" point, that is a point located between the two layers. Such a hinge point may assist in controlling buckling and or bending behaviour. With such a hinge point, when the cushion is compressed, it will tend to bend at that point rather than uncontrollably buckle and collapse.

In an alternative embodiment, one or more layers of gel (e.g., G1 or G2, especially G2) may be substituted with a low durometer silicone (e.g., Type A durometer less than about 5), e.g., such as the low durometer silicone described above in section 4.2.6. Such arrangement may promote the bending about the "hinge" point as described above.

Also, in an alternative embodiment, gel layers may be formed so that they are not parallel to one another. For example, as shown in FIGS. 92-1 and 92-2, a first gel layer G1 may be cured within the chamber (FIG. 92-1), tilt the cushion (e.g., by an angle α) after the first gel layer cures, and then fill the chamber with a second gel layer G2 such that the second gel layer will cure at a non-parallel angle with respect to the first gel layer (FIG. 92-2).

4.3.4 Alternative LSR Configurations

The following outlines the properties that influence the force response curves:
Chamber Wall Thickness
Chamber Wall Heights
Chamber Wall Curvature or Angles Chamber wall curvature or angle of the chamber wall relative to the facial contact point will influence the degree of buckling.

Chamber Facial Contact Point

Similar to the chamber wall curvature or angle, changing the facial contact point relative to the chamber wall affects the buckling of the cushion component. This buckling influences the force response curve.

Chamber Material Hardness

The chamber material hardness will affect the overall force response curve for all regions. Increasing the material hardness and thickness will increase the stiffness and rebound of the cushion.

An embodiment example is a harder chamber material with a soft gel may provide a given force response curve that is equivalent to a softer chamber material with a harder gel. Alternatively, the force response curve can be shifted to the right (softened) by maintaining the gel hardness while decreasing the chamber material hardness—the force response curve will shift across all regions.

In one form the chamber is manufactured using a rubber material having an indentation resistance in the range of 30-50 Type A (ASTM D2240)

The "feel" of the flexible structure on the patient's face is influenced by a number of parameters in each region. The parameters or properties affect the force response curve and is detailed in the following sections. The combination of any one or more parameters below can affect the force response curve.

Exemplary parameters include: properties of each of the gel layers; fill level, angle or height of each gel layer (in combination with the gel mixing ratios affects feel); wall thickness of the chamber (decreasing thickness provides softer, more flexible feel); wall heights; and wall angles (e.g., inward angles affect the extent of roll of the wall under compression).

Figure 22:
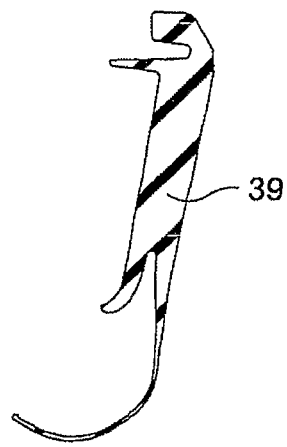
FIG. 22 is a cross-sectional view through line 22-22 of FIG. 21.
Figure 23:
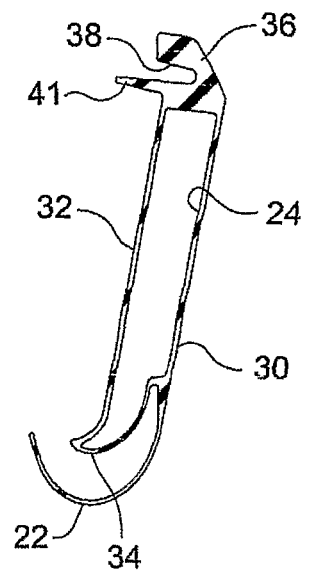
FIG. 23 is a cross-sectional view through line 23-23 of FIG. 21.
Figure 24:
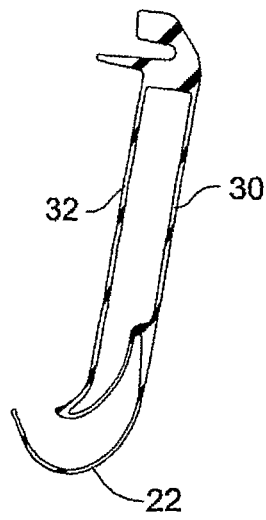
FIG. 24 is a cross-sectional view through line 24-24 of FIG. 21.
Figure 25:
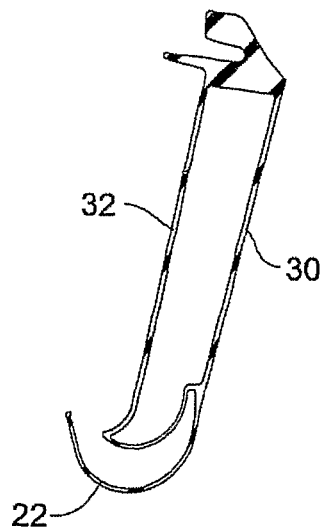
FIG. 25 is a cross-sectional view through line 25-25 of FIG. 21.
Figure 26:
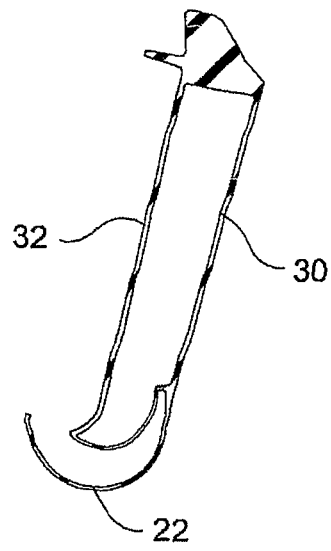
FIG. 26 is a cross-sectional view through line 26-26 of FIG. 21.
Figure 27:
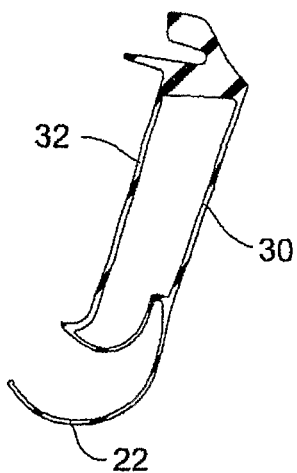
FIG. 27 is a cross-sectional view through line 27-27 of FIG. 21.
Figure 28:
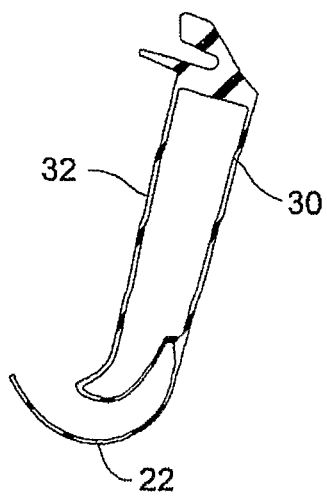
FIG. 28 is a cross-sectional view through line 28-28 of FIG. 21.
Figure 29:
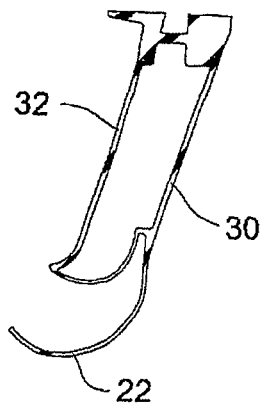
FIG. 29 is a cross-sectional view through line 29-29 of FIG. 21.
Figure 30:
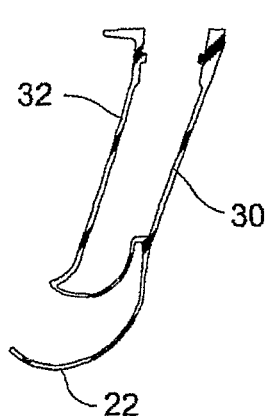
FIG. 30 is a cross-sectional view through line 30-30 of FIG. 21.
Figure 31:
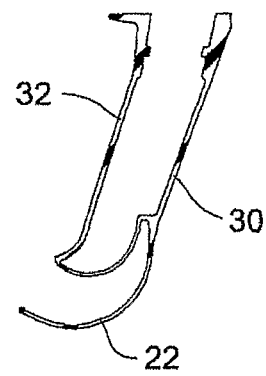
FIG. 31 is a cross-sectional view through line 31-31 of FIG. 21.
Figure 32:
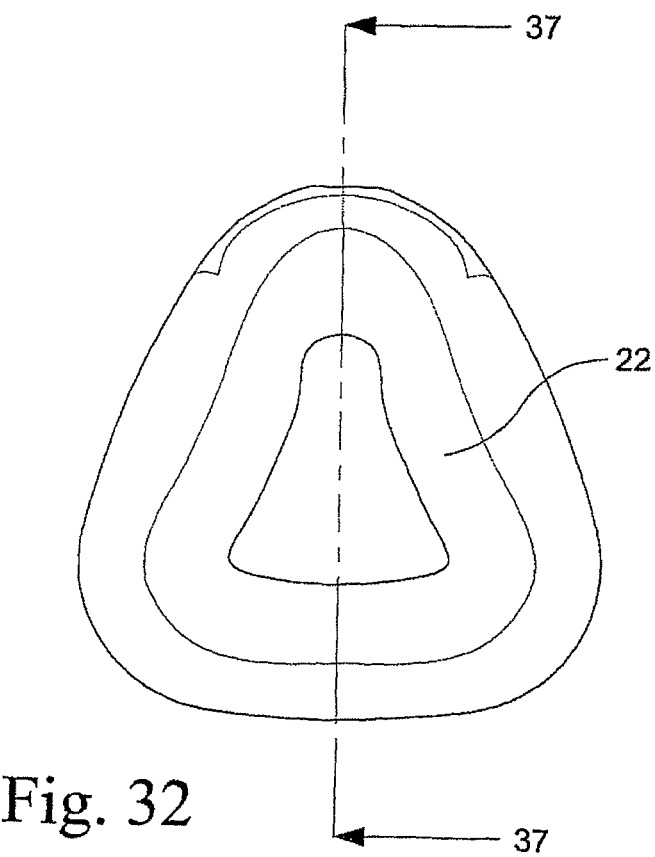
FIG. 32 is a view showing a patient contacting side of a flexible structure according to an embodiment of the present invention.
Figure 33:
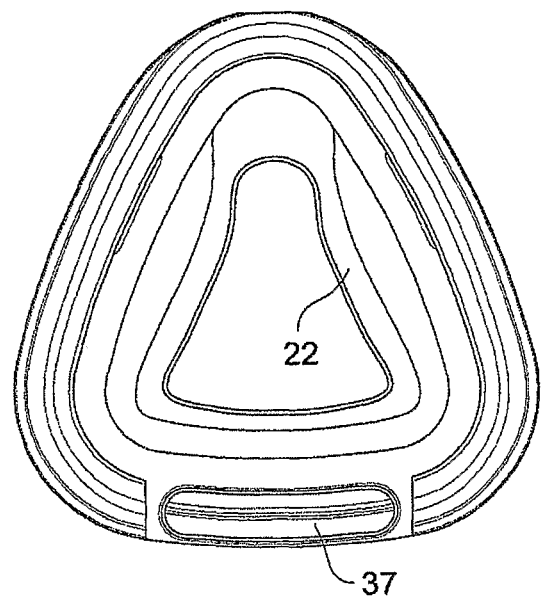
FIG. 33 is a view showing a frame contacting side of the flexible structure of FIG. 32.
Figure 34:
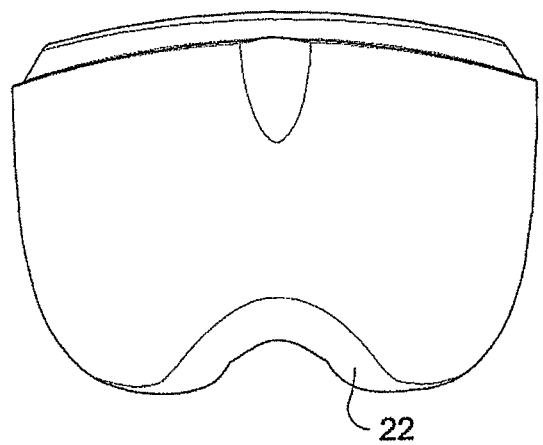
FIG. 34 is a top view of the flexible structure of FIG. 32.
Figure 35:
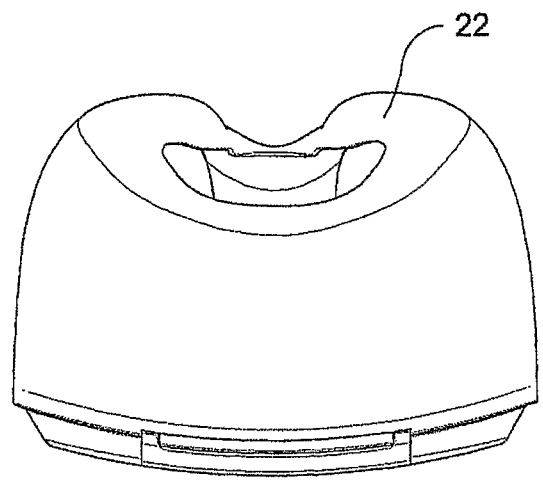
FIG. 35 is a bottom view of the flexible structure of FIG. 32.
Figure 36:
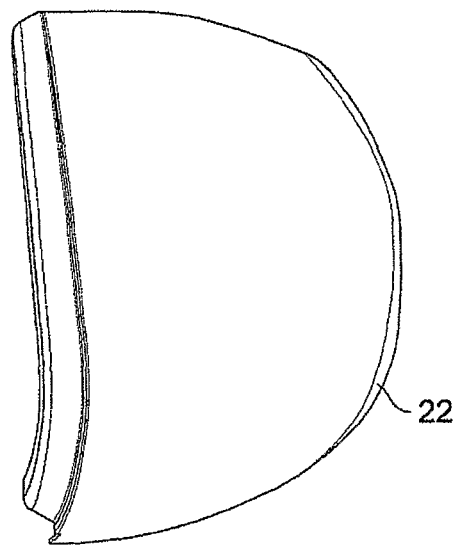
FIG. 36 is a side view of the flexible structure of FIG. 32.
Figure 37:
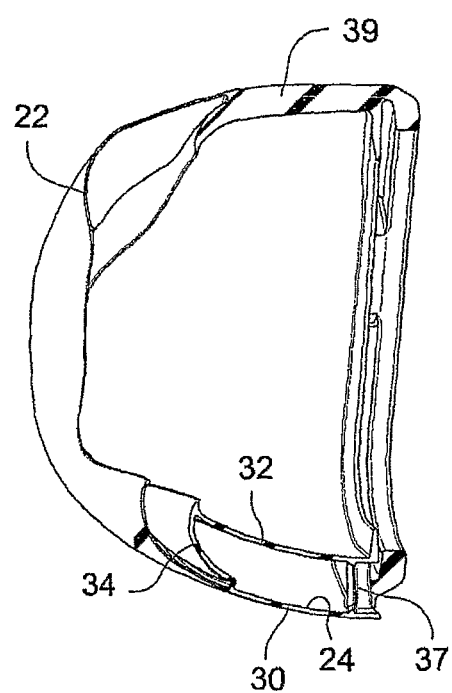
FIG. 37 is a cross-sectional view through line 37-37 of FIG. 32.
Figure 38:
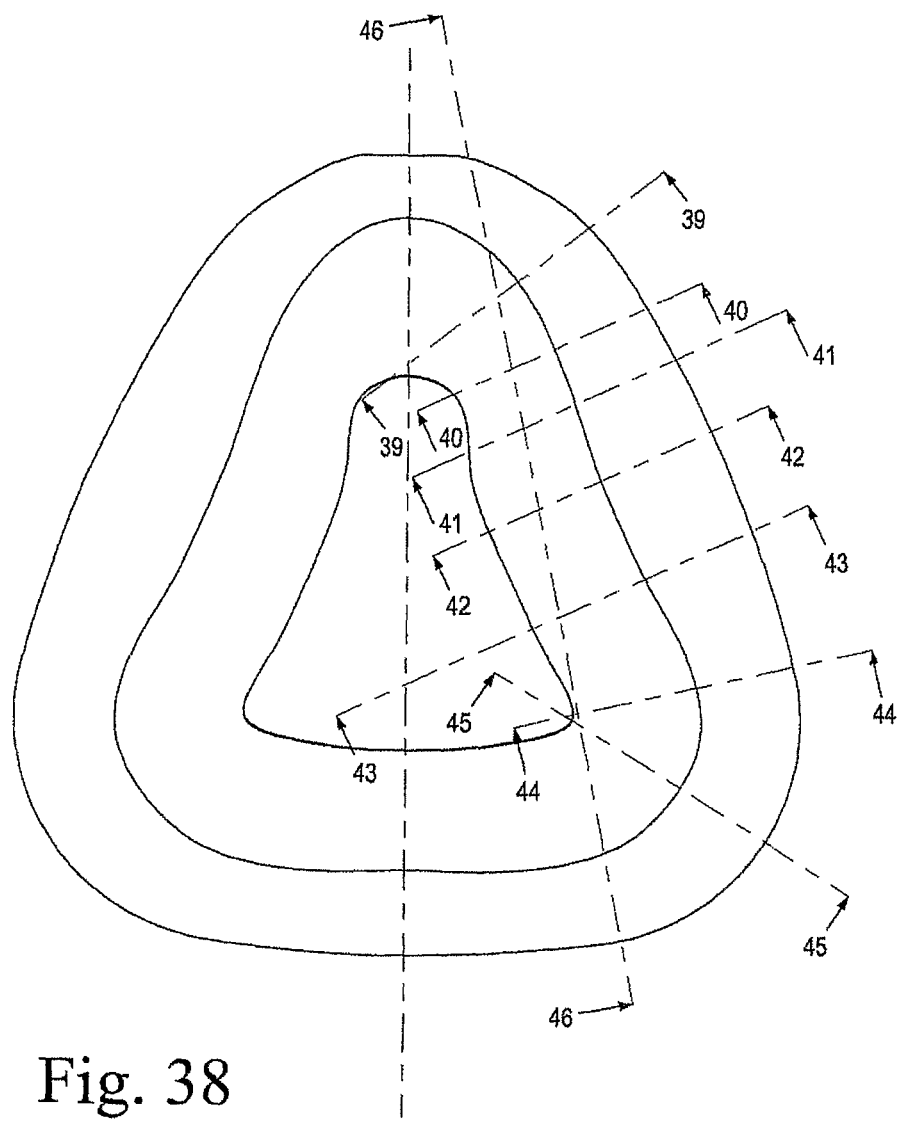
FIG. 38 is a view showing a patient contacting side of the flexible structure of FIG. 32 showing cross-section lines.
Figure 39:
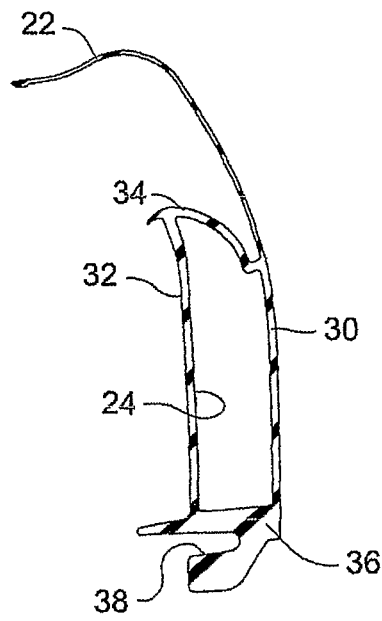
FIG. 39 is a cross-sectional view through line 39-39 of FIG. 38.
Figure 40:
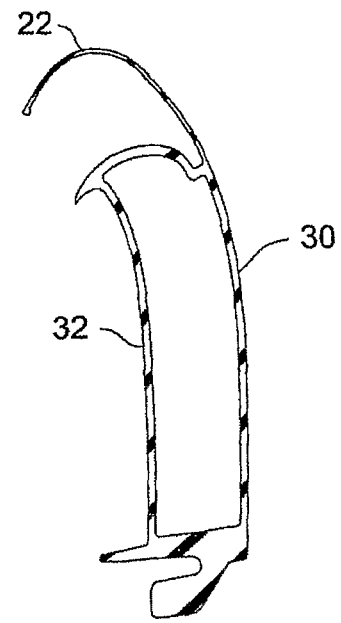
FIG. 40 is a cross-sectional view through line 40-40 of FIG. 38.
Figure 41:
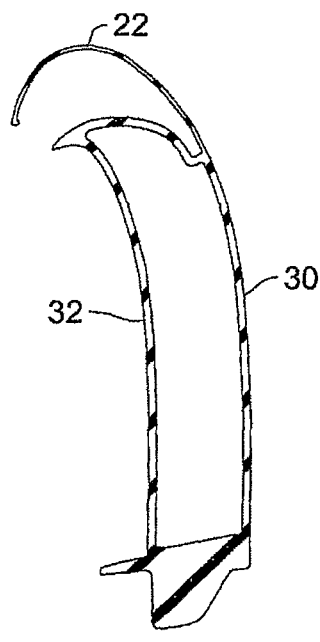
FIG. 41 is a cross-sectional view through line 41-41 of FIG. 38.
Figure 42:
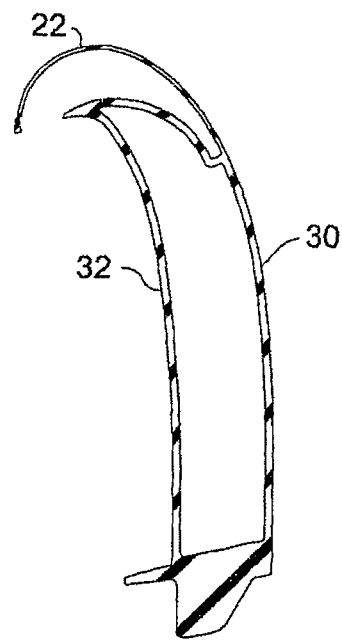
FIG. 42 is a cross-sectional view through line 42-42 of FIG. 38.
Figure 43:
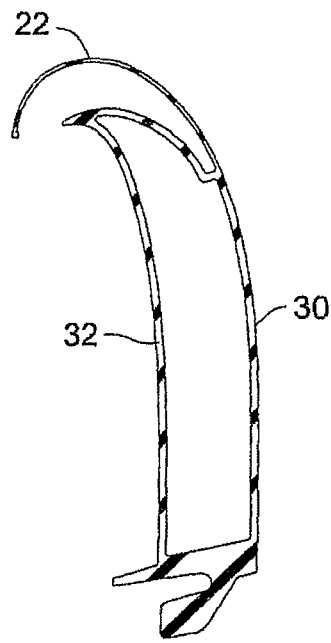
FIG. 43 is a cross-sectional view through line 43-43 of FIG. 38.
Figure 44:
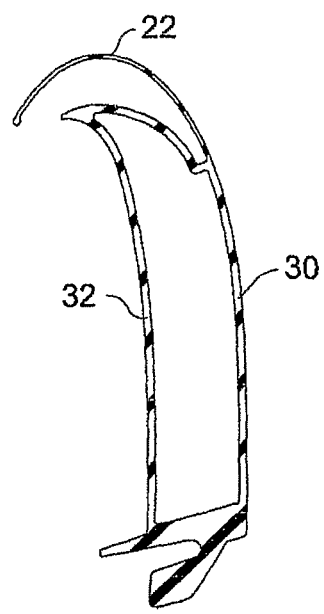
FIG. 44 is a cross-sectional view through line 44-44 of FIG. 38.
Figure 45:
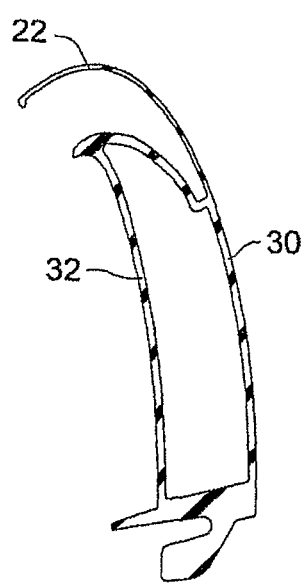
FIG. 45 is a cross-sectional view through line 45-45 of FIG. 38.
Figure 46:
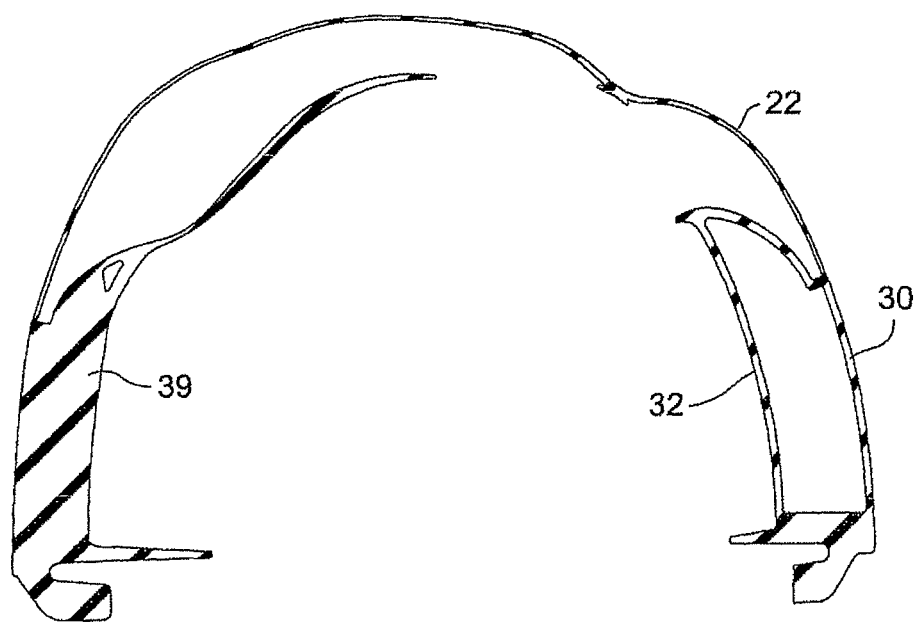
FIG. 46 is a cross-sectional view through line 46-46 of FIG. 38.

The tool used to mold the flexible structure may be precisely tuned to vary the properties of the flexible structure in different regions. For example, the inner and outer walls may have different thicknesses in the same region, or may vary in different regions about the flexible structure-, e.g., such as the lip region and the cheek region. For example, as shown in FIGS. 22 and 23, walls 30, 32 in the upper lip region may be thinner than walls 30, 32 in the cheek region.

The one or more layers of gel may be filled to different levels in different regions.

In another embodiment, different gels or gels having different properties may be provided in different regions, e.g., softer gels in nasal bridge and lip/chin regions and harder gels in cheek region. Viscous gels may be used in one region, elastic gels in another region.

Force Response Curves

An aspect of the present technology relates to a flexible structure for a mask having a defined set of force response curves, e.g., in accordance with the method described below. In accordance with an embodiment of the present technology, by varying a range of parameters such as mixing ratio of gels, thickness of walls, angles of walls, and/or height of gel layers, etc., the force response curve may be tailored, for overall cushion or individual portions/regions thereof (e.g., nasal bridge region, cheek/side regions, top lip region, chin region, etc.).

In an alternative embodiment, the gel-type flexible structure may include a gusset, such as the gusset provided on ResMed's Activa cushion.

Gel Geometry: Layer Angle (Θ), Gel Layer Depth (Y)

The following applies to a cushion with multiple layers of gel.

Figure 50:
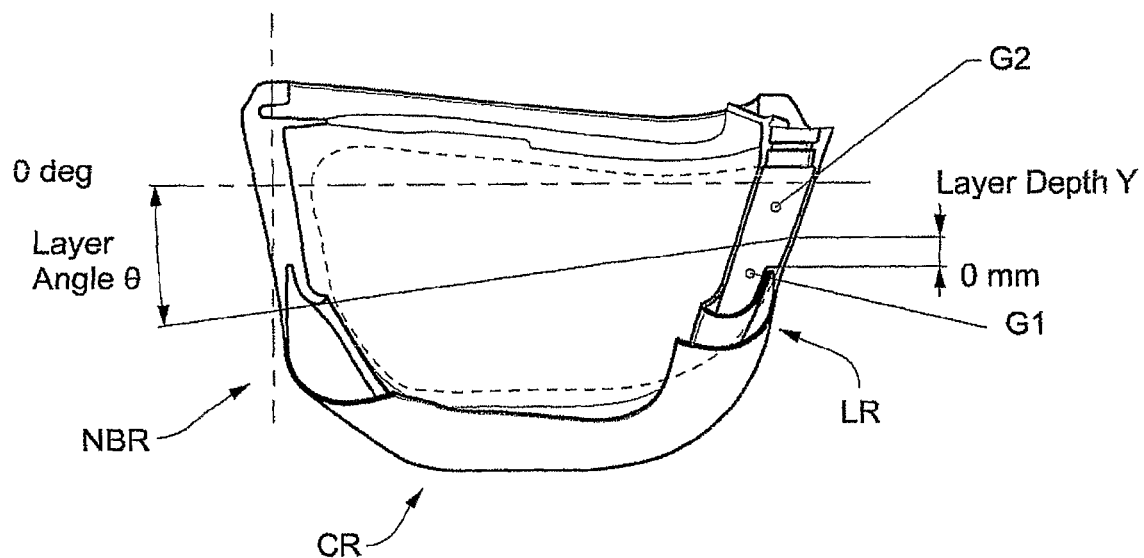
FIG. 50 is a cross-sectional view of a flexible structure showing gel geometry according to an embodiment of the present invention.
Figure 51:
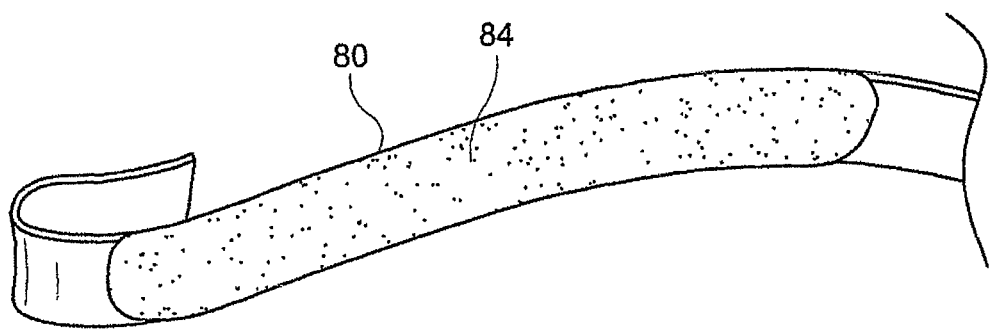
FIGS. 51-56 are various views of headgear including one or more gel bladders according to an embodiment of the present invention.
Figures 52, 53:
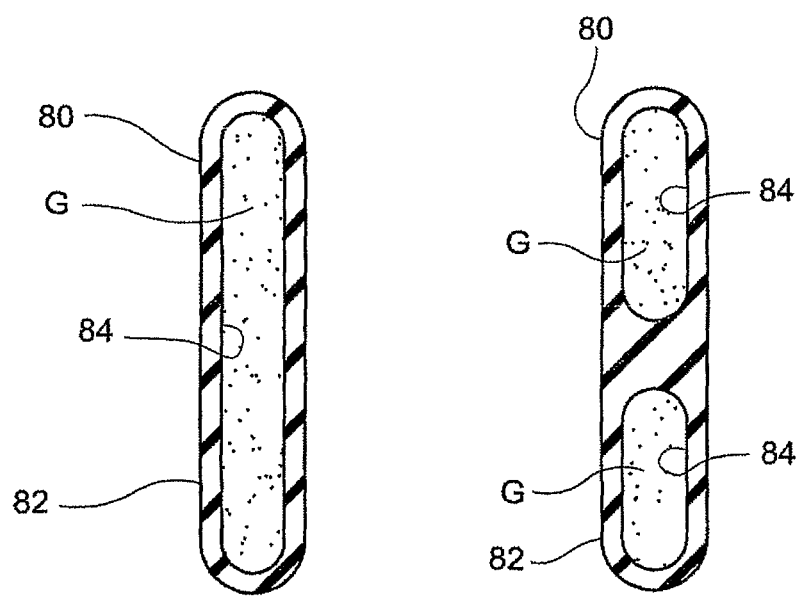

FIG. 50 defines the 0 degrees (θ) at Coordinate CAD line and 0 mm (Y) at the intersection line of the membrane to the under cushion at the patient lip contact.

An exemplary limit for the gel layer angle (θ) is within −20-20 degrees.

An exemplary limit for the gel layer depth (Y) is within 0-5 mm.

Modifying the angle (θ) of the gel layers allows the customization of the cushion force response curve at various regions. The lip region can be changed while maintaining the nasal bridge region.

Increasing the angle (θ) of the harder layers toward the nasal bridge, away from the top lip allows the softer layer of gel to allow compliance at the top lip equating to comfort, while ensuring the cushion does not buckle too readily on to the nasal bridge leading to excessive pressure.

Modifying the gel layer depth (Y) allows the customisation of the cushion force response curve at all regions. That is, increasing the amount of soft gel layer will shift the force response curve to the right for all regions (nasal bridge, top lip and cheek).

The Layer depth (Y) has a direct relationship with the layer angle (θ). Both parameters are needed, to define the geometry of the gel layers. Customising values of each and/or combinations of both parameters can influence the cushion force response curve at difference patient contact region, as can changing the amounts of viscous and or elastic gels.

The gel layer depth (Y) can be used to directly control the amount of hard and soft gel around the patient lip contact region. Adjusting this parameter alone can specifically influence the cushion force response at patient lip contact region.

Fixing the layer depth (Y), allows possible adjustment on Layer angle (θ) to influence the cushion force response around patient's cheek and nasal contact regions.

Gel Layer Hardness Delta

The difference in hardness between the two gel layers allows customization of the cushion force response curve at all regions. The slope of the force response curve is affected. As the harder gel layer(s) become engaged during cushion compression the curve will slope upwards. The higher the hardness delta the more significant the transition will be from the soft gel layer to the hard gel layer.

Refer to the figure above FIG. 50:

LAYER G1=Soft layer gel

LAYER G2=Hard layer gel

Working ranges for hardness Soft gel/hard gel ratio of: 30%-80% with nominal of 64%

4.3.5 Vacuum Formed PU Bladder

In an alternative form of cushion, a bladder is constructed using a vacuum-formed polyurethane (PU) bladder. The PU bladder may be filled with one or more of soft materials 1, 2, 3, 4, 5 and 6. In an exemplary embodiment, one or more layers may be foam, and each layer may include harder or softer foam to vary the cushion properties.

4.4 Other Gel Pockets

In an embodiment, headgear for a mask assembly may include one or more chambers, pockets, or bladders adapted for filling with soft and/or conformable materials, e.g., gel.

Figure 54:
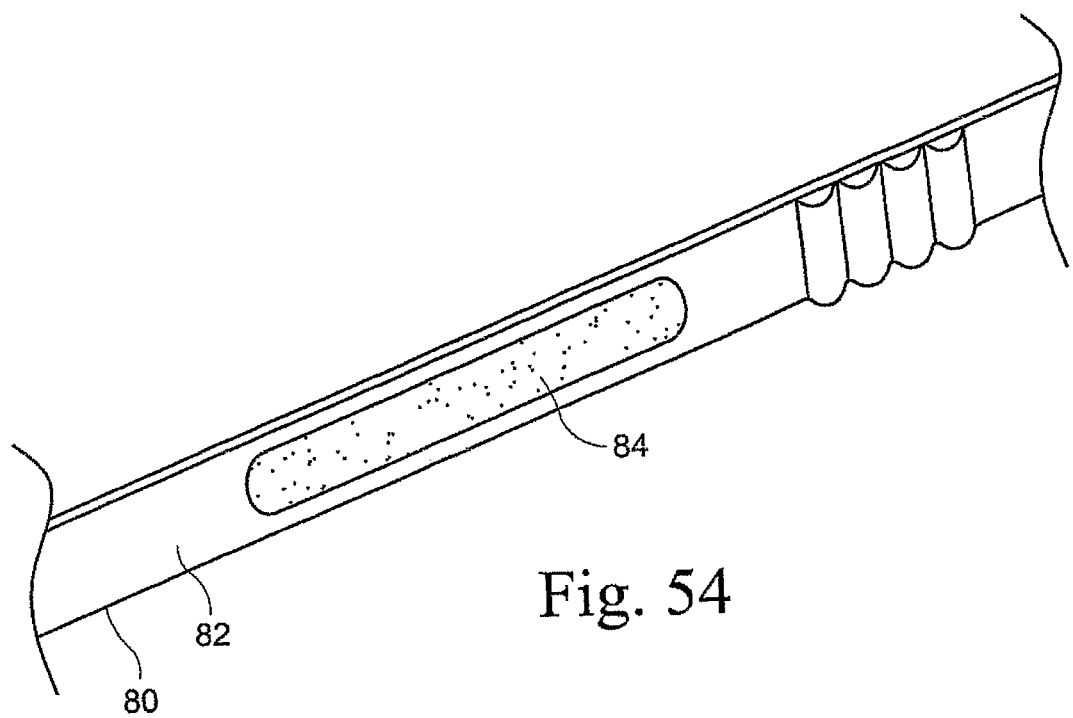
Figure 55:
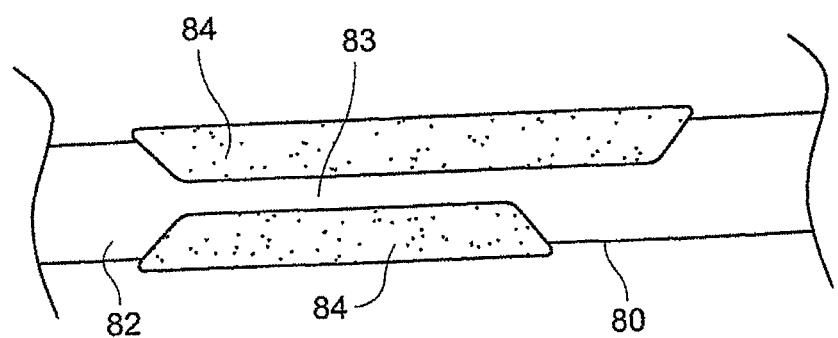
Figure 56:
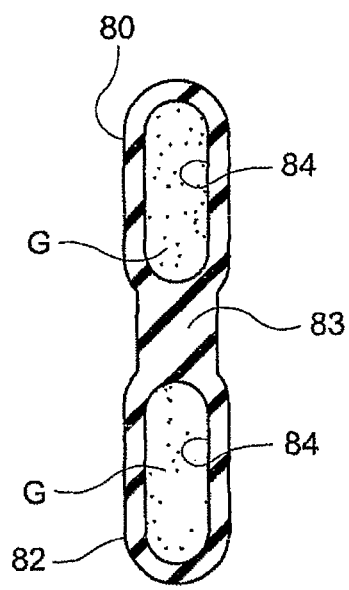

For example, as shown in FIGS. 51-56, one or more straps 80 of the headgear may include a skin 82 molded of LSR, with the walls of the skin 82 defining one or more bladders 84 filled with gel G. The bladder 84 may extend across the entire width of the strap (e.g., see FIG. 52), or two or more bladders 84 may extend across the width (e.g., see FIG. 53). FIGS. 55 and 56 shows an embodiment in which gel bladders 84 are provided along edges of the headgear strap 80, and the intermediate LSR section 83 of the strap includes a reduced thickness with respect to the gel bladders.

The one or more gel bladders may extend along the length of the headgear strap (e.g., see FIG. 51), or the bladders may be strategically located along the strap to alleviate pressure in specific regions of the patient's head in use. For example, FIG. 54 illustrates a headgear strap 80 constructed of LSR and including a gel bladder 84 along a portion of its length.

In an embodiment, the wall thickness of the bladder walls and/or the hardness of the gels may be varied to enhance comfort or feel. For example, in FIG. 53, the walls of the bladder may include a thickness of about 0.3 to 0.6 mm, and the gels may include different hardnesses with respect to one another. An inside wall may be thicker than an outside wall.

In use, the headgear with gel bladders provides an arrangement that is more comfortable, distributes pressure, relieves facial line markings, and provides tactile feedback.

Additionally, the LSR skin of the headgear may be molded with a curvature (e.g., complex 3D curves) to conform to the patient's head to assist fitting and useability. The use of gel bladders enables various gel densities to be used to create form and stability, in addition to comfort.

Other parts of a mask assembly, for example forehead pads or cheek pads may also be constructed using aspects of the present technology.

4.5 Test Methods 4.5.1 Cone Penetration ASTM D217

Container used is as per the grease cup as per ISO 2137: 2007 and or ASTM D217-02 (2007) full scale.

Standard Cone shape as per ASTM D217-02

4.5.2 Indentation Resistance ASTM D2240-02A

In relation to Type A durometers, tests were performed as per the ASTM test method.

In relation to Type OO and Type OOO durometers, we have found that many different versions of durometers said to conform to D2240 exist and give rise to different results, especially when used on very soft, viscoelastic materials such as certain gels. We note that the ASTM D2240-02a test method states at section 9.3 that readings below 20 are not considered reliable.

We have discovered the gel hardness reading is affected by: the measurement equipment (Indenter dead weight; Presser foot area; Controlled Crosshead speed; Time allowed between testing; and (if measured with an operating stand) Time delay after maximum indentation reached (t=0) to recording the hardness value (or, if measured by hand, when the presser foot first flushly contacts the test specimen-recorded within 1±0.1 seconds per section 9.2.4 of D2240-02a)); and the test specimen (Container and edge effect; Thickness of the measurement sample; and Surface flatness).

The following is the list of extra specifications in addition to the ASTM D2240 standard used in order to achieve accurate and repeatable Shore OOO measurement on soft gel of this application.

The geometry and thickness of the test sample: 40 mm thick sample, DIA 120 mm.

The measurement machine setting:

400 Grams (+/−1 gram) indenter dead weight, Bareiss Digi Test, Shore OOO

Presser foot surface area and shape, Bariess, Digi Test, Shore OOO

Controlled crosshead lowering speed/rate 3.2 mm/s, Bariess, Digi Test, Shore OOO Record hardness 60 second after the presser foot is in contact with the specimen, or when the hardness reading stops changing with time.

Allow minimum of 60 second time interval between each test made on the same specimen.

4.5.3 Rex Gauge GO

A custom gauge is available from Rex Gauge.

4.5.4 Dow Corning, Michigan, Corporate Test Method CTM 1107:

Dow Corning Corporate Test Method CTM 1107 is an indentation test method available from Dow Corning. The method measures the peak material reaction force at 10 mm indentation distance.

We used a test specimen 60 mm thickness, 120 mm diameter, top surface flat and smooth, in a flat bottomed container with the top open. The specimens are at standard laboratory temperature. The specimen is left untouched on the specimen holder for at least one minute before the test.

Results were expressed in Grams or Newtons.

Figure 60:
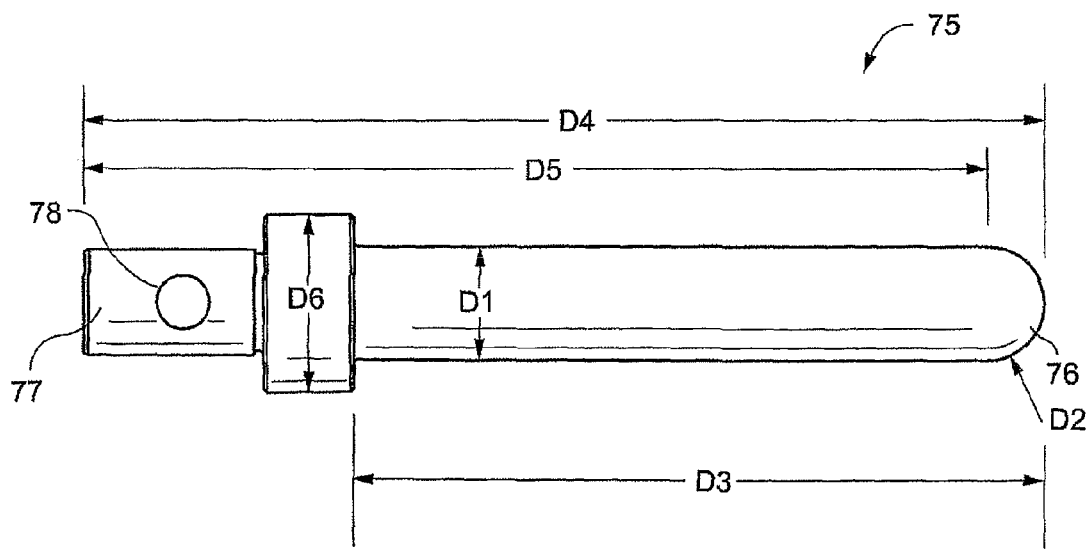
FIG. 60 is a plan view of an indenter according to another embodiment of the present invention.

The hemispherical probe used is shown in FIG. 60. The probe body has a diameter D1 of 12.7 mm. The end of the probe has a radius D2 of 6.35 mm. Also, in an embodiment, D3 is 76.2 mm, D4 is 106.2 mm, D5 is 99.85 mm, and D6 is 20 mm. However, other probes are possible and may effect the hardness test.

We did not use a trigger value of 0.5 g, instead positioned the indenter tip to "just touching" the centre of the specimen top surface, zero the indentation reading.

We repeated the procedure to make 5 measurements along the surface (edge free) at −12 mm apart and report the median of 5 measurements.

4.5.5 Force Relaxation Test Method

Figure 48:
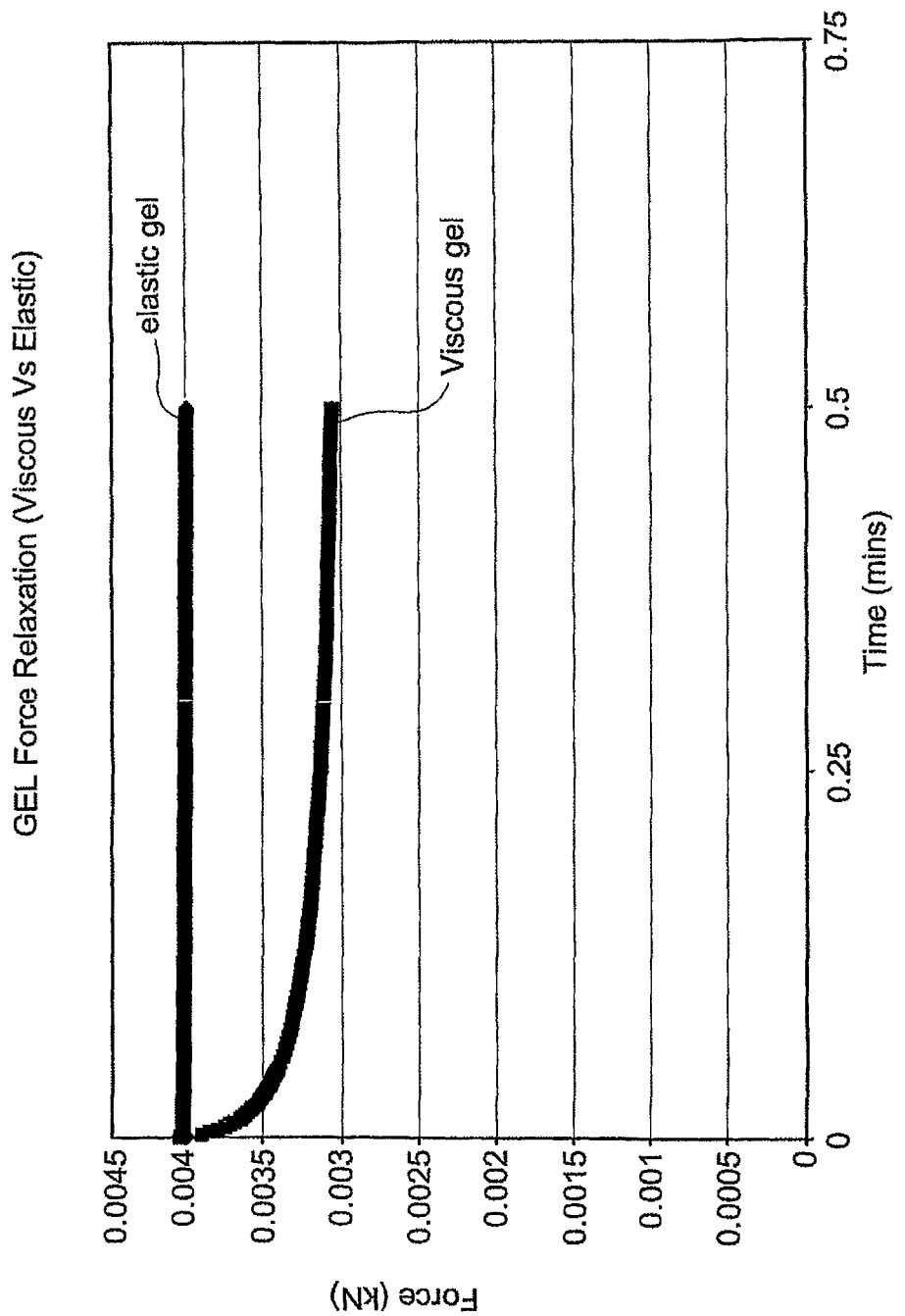
FIG. 48 is a graph of gel force relaxation.

The following force relaxation test method quantifies the change in force on an indenter on a test specimen. As shown in FIG. 48, an elastic specimen shows little or no relaxation over the test period, whereas the more viscous specimen shows a distinct loss of force over a period of about 30 seconds.

In order to quantify the relaxation, we define Rt15, the relative relaxation at 15 seconds, and Rt30, the relative relaxation at 30 seconds. These are calculated using the following formulas:

$$Rt_{15} = \frac{F_{t0} - F_{t15}}{F_{t0}}$$

$$Rt_{30} = \frac{F_{t0} - F_{t30}}{F_{t0}}$$

where Ft0 is the force at time zero, Ft15 is the force at 15 seconds and Ft30 is the force at 30 seconds.

Figure 49:
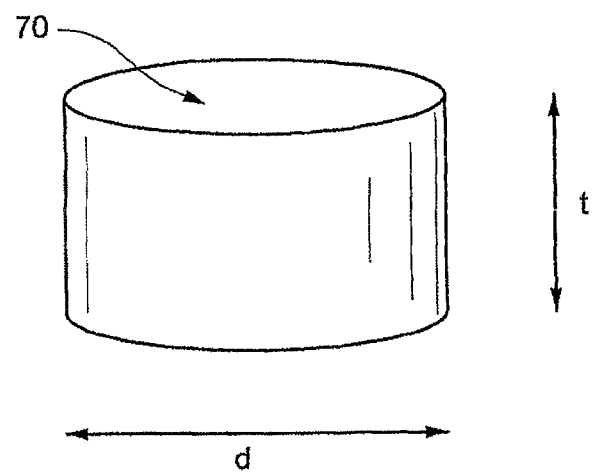
FIG. 49 is a schematic view of an exemplary test plaque for a force relaxation test.

FIG. 49 illustrates test specimen geometry. The top contact surface is flat and smooth. The test specimen has a diameter d of 60 mm and a thickness t of 40 mm. The specimen is not skinned. The specimen is not enclosed. The specimen is at standard laboratory room temperature. The specimen is left untouched on a specimen holder for at least one minute before starting the test.

The test equipment includes a force and vertical displacement controlled device, with load cell to match maximum indentation load (400 grams) and provide accurate readings.

The test equipment also includes an indenter probe as shown in FIG. 60 with suitable socket shape to the test machine.

Machine Setup

Install the hemi-spherical indenter to the load cell. Ensure there is no axial play.

Set the crosshead speed to 60 mm/min.

Set crosshead emergency stop to the maximum indentation of 35 mm to prevent reaching the bottom of the test plaque.

Set up a compression test.

Set the maximum load limit at 3.92N (equivalent to 400 g) in compression.

Set the machine control to relaxation, to hold its position for 30 seconds. (Once the load of 3.92N has been reached, it will continue to read the force values for another 30 seconds, showing the relaxation of the material over time.)

Running the Test

Place the test specimen on the specimen holder.

Position the indenter tip to "just touching" the centre of the plaque top surface. Zero the displacement (indentation) reading.

Allow the specimen to rest for 1 minute before running the test.

Balance/Zero the Load Cell.

Start/run the test machine.

Record results, post process to ensure alignment of peak value (3.92 N) with t=0. Ft15 and Ft30 are read from the data collected.

Report the average of three test results.

Other times may be chosen, e.g. 10 seconds, 60 seconds, depending on the material being tested. In such cases it may be appropriate to compare relative relaxation by calculating Ft10, Ft60 etcetera.

4.5.6 ResMed Cushion Force Indentation Test Method #1 (RCFI-1)

The method and apparatus described herein may be used to establish characteristic load/deflection behaviour of respiratory masks by measuring localized deflection of the flexible structures (e.g., cushion) of the mask under load.

In an embodiment, the indenter may be selected to eliminate variability associated with indenter point of contact. For example, there may be four indenters, i.e., one for testing the nasal bridge region, one for testing the cheek region, one for testing the top lip region, and one fore testing the chin region. The indenter shape should align with facial medians based on anthropometrics. The point of contact or placement of the indenter should have a wide tolerance band to ensure reproducibility and repeatability.

Placement of the mask onto the mask support jig (described below) should be easy to accomplish and should relate back to the way the face contacts the mask, in a nominal sense (e.g., idea is to draw a contact line between the nasal bridge and top lip under-cushion and align that to some anthropometric plane (e.g., coronal place)).

Equipment

Generic Mask Support Jig

Figure 57:
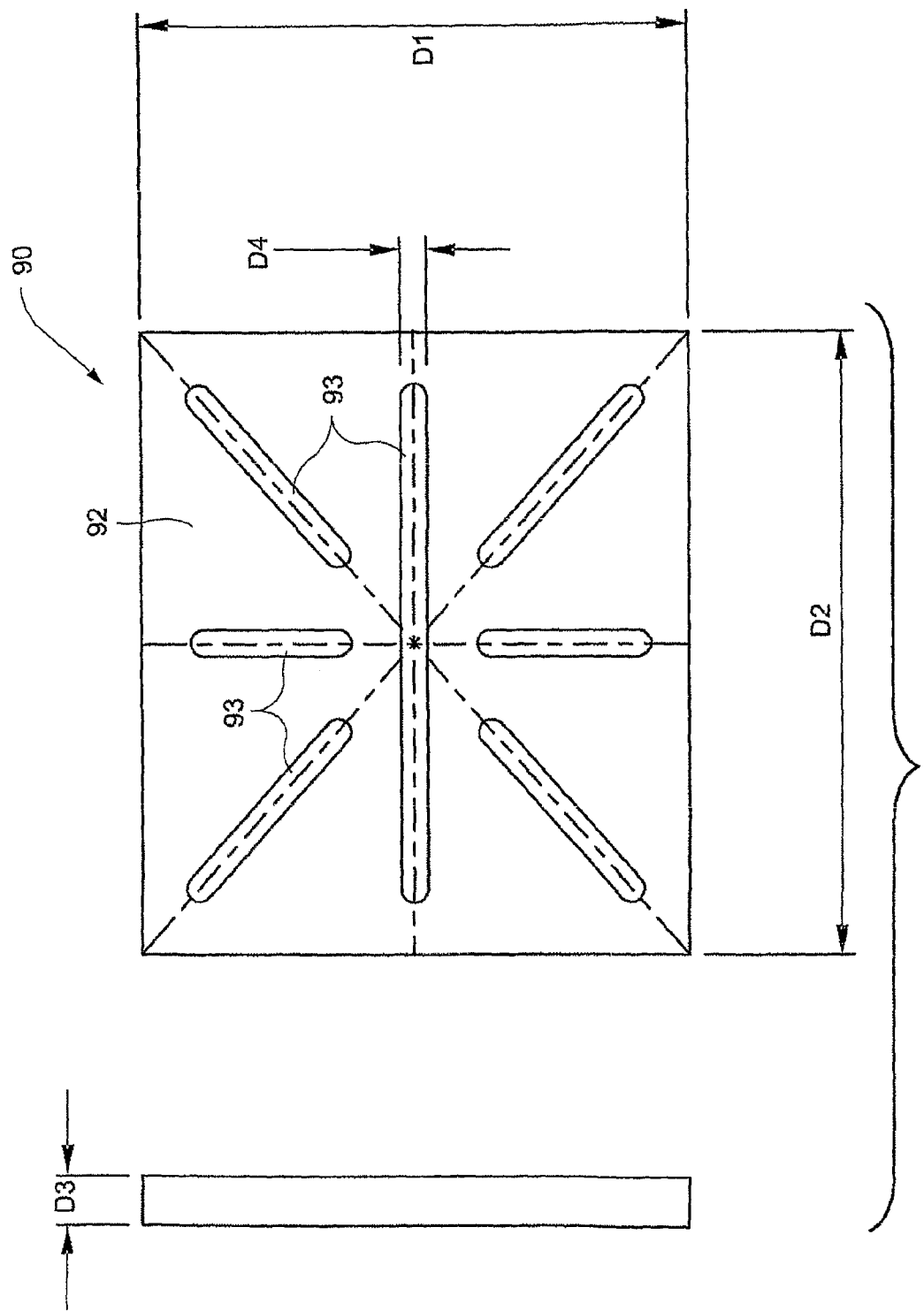
FIG. 57 illustrates a jig plate for a mask support jig according to an embodiment of the present invention.
Figure 58:
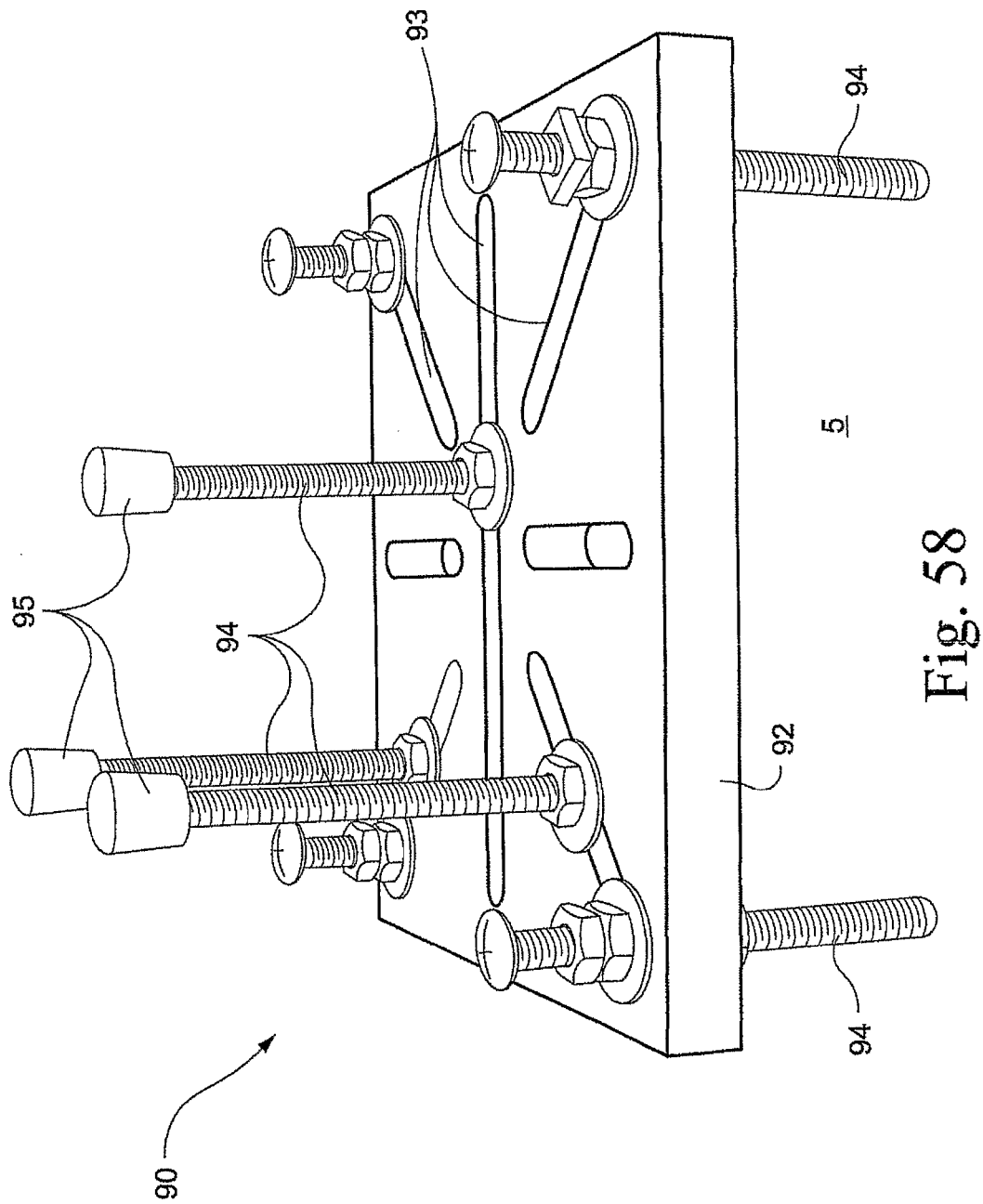
FIG. 58 is a perspective view of a mask support jig according to an embodiment of the present invention.

FIGS. 57 and 58 illustrate a mask support jig 90 according to an embodiment of the present invention. The mask support jig 90 may be used to test a number of different mask designs. As illustrated, the mask support jig 90 includes a jig plate or base 92 and a number of threaded bars 94 (with appropriate nuts/washers). The threaded bars 94 are arranged to support the plate on a support surface 5 as well as support a mask with respect to an indenter for applying loads to selected regions of the flexible structure of the mask.

As shown FIG. 57, the jig plate 92 is generally rectangular and includes an arrangement of elongated slots 93 that allow threaded bars 94 to pass therethrough unrestricted. In the illustrated embodiment, the slots 93 extend along longitudinal, transverse, and diagonal axes of the jig plate 92. However, the jig plate may have other suitable shapes and the slots may have other suitable arrangements.

In an embodiment, as shown in FIG. 57, D1 may be about 100-200 mm (e.g., 130 mm), D2 may be about 100-200 mm (e.g., 150 mm), and D3 may be about 10-20 mm (e.g., 12 mm). Also, each slot may have a width D4 of about 5-10 mm (e.g., 6.5 mm for receiving 6.35 mm threaded bars). However, other dimensions are possible, e.g., depending on application.

FIG. 58 illustrates an exemplary setup of the jig 90. As illustrated, threaded bars or bolts 94 extend through slots at respective corners of the plate 92 to support the plate on the support surface 5. In addition, multiple threaded bars 94 (e.g., three, four, or more) extend upwardly from the plate to support a mask. Each bar 94 includes a hard rubber end cap 95 that allows threaded bars to be used without damaging the masks with insignificant deflection when subject to the loads used in the test. In addition, the rubber end cap prevents slippage of the masks under load. As described below, the threaded arrangement of the bars allows the bars to be selectively adjusted (e.g., height) with respect to the jig plate and one another so as to adjust the positioning of the mask with respect to the indenter.

Spherical Head Indenter

Figure 59:
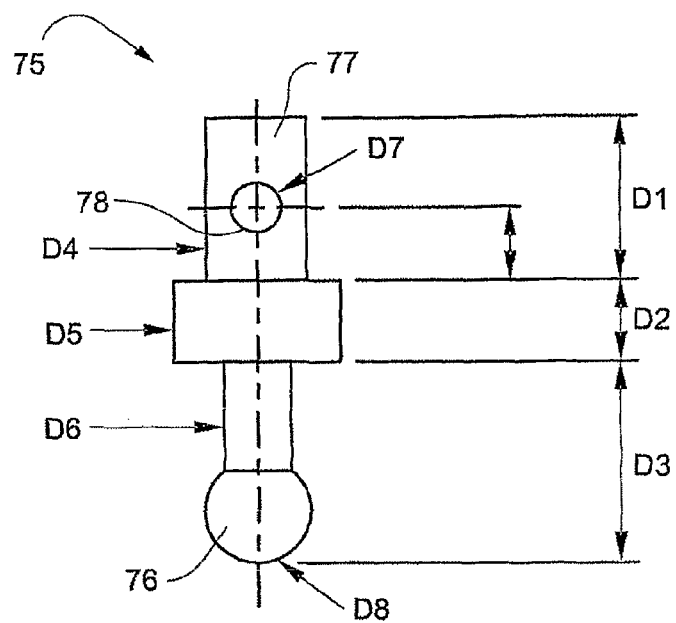
FIG. 59 is a plan view of an indenter according to an embodiment of the present invention.

FIG. 59 illustrates an indenter 75 used in the suite of testing which is derived from the standard indenter for Shore 000 hardness testing. As illustrated, the indenter 75 includes a spherical head 76 adapted to engage the test sample and a connecting portion 77 adapted to engage the test machine (e.g., secured via thru-hole 78). The Shore 000 indenter's spherical profile defined in ATSM D2240-02a is truncated, however the indenter used in these measurements uses a full spherical head in order to allow unrestricted deformation of test samples.

In an embodiment, as shown in FIG. 59, D1 is 20 mm, D2 is 10 mm, D3 is 25 mm, the diameter at D4 is 12 mm, the diameter at D5 is 20 mm, the diameter at D6 is 8 mm, the diameter of the thru hole at D7 is 6 mm, and the radius of curvature of the sphere at D8 is 6.35 mm. However, other probes are possible and may effect the hardness test.

In another embodiment, the head of the indenter may have a U-shaped profile. Such arrangement may not be as sensitive to placement or positioning on the test sample (e.g., indenter may not be centrally positioned into engagement with the test sample).

In each embodiment, the connecting portion 77 of the indenter 75 may be customized to fit on the test machine.

In an embodiment, an Instron load/deflection unit (e.g., equipment ID# ILCX00963 QUITS002) and 50N Load Cell (e.g., equipment ID# ILCX00962) may be used to support the indenter and apply the testing loads.

Set-Up

A test method according to an embodiment of the present invention is conducted by applying loads to selected regions of a flexible structure of a mask using a standardized indenter. An adjustable stand or test rig is used to support the mask such that its flexible structure faces upwards and the indenter is arranged to press down onto the flexible structure.

The test method allows for measurement of specific/localized performance rather than the bulk behaviour of the mask. The test method provides high resolution to categorize mask load/deflection in key areas of interest.

Loading Points and Orientations—General

Figure 61:
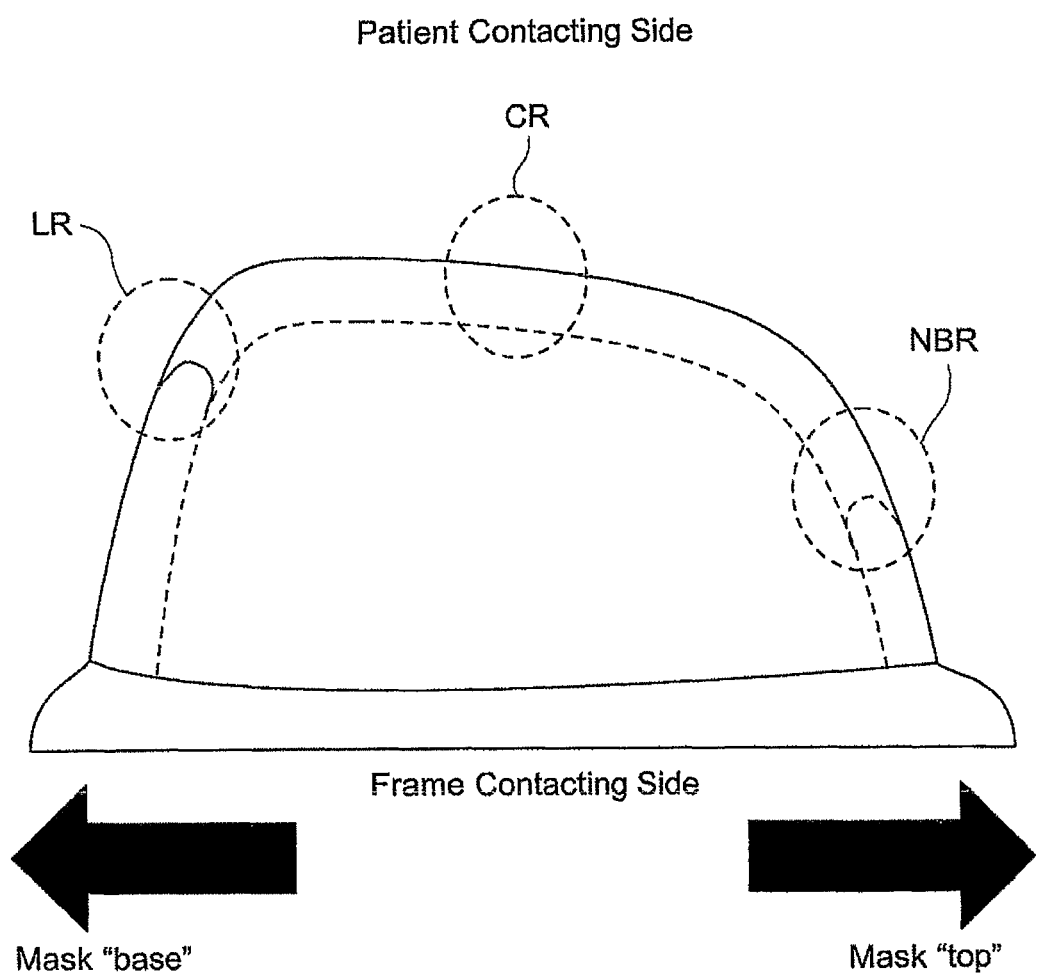
FIG. 61 shows a schematic diagram of a flexible structure for use in a respiratory mask and defines regions for the lip/chin (LR), cheek (CR) and nose or nasal bridge region (NBR) to be tested according to the method of an embodiment of the present invention.

In the test method, standardized load application points or zones have been defined. For each mask, loads are to be applied in three regions, i.e., the nose or nasal bridge region NBR, the cheek or mid-cheek region CR, and the lip/chin region LR, as shown in FIG. 61. The distinction between lip and chin for the lip/chin region is mask-dependant. That is, full-face masks typically include a flexible structure with the base or bottom supported on the chin or lower lip and nasal masks typically include a flexible structure with the base or bottom supported on the top or upper lip. The top or apex of the flexible structure is supported near the patient's nasal bridge region in both full-face and nasal masks (although the apex of the flexible structure could also be positioned lower down the patient's nose).

Since there may be significant variation in mask geometry between brands and models, standardized loading orientations have been defined, as described below.

Mask Setup-Aligning Indenter

Load Alignment Method (Nasal Bridge & Lip/Chin)

FIGS. 62 and 63 illustrate a process for aligning the nasal bridge and lip/chin regions of the flexible structure with respect to the indenter according to an embodiment of the present invention.

Mask attitude: As shown in FIG. 62, the attitude or position of the flexible structure is inclined (e.g., at an angle θ with respect to horizontal) for both nasal bridge and lip/chin regions NBR, LR such that the side walls (i.e., outer and inner walls 30, 32 of the chamber) in the nasal bridge and lip/chin regions are as near to vertical as possible. This arrangement is intended to achieve parallelism between the side walls and the direction of force application Flip/chin, Fnose (i.e., indenter travel).

Load position: As shown in FIG. 63, the indenter 75 is positioned such that it will contact the very top surface of the flexible structure. That is, the indenter is positioned into engagement with the apex of the outwardly facing or patient contacting surface 31 in the nasal bridge and lip/chin regions. In some masks, a separate membrane may be used to seal against the patient's skin, however the position of the membrane is disregarded when engaging the indenter with the flexible structure. That is, alignment is based on the side walls 30, 32 only. As shown in FIG. 63, the indenter is oriented substantially perpendicular or 90° with respect to horizontal and the flexible structure is inclined so that the side walls 30, 32 will be substantially parallel to the indenter as described above.

Load Alignment Method (Cheek)

FIG. 64 illustrates a process for aligning the cheek region of the flexible structure with respect to the indenter according to an embodiment of the present invention. The following steps should be taken:

1. Define locating plane: The application plane for loads is defined as mid way between the nasal bridge and lip/chin regions of the mask. As shown in FIG. 64, D represents the distance between the nasal bridge and lip/chin regions, so the indenter is positioned at ½ D.

2. Mask attitude: As shown in FIG. 64, the mask is inclined or tilted (e.g., at an angle θ with respect to horizontal) to ensure that the top surface of the wall in the cheek region (at the load application plane) is generally horizontal.

3. Load position: As shown in FIG. 64, the indenter is positioned into engagement with the outwardly facing surface in the cheek region, e.g., using the same technique as for nasal bridge and lip/chin regions. The indenter should be aligned (e.g., oriented 90° with respect to horizontal) such that it is aimed at the very top surface of the wall at the load application plane.

Load Alignment Method (Nasal Bridge and Lip/Chin)

It should be noted that while the orientation of the nasal bridge and lip/chin regions with respect to the indenter (see FIG. 62) are selected to keep force parallel to the side walls, the orientation of the cheek region with respect to the indenter is different. Using the technique outlined above, the side walls in the cheek region may appear to tilt inwards with respect to the indenter (i.e., side walls not parallel to the indenter) depending on the mask (see FIG. 64).

In some instances, when masks have uncommon geometry, alternative steps may be used, as described below.

Mask Setup-Specific Cases

Although FIGS. 62-64 serve to illustrate the intended orientation of masks in general, some masks require specific illustration due to their unusual geometry. FIGS. 65 and 66 provide sectional views for aligning the nasal bridge, cheek, and lip/chin regions of a flexible structure with respect to the indenter for selected masks with unusual geometry. The views shown in FIG. 66 refer to the sections defined in FIG. 65, i.e., nose or nasal bridge region, cheek region, and lip/chin region.

FIG. 66 shows loading diagrams for the SleepNet Mojo mask in the nasal bridge, cheek, and chin regions, and loading diagrams for the SleepNet Phantom mask in the nasal bridge, cheek, and lip regions. In these embodiments, the loading diagrams may be used to properly align the specified region of the flexible structure with the indenter.

Mask Mounting Procedure

FIGS. 67 and 68 illustrate an exemplary setup of a mask 10 on the mask support jig or test rig 90 described above. As illustrated, the threaded bars or support rods 94 are adjusted such that the mask 10 is supported as rigidly as possible (e.g., support rods engaged with rigid areas of the mask body or frame 40). For most masks, this will mean removing the headgear straps, forehead support if possible, and positioning the jig's support rods to form a three or four-point mount. Mounting using the far end of the forehead support should be avoided as excess body flexure of the mask will influence results. Support points should be as near to underneath the flexible structure as possible.

Once the mask mounting position has been set, the mask may be secured to the jig using one or more elastic straps to prevent slippage/movement during load/deflection measurement (e.g., see FIG. 70 which shows a mask secured to the jig with an elastic strap 96). FIG. 67 schematically illustrates the indenter 75 aligned for testing the nasal bridge region of the mask.

For more unusual masks with uncommon geometry, this sort of generic setup may not be possible. For example, additional support rods may be used to ensure rigid support of the mask on the jig. FIGS. 69 and 70 illustrate an exemplary setup for mounting the SleepNet Phantom Blue mask 210 on the jig 90. FIG. 69 is an enlarged view to more clearly show support of the mask 210 in the chin region.

Indenter Test Procedure

Determining Maximum Acceptable Loading

The following list of steps is recommended to reduce the risk of damage to masks:

1. Mount mask in generic testing jig as described above;
2. Select test location (Nose or nasal bridge region, cheek region, or lip/chin region);
3. Adjust supports in test jig to tilt/align the mask for selected loading case;
4. Install 50N load cell into Instron machine;
5. Install Shore 000 spherical head probe or indenter (e.g., see FIGS. 59 and 60) into load cell collet;
6. Turn on Instron and load Bluehill measurement software;
7. Raise Instron cross bar using manual controls such that the indenter is clear to allow placement of test jig on Instron support table;
8. Position test jig on support table of Instron;
9. Lower indenter using manual controls to a position just clear of the flexible structure of the mask;
10. Position and secure test jig for intended load case (nasal bridge region, cheek region, or lip/chin region);
11. Reset Instron extension gauge (in Instron BlueHill software);
12. Balance load cell (in Instron BlueHill software);
13. Using Instron manual controls, lower indenter so it begins to deflect flexible structure. Stop and wait until load reading updates on Bluehill software;
14. Inspect mask flexible structure and if no signs of adverse stress are visible, increase deflection fractionally. Again wait until load updates on the Bluehill software;
15. Continue steps 13 and 14 until flexible structure reaches a comfortable maximum deflection or a load of 4N is reached (which ever is the lower). A max load of 4N during test is the aim, however the load should be lowered depending on the mask's response to deflection; and
16. Record this load for use in automated testing.

Load/Deflection Testing Procedure

The following steps should be taken:

1. Using the maximum load determined above, use the following parameters in the Bluehill software:

| | |
|---|---|
| Loading type | Compressive |
| Maximum load | As determined above in maximum loading procedure |
| Extension rate | 50 mm/min |
| Raw Data export | Enabled (.csv filetype) |

2. Determine which position of mask is to be tested (nasal bridge region, cheek region, or lip/chin region);
3. Set up Instron as per steps 1-12 of maximum loading procedure described above;
4. Initiate Instron deflection via Bluehill, all the while observing the flexible structure of the mask as it deforms;
5. As a precaution, be ready to terminate testing if for any reason the flexible structure displays signs of being overstressed;
6. When deflection measurement finishes, accept prompt from Bluehill to reset indenter position;
7. Repeat steps 1-6 at least three more times in order to gather four identical tests per load case (used to ensure internal consistency of results);
8. Repeat this entire procedure for all load case points on each mask; and
9. Once testing for a mask has been completed, select "Finish" in Bluehill to save raw data.

Data Analysis and Filtering

When creating raw data files, the Instron software will, by default, produce a table containing three vectors of data: time, extension, and load. In order to make meaningful comparisons of experimental results, the data should be filtered before plotting comparative charts.

In each new test setup, the Instron extension gauge is reset prior to taking measurements, in effect defining a new datum position specific to that setup. This position, other than providing clearance between the indenter and mask, is entirely arbitrary. From test to test, the amount of clearance between the mask and indenter will differ. Consequently, it is to be expected that contact between the indenter and mask will be observed in different locations in the result list.

In order to normalize results, a trigger load may be selected and its corresponding extension (displacement from datum) taken to be the normalized or "zero" reference position. In other words, for a given trigger load, the results table is scanned and the first recorded instance of this load is noted.

The corresponding extension/displacement value is considered to be the zero point for plotting and all extension values are offset by this amount.

For the entire range of tests, a trigger load of 0.1 N (approximately 10.2 g) may be used.

4.5.7 ResMed Cushion Force Indentation Test Method #2 (RCFI-2)

The following describes a method and apparatus according to another embodiment of the present invention that may be used to establish characteristic load/deflection behaviour of respiratory masks by measuring localized deflection of the flexible structures (e.g., cushion) of the mask under load. It should be appreciated that the following test method #2 may share one or more common characteristics and features with test method #1. Also, it is to be understood that one or more features of any one test method may be combinable with one or more features of the other test method.

General Description

The testing in this experiment is conducted by applying loads to selected regions of gel mask assemblies using a standardised indenter. An adjustable jig is used to support masks such that the cushion faces upwards and the indenter is pressed down onto the cushion.

As opposed to pressing a mask onto a facial profile this method of testing allows for measurement of specific/localised performance rather than the bulk behaviour of the mask. Consequently far higher resolution is available to categorise mask load/deflection in key areas of interest.

Defining—Loading Zones and Generic Coordinate System

Load Application Zone

In order to ensure meaningful comparisons, standardised load application points have been defined for this experiment.

For each mask, loads will be applied in the nasal bridge region NBR, mid-cheek region CR and lip/chin LR as shown in FIG. 71. The distinction between lip and chin is mask-dependant. Full face masks are typically supported on the chin and nasal masks locate on the top lip.

Since there is significant variation in mask geometry between brands and models, standardised loading orientations have been defined to guarantee meaningful results. These are intended to mimic mask function.

A common cushion coordinate system has been defined in FIG. 71, in order to aid the construction of the cushion reference plane. The coordinate system has to be established for each mask. The reference plane is an important aspect as it is the measurement datum for the entire test method.

Generic Cushion Coordinating System

The following describes various parameters of FIG. 71:

W: Cushion wall, Cheek to cheek greatest width

H: Cushion wall, Nasal Bridge to lip greatest width

ZY plane: Plane of symmetry, from the nasal bridge through the lip region

ZX plane: Defining the cheek measurement point where crossing the cushion

Marking the Reference Point H/2 on a Generic Cushion

Measure the distance H between the two greatest widths of the cushion wall, on the plane of symmetry (ZY-plane). FIG. 72 illustrates the reference points (square blocks) on the generic nasal cushion.

In this example the cushion's base is also the widest length of the cushion in both X and Y-axes.

The marking of the H/2 point (indicated by an X in FIG. 72) should be visible to the top view (XY-plane), as this point is needed for aligning the alignment block from the top view as described below. In this example, the marking is on the outer membrane of the cushion as shown in FIG. 72. Use this same technique for marking the W/2 position.

Equipment

Generic Mask Support Jig

In order to produce an adaptable yet repeatable support system a jig corresponding to FIG. 73 may be used. The jig is similar to the jig described above with respect to FIGS. 57-58. As illustrated, the jig 90 of FIG. 73 includes top or jig plate 92 and a bottom or jig base 97 to support the jig plate on a support surface. The jig plate 92 with slots 93 is spaced from the jig base 97 by posts 98 arranged at respective corners of the jig.

A number of threaded bars 94 (e.g., ¼ inch 20 UNC or ¼ inch 20 BSW threaded bar) with rigid rubber end caps 95 are included in the assembly. These end caps allow threaded bars to be used without damaging the masks whatsoever and also prevent slippage of masks under load.

The end caps must be sufficiently hard, such that the deflection is minimal compared to the cushion under test.

Since the base of the jig is the datum plan for constructing the mask support plane, the jig plates should be securely flat and parallel. Parallelism between top and bottom plates (i.e., the jig plate 92 and the jig base 97) is important as this affects mask alignment and influence the quality of test measurements. FIG. 73 shows a typical jig setup.

In an embodiment, as shown in FIG. 73B, D1 may be about 100-200 mm (e.g., 150 mm), D2 may be about 100-200 mm (e.g., 170 mm), and D3 may be about 5-20 mm (e.g., 10 mm). Also, each slot may have a width D4 of about 5-10 mm (e.g., 6.5 mm for receiving threaded bars). Also, D5 may be about 85 mm, D6 may be about 75 mm, and D7 may be about 125 mm. However, other dimensions are possible, e.g., depending on application.

Indenter Head

FIGS. 74-1 to 74-3 shown an indenter 75 used in the suite of testing that is designed to minimise the placement error on the cushion. As illustrated, the sides of the head provide substantially flat surfaces 79 and the free end 76 of the head provides a polished surface finish adapted to engage the test sample. The connecting portion 77 may be modified to suit the load cell used. An engraved mark or mid-point mark 81 (e.g., 1 mm deep) is provided on both sides of the head near the free end to indicate the mid point.

In an embodiment, as shown in FIGS. 74-2 and 74-3, D1 may be about 12.7 mm, D2 may be 86.35 mm, D3 may be about 60 mm, D4 may be about 15 mm, D5 may be about 30 mm, D6 may be about R2 mm, D7 may be about 20 mm, D8 may be about 1 mm, and D9 may be about 96 mm. However, other dimensions are possible, e.g., depending on application.

The 6.35 mm radius on the leading edge (e.g., dimension D2 in FIG. 74-2) is adopted from the standard Shore OOO indenter specification. This design was modified (extruded to flat section) in order to minimise the visual alignment errors during the load setup process. The indenter reduces the likelihood of the cushion slipping off during a test. This indenter design has no direct link to the patient anthropometric data.

Alignment Block

FIG. 75 shows an alignment block 100 used in this test designed to set the standard reference plane for each cushion.

The block may be made from solid PP bar in order to evenly distribute the weight. The block may have a homogeneous mass of 382 g+/−0.5 g (including the spirit level 102) along the cushion contact point.

In an embodiment, as shown in FIG. 75, D1 may be about 60 mm and D2 may be 140 mm. However, other dimensions are possible, e.g., depending on application.

The half cylinder (e.g., R 30 mm) shape provides a stable support for block and cushion interface.

The flat section of the block is the reference plane, which accommodates a 2 axis spirit level 102 in the centre.

The 2 axes spirit level may be from RS-Components Australia (RS Stock No. 374-4810, Manufacturer Stabila)

Markings 104 may be provided at the center of the block (i.e., at D2/2 or about 70 mm) for use with the cushions cheek (H/2) alignment.

Protocol

Mask Setup Procedure

This setup method is designed to maximise repeatability for testing nasal cushions. It is important to note that the base of the jig forms and represents the 'horizontal' reference datum of this test method. During the setup, the jig should be placed on the flat horizontal surface at all times.

X & Y-Axes spirit level must be used to check the level of the test support surface.

For most masks, remove the headgear straps, forehead support if possible and position the jig's support rods to form a three or four-point mount. Mounting using the far end of the forehead support should be avoided as excess body flexure of the mask will influence results. Support points should be as near to underneath the cushion and loading zones as possible.

Setup Summary

Detailed example shown in FIG. 76

Step 1: Constrain Mask X-Axis

Mark the H/2 location on both sides of the mask, as per FIG. 72 described above Adjust the support posts to provide an approximate mask support Using a spirit level for reference, adjust support posts to ensure the mask X-Axis is horizontal Place the mask on the support posts Step 2: Align the Z-axis Place the alignment block onto the cushion and ensure that the block's mid-point marking is aligned with the H/2 marking on the cushion Settle the alignment block into the cushion such that its Z-axis is co-planar with the Z-Y plane of the mask (See settling procedure below)

At this stage, the X-axis on the block should read horizontal (see FIG. 82)

Step 3: Constrain Mask Y-axis

Adjust the support(s) so that the alignment block's Y-axis is horizontal

Securely tie down the mask and remove the alignment block

Example for Generic Nasal Mask

Step 1 Constrain Mask X-axis

Position and adjust the rear support posts such that the mask is held securely, as shown in FIG. 76. Using equal height (Z1) on both side supports, creates a good approximation for horizontal X-axis, this utilises the generic cushion symmetrical frame structure about the Z-Y plane. The parallelism of the side supports can be checked by using the spirit level as shown in FIGS. 77 and 78.

Ensure that the mask is securely supported on the sides and will not slip under load.

To complete this step, 2 posts are typically sufficient for a generic mask, although greater than 2 posts may be used if necessary. Ultimately, the mask must be able to hinge and rotate about the X-axis while maintaining the parallelism of the X-axis to the jig horizontal base.

Once the side supports (X-Axis) are set, adjust the remaining post(s) to provide an initial support to the Y-axis of the mask frame. The levelling and alignment will be set later after placing the alignment block (next step).

Step 2 Placing the Alignment Block (Aligning the Z-Axis)

Mark the H/2 location on the cushion, as per indicated in FIG. 72 described above.

Line up the H/2 mark of the cushion to the mid-point marking on the alignment block 100 as shown in FIG. 79. This placement aligns the cushion Z-axis to the block's centre of mass.

It is noted that only the patient contact region of the cushion (see FIG. 79) should support the mass of the alignment block. The forehead support or other frame parts should not contact the alignment block, as any other support on the block may influence the spirit level reading.

Step 3 Constrain Mask Y-Axis

Ensure the mask is properly reset before reading from the spirit level.

Adjust height Z2, as shown in FIG. 80 until the Y-axis of the spirit level indicates horizontal. FIG. 81 shows an example of the desired level after resetting.

Once the mask mounting position has been set in both X and Y axes, tie the mask to the jig using elastic straps to prevent slippage/movement during load/deflection measurement.

Remove the alignment block; the cushion jig set up is completed.

Reading the Alignment Block

1) Resetting the Alignment Block Before Taking Each Reading

To achieve a stable resting position for the alignment block, it is necessary to "settle" into the cushion.

After the block is placed on the cushion, reset the block by evenly pressing the block down (about 3-5 mm) and holding stationary for 5 seconds. While holding, balance the weight (horizontal) by maintaining the spirit level horizontal in both axes. It is important to note that pressing the block unevenly can affect the spirit level reading on the block.

2) Reading the Y-Axis Level (Important for Step 3 of Constraining Mask Y-Axis Described Above)

Before taking the Y-axis reading the block should read horizontal in X-axis.

After each reset, the block is only allowed be turned axially as shown in FIG. 82. The mid-point of the block (Z-axis) should remain aligned with the H/2 mark at all times.

Reset the block if needed, until the X-axis is horizontal as shown in FIG. 82.

Jig Support for Non-Generic Mask

For the more unusual masks a 3-post generic setup may not be possible. One such unusual mask is the Sleep Net Phantom. FIGS. 69 and 70 described above are examples of how to mount the SleepNet Phantom mask. FIGS. 83 and 84 also illustrate an example of how to mount the SleepNet Phantom mask 210, including placement of the alignment block 100.

Load Position

Views shown in the following loading diagrams refer to sections defined in FIG. 65.

Load Alignment Method (Cheek)

Defining locating plane: The application plane for load is defined as mid way between the nasal bridge and lip/chin positions on the mask (at H/2)

Load position: The indenter should be aligned such that it is aimed at the very top surface of the gel-filled wall at the load application plane. The indenter 'flat surface' (e.g., flat surfaces 79 in FIGS. 74-1 to 74-3) should always cross the gel cushion wall at 90° to the wall, viewed from the Z-axis, as shown in FIGS. 85 and 86. Before recording data, the indenter position should be tested to ensure cushion maintains contact with the indenter and does not slip off this leading edge during deflection testing. Use this same technique for nasal and lip/chin regions.

Load Alignment Method (Nasal Bridge and Lip/Upper Chin)

Defining locating plane: The application plane for loads is defined on the symmetrical Z-Y plane (W/2 as per shown in FIG. 71).

Load position: The mid-point indicator 81 (see FIGS. 74-1 to 74-3) on the indenter flat surfaces 79 should be approximately in the middle of the cushion wall, provided that the indenter can travel its full range of motion without the cushion losing contact.

An example of the Nasal bridge setting is shown in FIGS. 87 and 88.

In some instances, when masks have uncommon geometry the steps outlined above are not sufficient to specify consistent alignment of the mask. Refer to FIG. 66 described above for a description of selected test cases.

Indenter Test Procedure

Determining Maximum Acceptable Loading

Many masks likely to be tested as per this procedure are no longer sold and are therefore irreplaceable. The following technique is important to ensure that legacy masks are not damaged in any way.

1. Mount mask in generic testing jig and establish orientation (as per mask setup procedure described above)
2. Select test location (Nose, cheek or lip/chin)
3. Install 50N load cell into Instron machine
4. Install the ResMed FD flat indenter head probe (See FIGS. 74-1 to 74-3) into load cell collet (Ensure non-pivoting connector is used)
5. Turn on Instron and load Bluehill measurement software
6. Raise Instron cross bar using manual controls such that the indenter is clear to allow placement of test jig on Instron support table
7. Position test jig on support table of Instron
8. Lower indenter using manual controls to a position just clear of mask cushion
9. Position and secure test jig for intended load case (nasal, cheek or lip/chin)
10. Reset Instron extension gauge (in Instron BlueHill software)
11. Balance load cell (in Instron BlueHill software)
12. Using Instron manual controls, lower indenter so it begins to deflect cushion. Stop and wait until load reading updates on Bluehill software
13. Inspect mask cushion and if no signs of adverse stress are visible, increase deflection fractionally. Again wait until load updates on the Bluehill software
14. Continue steps 12 and 13 until cushion reaches a comfortable maximum deflection or a load of 4N is reached (which ever is the lower). A max load of 4N during test is the aim, however the load should be lowered depending on the mask's response to deflection
15. Record this load for use in automated testing Load/Deflection Testing Procedure 1. Using the maximum load determined above, use the following parameters in the Bluehill software:
   Loading type—Compressive
   Maximum load—As determined above in maximum loading procedure
   Extension rate—50 mm/min
   Raw Data Export—Enabled (.csv filetype)
2. Determine which position of mask is to be tested (nasal bridge, cheek or lip/chin)
3. Set up Instron as per steps 1-11 regarding maximum loading described above
4. Initiate Instron deflection via Bluehill, all the while observing the mask cushion as it deforms
5. As a precaution be ready to terminate testing if for any reason the cushion displays signs of being overstressed. Position mouse over cancel button in the software or use the emergency stop button on the Instron. If available, program the software (in this case Bluehill) to terminate the test when the maximum allowable travel is reached.
6. When deflection measurement finishes, reset indenter position
7. Repeat steps 1-6 at least two more times in order to gather identical tests per load case (used to ensure internal consistency of results)
8. Repeat this entire procedure for all load case points on each mask Save raw data once completed for result formatting.

Result Formatting

Data Analysis and Filtering

When creating raw data files, the Instron software will, by default, produce a table containing three vectors of data: time, extension and load. In order to make meaningful comparisons of experimental results the data need to be filtered before plotting comparative charts.

In each new test setup, the Instron extension gauge is reset prior to taking measurements, in effect defining a new datum position specific to that setup. This position, other than providing clearance between the indenter and mask, is entirely arbitrary. From test to test, the amount of clearance between the mask and indenter will differ. Consequently it is to be expected that contact between the indenter and mask will be observed at different locations in the result list.

In order to normalise results, a trigger load must be selected and its corresponding extension (displacement from datum) taken to be the normalised or "zero" reference position for that data set. In other words, for a given trigger load, the results table is to be scanned and the first recorded instance of this load are noted. The corresponding extension/displacement value is considered to be the zero point for plotting/normalising and all extension values are offset by this amount.

In previous testing, a trigger load of 0.1 N has been used and is suggested for reasons of consistency. Unless impossible (as determined by data set), a load of 0.1N should be used for normalising.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. For example aspects of the technology may be adapted for full-face masks, and nasal pillows masks. Further, while the use of liquid silicone rubber (LSR) is described, it will be appreciated that the use of other suitable moldable elastomers is encompassed herein. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A respiratory mask, comprising:
a frame; and
a flexible structure provided to the frame and adapted to engage a patient's face, the flexible structure including a chamber filled with a first gel layer and a second gel layer that is relatively harder than the first gel layer, wherein:
a ratio of height of the first gel layer to the second gel layer in a lip region is in the range of about 0.25 to about 0.6,
the chamber includes inner and outer walls that are curved or angled inwardly along their entire length from a frame side thereof to a patient side thereof towards a breathing chamber of the flexible structure so as to promote controlled bending of the flexible structure towards the breathing chamber at a boundary between the first and second gel layers as force is progressively applied to the flexible structure, and
the flexible structure includes a seal-forming flap structured to substantially cover at least a portion of the chamber.

2. A respiratory mask according to claim 1, wherein the first gel layer ranges in height in the lip region from about 4 mm to about 7 mm.

3. A respiratory mask according to claim 1, wherein the second gel layer ranges in height in the lip region from about 12 mm to about 15 mm.

4. A respiratory mask according to claim 1, wherein a ratio of height of the first gel layer to the second gel layer in a cheek region is in the range of about 0.5 to about 1.7.

5. A respiratory mask according to claim 4, wherein the first gel layer ranges in height in the cheek region from about 10 mm to about 15 mm.

6. A respiratory mask according to claim 4, wherein the second gel layer ranges in height in the cheek region from about 9 mm to about 18 mm.

7. A respiratory mask according to claim 1, wherein the chamber extends around the entire perimeter of the flexible structure.

8. A respiratory mask according to claim 1, wherein the chamber extends only around a portion of the perimeter of the flexible structure.

9. A respiratory mask according to claim 8, wherein the flexible structure is a nasal cushion, and the chamber with first and second gel layers is provided in cheek and upper lip regions of the cushion and a solid silicone portion is provided in a nasal bridge region of the cushion, without any gel.

10. A respiratory mask according to claim 1, wherein the first gel layer is adapted to be positioned closer to the patient's face in use.

11. A respiratory mask according to claim 1, wherein the first gel layer and the second gel layer are stacked in an axial direction.

12. A respiratory mask according to claim 1, wherein the inner and outer walls include an inwards slope or curvature from the frame side to the patient side of the flexible structure.

13. A respiratory mask, comprising:
a frame; and
a flexible structure provided to the frame and adapted to engage a patient's face, the flexible structure including a chamber filled with a first gel layer and a second gel layer,
the chamber including inner and outer walls that are curved or angled inwardly along their entire length from a frame side thereof to a patient side thereof towards a breathing chamber of the flexible structure so as to promote controlled bending of the flexible structure towards the breathing chamber at a boundary between the first and second gel layers as force is progressively applied to the flexible structure, and
the flexible structure including a sealing flap that extends inwardly from the outer wall of the chamber and in covering relation to the chamber.

14. A respiratory mask according to claim 13, wherein the first gel layer is relatively softer than the second gel layer and adapted to be positioned closer to the patient's face in use.

15. A respiratory mask according to claim 13, wherein a ratio of height of the first gel layer to the second gel layer is different in different regions of the flexible structure along its perimeter.

16. A respiratory mask according to claim 15, wherein a ratio of height of the first gel layer to the second gel layer in a lip region is in the range of about 0.25 to about 0.6.

17. A respiratory mask according to claim 15, wherein a ratio of height of the first gel layer to the second gel layer in a cheek region is in the range of about 0.5 to about 1.7.

18. A respiratory mask according to claim 13, wherein the boundary between the first gel layer and the second gel layer is at least partially determinative of a hinge point so as to further promote controlled bending of the flexible structure at the hinge point.

19. A respiratory mask according to claim 13, wherein the inner and outer walls include an inwards slope or curvature from the frame side to the patient side of the flexible structure.

20. A respiratory mask, comprising:
a frame; and
a flexible structure provided to the frame and adapted to engage a patient's face, the flexible structure including a chamber filled with a first gel layer and a second gel layer,
the first gel layer being relatively softer than the second gel layer and adapted to be positioned closer to the patient's face in use,
wherein a ratio of height of the first gel layer to the second gel layer is different in different regions of the flexible structure along its perimeter,
wherein the flexible structure is a nasal cushion, and the chamber with first and second gels is provided in cheek and upper lip regions of the cushion and a solid silicone portion is provided in a nasal bridge region of the cushion, without any gel,
wherein the chamber includes inner and outer walls that are curved or angled inwardly along their entire length from a frame side thereof to a patient side thereof towards a breathing chamber of the flexible structure so as to promote controlled bending of the flexible structure towards the breathing chamber at a boundary between the first and second gel layers as force is progressively applied to the flexible structure, and wherein the respiratory mask further comprises a sealing flap that extends inwardly from the outer wall of the chamber and in covering relation to the chamber.

21. A respiratory mask according to claim 20, wherein the boundary between the first gel layer and the second gel layer is at least partially determinative of a hinge point so as to further promote controlled bending of the flexible structure at the hinge point.

* * * * *